United States Patent
McMahon et al.

(10) Patent No.: US 10,590,383 B2
(45) Date of Patent: Mar. 17, 2020

(54) METHODS FOR DIFFERENTIATING PLURIPOTENT CELLS

(71) Applicant: FUJIFILM Cellular Dynamics, Inc., Madison, WI (US)

(72) Inventors: Christopher W. McMahon, Madison, WI (US); Lauren E. Little, Madison, WI (US); Wen Bo Wang, Madison, WI (US); Nathaniel A. Elliott, Madison, WI (US)

(73) Assignee: FUJIFILM Cellular Dynamics, Inc., Madison, WI (US)

( * ) Notice: Subject to any disclaimer, the term of this patent is extended or adjusted under 35 U.S.C. 154(b) by 25 days.

(21) Appl. No.: 15/678,432

(22) Filed: Aug. 16, 2017

(65) Prior Publication Data

US 2018/0051248 A1 Feb. 22, 2018

Related U.S. Application Data

(60) Provisional application No. 62/375,590, filed on Aug. 16, 2016.

(51) Int. Cl.
| | |
|---|---|
| *C12N 5/00* | (2006.01) |
| *C12N 5/0793* | (2010.01) |
| *A61K 38/18* | (2006.01) |
| *C12N 5/0797* | (2010.01) |
| *C07C 215/28* | (2006.01) |
| *C07C 229/36* | (2006.01) |
| *G01N 33/50* | (2006.01) |

(52) U.S. Cl.
CPC .......... *C12N 5/0619* (2013.01); *A61K 38/185* (2013.01); *C12N 5/0623* (2013.01); *C07C 215/28* (2013.01); *C07C 229/36* (2013.01); *C12N 2501/415* (2013.01); *C12N 2501/999* (2013.01); *C12N 2506/02* (2013.01); *C12N 2506/45* (2013.01); *G01N 33/5058* (2013.01); *G01N 33/5073* (2013.01)

(58) Field of Classification Search
CPC .............. C12N 5/0649; C15N 2506/02; C15N 2506/45
See application file for complete search history.

(56) References Cited

U.S. PATENT DOCUMENTS 9,694,036 B2 * 7/2017 George .................... A61J 1/00
2015/0265652 A1 9/2015 Matt et al.

FOREIGN PATENT DOCUMENTS

| WO | WO 2013/067362 | 5/2013 |
| WO | WO 2016/196661 | 12/2016 |

OTHER PUBLICATIONS

International Search Report and Written Opinion issued in corresponding International Application No. PCT/US2017/047124, dated Nov. 30, 2017.
Kikuchi et al., "Human iPS cell-derived dopaminergic neurons function in a primate Parkinson's disease model," *Nature*, 548(7669):592-596, 2017.
Kriks et al., "Floor plate-derived dopamine neurons from hESCs efficiently engraft in animal models of PD," *Nature*, 480(7378):547-551, 2011.
Liu et al., "Chemical Modulation of Cell Fate in Stem Cell Therapeutics and Regenerative Medicine," *Cell Chem. Biol.*, 23(8):893-916, 2016.

* cited by examiner

*Primary Examiner* — Marcia S Noble
(74) *Attorney, Agent, or Firm* — Parker Highlander PLLC

(57) ABSTRACT

Methods are provided, in some aspects, for differentiating pluripotent cells into midbrain dopaminergic (DA) neurons using a mono-SMAD inhibition or inhibition of SMAD signaling with only one SMAD inhibitor. In some embodiments, mono-SMAD inhibition utilizes a single inhibitor of bone morphogenic protein (BMP) for differentiating pluripotent cells into midbrain DA neurons.

62 Claims, 17 Drawing Sheets

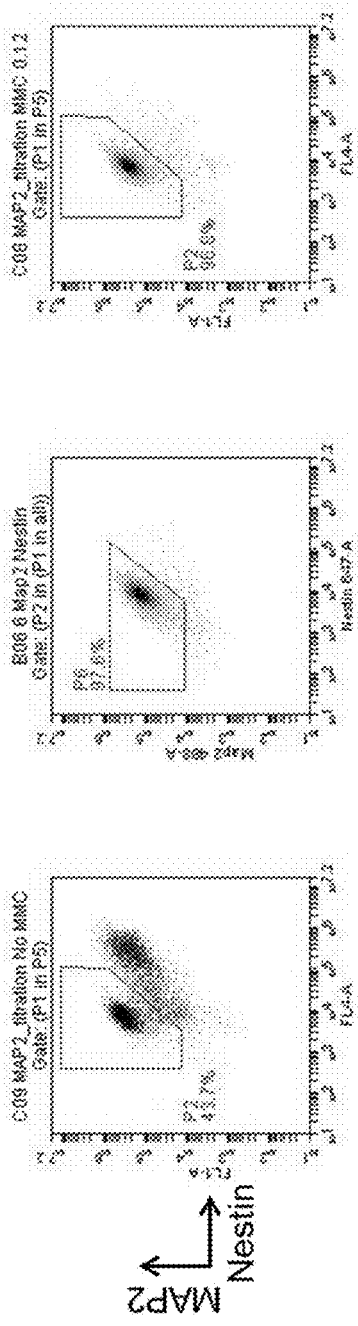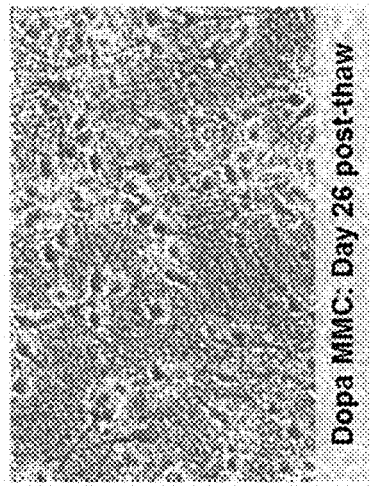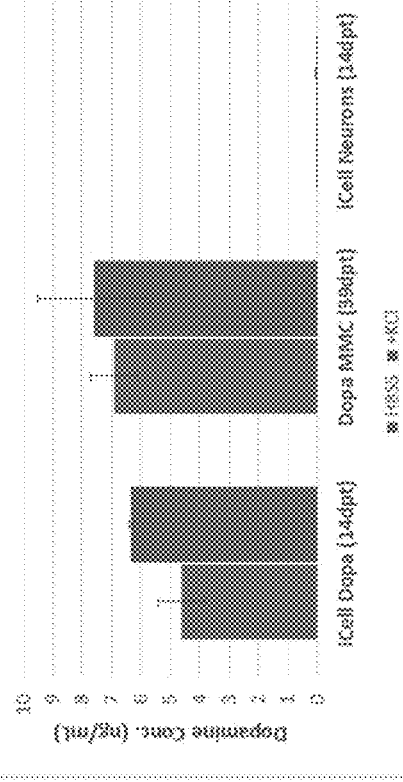
FIGS. 4A-C

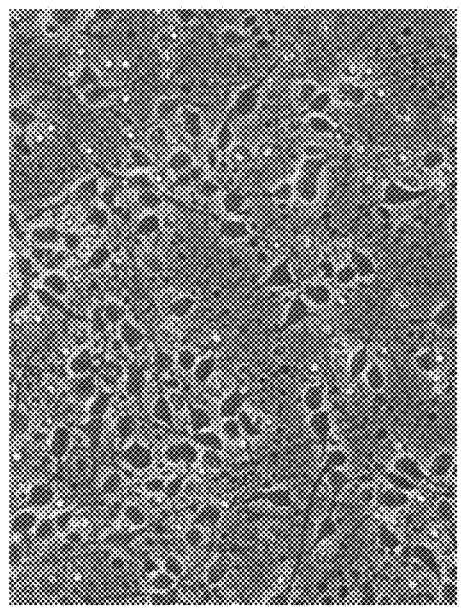
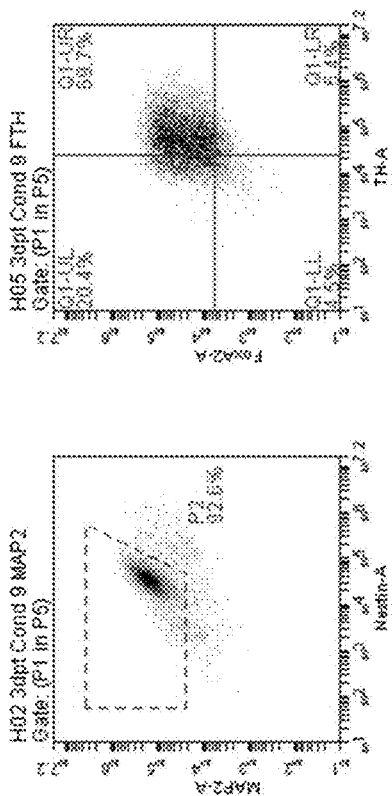
| Viability at Thaw (%) | 80.1 |
| Plating Efficiency (%) | 63.5 |
| Cells Expressing MAP2 (%) | 92.6 |
| Cells Expressing FoxA2 (%) | 90.1 |
| Cells Expressing FoxA2 and TH (%) | 69.7 |
FIG. 6

METHODS FOR DIFFERENTIATING PLURIPOTENT CELLS

This application claims the benefit of U.S. Provisional Patent Application No. 62/375,590, filed Aug. 16, 2016, the entirety of which is incorporated herein by reference.

BACKGROUND OF THE INVENTION

1. Field of the Invention

The present invention relates generally to the field of molecular biology and medicine. More particularly, it concerns methods of generating dopaminergic neurons from pluripotent cells.

2. Description of Related Art

Cell populations that retain the ability to differentiate into numerous specialized cell types are useful for developing large numbers of lineage specific differentiated cell populations. These lineage specific differentiated cell populations are contemplated to find use in cell replacement therapies for patients with diseases resulting in loss of function of a defined cell population. In addition to their direct therapeutic value, lineage specific differentiated cells are also valuable research tools for a variety of purposes including in vitro screening assays to identify, confirm, and test for specification of function or for testing delivery of therapeutic molecules to treat cell lineage specific disease.

In the case of Parkinson's disease, for example, it is the loss of midbrain dopaminergic (DA) neurons that results in the appearance of disease symptoms. Thus, there is need for methods of producing DA neuronal cells from pluripotent cells, since such cells could be used both therapeutically and in disease models, e.g., to identify new therapeutics for treatments for Parkinson's disease.

Various efforts have been made to generate midbrain DA neurons from pluripotent cells. For example, methodologies for generating midbrain DA neurons from pluripotent cells typically require use of both LDN-193189, an inhibitor of BMP signaling (inhibits ALK 1/2/3/6, blocks SMAD 1/5/8), and SB-431542, an inhibitor of TGF-beta signaling (inhibits ALK 4/5/7, blocks SMAD 2/3), as described, e.g., in WO2013/067362. Since these methods utilize the combination of two inhibitors of Small Mothers Against Decapetaplegic (SMAD) signaling, these methods are typically referred to as "dual SMAD inhibition", or "dual SMADi." Although it may be desirable to create a method for generation of midbrain dopaminergic (mDA) neurons from induced pluripotent stem (iPS) cells using only a single SMAD inhibitor, such efforts have thus far been a failure. Clearly, there exists a need for methods of generation of mDA neurons from iPS cells using only a single SMAD inhibitor.

SUMMARY OF THE INVENTION

The present invention overcomes limitations in the prior art by providing, in some aspects, methods for generating neurons from pluripotent cells using mono-SMAD inhibition (mono-SMADi). Use of mono-SMADi methods can provide advantages over methods which require inhibition of SMAD signaling using two or more SMAD inhibitors. As described in the below examples, provided are methods for generating neural cell lines such dopaminergic neurons from pluripotent cells, such as human induced pluripotent cells (iPS cells). As shown herein, several aspects may be included in these methods including: (i) staggering the addition of a Wnt agonist (e.g., CHIR99021) to day 2 or day 3, (ii) re-optimizing the CHIR concentration (e.g., using from about 0.5-3.0 µM, 0.7-3 µM, 1-2.5 µM, 1.25-2.25 µM, from greater than about 1.25 µM to about 2 µM, or about 1.55, 1.65, 1.75 µM, or any range derivable therein), and/or (iii) including a MEK inhibitor (e.g., PD0325901) in the differentiation media on days 3-5. The methods may include, e.g., aspects (i and ii), (ii and iii), (i and iii), or (i, ii, and iii) above. In some embodiments, cells are exposed to a BMP inhibitor (e.g., dorsomorphin or LDN-193189) and the cells are not exposed to a TGF-β inhibitor such as SB431542, to promote differentiation of cells into midbrain DA neurons or FOXA2$^+$/LMX1A$^+$ cells. As shown in the below examples, these methods may be used for highly-efficient mDA progenitor formation from iPS cell lines with media only including a single SMAD inhibitor (e.g., dorsomorphin only or LDN-193189 only).

An aspect of the present invention relates to an in vitro method for preparing a cell composition comprising human cells that express both forkhead box protein A2 (FOXA2) and LIM homeobox transcription factor 1 (LMX1) (FOXA2$^+$/LMX1$^+$ cells) comprising culturing human pluripotent cells in the presence of the following signaling modulators: (a) a single inhibitor of Small Mothers Against Decapentaplegic (SMAD) signaling, (b) at least one activator of Sonic hedgehog (SHH) signaling, and (c) at least one activator of wingless (Wnt) signaling; and culturing said cells in the presence of said modulators for a period of time sufficient to provide a cell composition comprising said FOXA2$^+$/LMX1$^+$ cells. In some preferred embodiments, the LMX1 is LIM homeobox transcription factor 1 alpha (LMX1A). In some embodiments, the inhibitor of SMAD signaling is a BMP inhibitor such as, e.g., LDN-193189 (e.g., at a concentration of from about 0.2 µM to about 4 µM, more preferably greater than 0.2 µM to about 4 µM, about 1 µM, 2 µM, 3 µM, 4 µM, or any range derivable therein), dorsomorphin, DMH-1, or noggin. As shown in the below examples, increased concentrations (e.g., 2 µM as compared to 0.2 µM) of LDN-193189 resulted in improved differentiation of iPS cells into FOXA2$^+$/LMX1$^+$ cells or dopaminergic neurons. In some embodiments, the BMP inhibitor is LDN-193189. The SMAD signaling inhibitor may be a TGFβ inhibitor (a TGFβ signaling pathway inhibitor) such as, for example, SB431542 (e.g., SB431542 present at a concentration of about 5-100, 20-60, 30-50 µM, or about 40 µM). In some embodiments, the pluripotent cells are cultured with the inhibitor of SMAD on culture days 1-15, 1-16, or 1-17. The pluripotent cells are cultured with the inhibitor of SMAD substantially continuously or on a daily basis for 15, 16, or 17 days. The inhibitor of SMAD may be present at a concentration of about 50-2000, 50-500, 500-2500, or 500-2000 nM, or about 180-240 nM. In some embodiments, the method further comprises contacting the pluripotent cells with a MEK inhibitor. The MEK inhibitor may be PD0325901. In some embodiments, the PD0325901 is present at a concentration of about 0.25-2.5 µM, or about 0.5-1.5 µM. In some embodiments, the MEK inhibitor is contacted to the pluripotent cells for about 1-3 days, or on days 1-3, 2-4, 3-5, or on days 1, 2, 3, 4, or 5 after initiation of contact with the inhibitor of SMAD signaling (e.g., the contacting may be done for about 72 hours starting on differentiation day 2 or day 3). The MEK inhibitor may be contacted to the pluripotent cells from about 48 to about 72 hours, 24-96 hours, or 24-48 hours after initiation of contact with the inhibitor of SMAD signaling. In some embodiments, the MEK inhibitor is contacted to the pluripotent cells on a daily or substantially continual basis for about 3-4 days beginning about 1-2 days after initiation of contact with the inhibitor of SMAD signaling. In some embodiments, the MEK inhibitor is contacted to the pluripotent cells on days 2-5, days 3-6, or days 3-5 after initiation of contact with the inhibitor of SMAD signaling on day 1. The activator of Wnt signaling may be a GSK3 inhibitor such as, e.g., CHIR99021. The CHIR99021 may be present at a concentration of about 0.5-3 µM or at concentration of from greater than about 1.25 µM to about 2 µM (e.g., about 1.5-2.0 µM, about 1.55-1.75 µM, or about 1.55, 1.65, 1.75 µM, or any range derivable therein; and in some embodiments, higher concentrations may be used, e.g., 4-7 µM or 6 µM on days 9-17 or 11-17 after initiation of contact with the inhibitor of SMAD signaling on day 1). In some embodiments, the activator of Wnt signaling is contacted to the pluripotent cells 1-3 days after initiation of contact with the inhibitor of SMAD signaling. The activator of Wnt signaling may be contacted to the pluripotent cells 12-48 hours or 24-48 hours after initiation of contact with the inhibitor of SMAD signaling. The pluripotent cells are cultured with the activator of Wnt signaling substantially continuously or on a daily basis for 10, 11, 12, 13, 14, 15, or about 16 days. The activator of Wnt signaling may be contacted to the pluripotent cells on days 2-17 after initiation of contact with the inhibitor of SMAD signaling on day 1. In some embodiments, the activator of SHH signaling is purmorphamine, C25II Shh, or C24II Shh. In some embodiments, C25II Shh may be used instead of or in combination with C24II Shh. The method may further comprise contacting the pluripotent cells with two activators of SHH signaling such as, e.g., purmorphamine and C25II Shh. In some embodiments, the at least one activator of SHH signaling is contacted to the pluripotent cells on the same day as initiation of contact with the inhibitor of SMAD signaling or within 24-48 hours after initiation of contact with the inhibitor of SMAD signaling. In some embodiments, the at least one activator of SHH signaling is contacted to the pluripotent cells on days 1-7 with or after initiation of contact with the inhibitor of SMAD signaling on day 1.

In some embodiments, the method further comprises contacting the pluripotent cells with FGF-8. The FGF-8 may be FGF-8a or FGF-8b; preferably, the FGF-8 is not FGF-8f. In some embodiments, the FGF-8 is not contacted to the pluripotent cells on the same day as the initiation of contact with the inhibitor of SMAD signaling. The FGF-8 may be contacted with the pluripotent cells on days 9-17 or 11-17 after initiation of contact with the inhibitor of SMAD signaling on day 1. The FGF-8 may be present at a concentration of about 25-500 ng/mL, 25-250 ng/mL, 50-150, 50-200 ng/mL, or 25, 50, 75, 100, 125, 150, 200, 225, 250, or 275 ng/mL, or any range derivable therein. In some embodiments, including FGF-8 can improve the viability of the cells and promote expression of the desired marker Engrailed-1 (En-1). The pluripotent cells may comprise an antibiotic resistance transgene under the control of a neuronal promoter. The method may further comprise selecting for neural cells or midbrain DA neurons derived from the pluripotent cells by contacting cells with an antibiotic, a chemotherapeutic, a DNA crosslinker, a DNA synthesis inhibitor, or a mitotic inhibitor, e.g., to kill dividing cells that may be present in a culture of cells comprising the neural cells or midbrain DA neurons. The method may further comprise contacting the pluripotent cells with an antibiotic (e.g., G418 (geneticin)) or a chemotherapeutic (e.g., mitomycin C). In some embodiments, the mitomycin C is contacted with the pluripotent cells on days 27, 28, 28, and/or 29 after initiation of contact with the inhibitor of SMAD signaling on day 1. The method may further comprise culturing or incubating the pluripotent cells in a media comprising a ROCK inhibitor prior to initiation of contact with the inhibitor of SMAD signaling. The method may further comprise contacting the pluripotent cells with blebbistatin. For example, the blebbistatin is contacted with the cells on day 5 and day 17 of differentiation.

In some embodiments, about at least 40%, at least 60%, at least 80%, or at least 85% of cells differentiate and express both FOXA2 and LMX1 (such as LMX1A). In some embodiments, about at least 30%, at least 40%, at least 50%, at least 60%, or at least 70% of cells differentiate and express both FOXA2 and tyrosine hydroxylase (TH). The differentiated cells expressing FOXA2 and LMX1 (such as LMX1A), or FOXA2 and TH, may further express at least one marker selected from the group consisting of orthodenticle homeobox 2 (OTX2), nuclear receptor related 1 protein (NURR1), Neuron-specific class III beta-tubulin (Tuj 1), TTF3, paired-like homeodomain 3 (PITX3), achaete-scute complex (ASCL), early B-cell factor 1 (EBF-1), early B-cell factor 3 (EBF-3), transthyretin (TTR), synapsin, dopamine transporter (DAT), and G-protein coupled, inwardly rectifying potassium channel (Kir3.2/GIRK2), CD142, DCSM1, CD63 and CD99. In some embodiments, the method further comprises incubating human pluripotent cells in the presence of an endonuclease such as, e.g., Benzonase® or DNase I. In some preferred embodiments, the endonuclease is a human endonuclease. The Benzonase® or DNase I may be present at 100 U/mL. In some embodiments, the human pluripotent cells are incubated in the presence of an endonuclease or DNase on at least one of days 4-6 after initiation of contact with the inhibitor of SMAD signaling on day 1. In some embodiments, the human pluripotent cells are incubated in the presence of an endonuclease or DNase on day 5 after initiation of contact with the inhibitor of SMAD signaling on day 1.

Another aspect of the present invention relates to a culture of midbrain dopaminergic (DA) neurons generated by a method of the present invention or as described above. The culture may be comprised in a container means. The neurons may be comprised in a pharmaceutical preparation such as, e.g., a pharmaceutical preparation formulated for injection.

Yet another aspect of the present invention relates to a method of treating a disease in a mammalian subject comprising administering to the subject a therapeutically effective amount of the culture of the present invention or as described above. The mammalian subject may be a human. The disease may be a disease of the central nervous system (CNS). In some embodiments, the disease is Parkinson's disease (PD) or a Parkinson-plus syndrome (PPS). The culture may comprise dopaminergic neurons that are not fully differentiated or are at day 16, 17, 18, 19, 20, 21, 22, 23, 24, or 25 of differentiation (e.g., day 17-24 of differentiation). In some embodiments, the culture comprises a hyaluronic acid matrix. As shown in the examples, advantages have been observed for administering cells that are at an intermediate stage of differentiation (e.g., dopaminergic neurons that are not fully differentiated) are administered to a mammalian subject.

Another aspect of the present invention relates to a method of screening a test compound comprising: (a) contacting the test subject with cells differentiated by a method of the present invention or as described above, and (b) measuring the function, physiology, or viability of the cells. In some embodiments, said measuring comprises testing for a toxicological response or an altered electrophysiological response of the cells. In some embodiments, the cells are midbrain dopaminergic (DA) cells.

Additional conditions and methods that may be used in combination with the present invention may be found, e.g., in U.S. 2015/0265652, U.S. 2015/0010514, and WO2013/067362, which are incorporated by reference herein in their entirety. Additional methods for purifying or promoting differentiation of pluripotent cells into neuronal or midbrain DA neurons that may be used in combination with the present invention include, e.g., Kirkeby et al. (2012), Kriks, et al. (2011); Chung, et al. (2011), Xi et al. (2012); Young et al. (2014); Jaeger et al. (2011), Jiang et al. (2012), and US2016/0177260.

As used herein, the "differentiation day" refers to the day of incubation of cells in a media, wherein initiation of exposure of pluripotent cells to a differentiation media on day 1. In some preferred embodiments, the differentiation media on day 1 includes a single SMAD inhibitor. Prior to incubation or culture in a differentiation media, cells may be incubated, e.g., for 1, 2, or 3 days prior to incubation in the differentiation media (i.e., on day 0, day −1, and/or day −2) in a medium comprising or consisting of Essential 8™ Basal Medium and Essential 8™ Supplement (Thermo Fisher Scientific; Waltham, Mass.), optionally with the addition of a ROCK inhibitor (e.g., inclusion of about 0.25-5 µM, 0.5, 0.75, 1, 1.25, 1.5, 2, 3, 4, or any range derivable therein of H1152, e.g., on day −2), and/or blebbestatin (e.g., at a concentration of about 0.1-20 µM, more preferably about 1.25-5 µM, or about 2.5 µM).

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 4A-C: FIG. 4A, Purification of neurons by selecting for non-proliferating cells. FIG. 4B, The functionality of mDA neurons to secrete dopamine after MMC selection.

FIG. 4C, No outgrowth of proliferating cells was observed after MMC selection, even after extended post-thaw culturing.

FIG. 6: Post-thaw characterization mDA neurons made from Line K (iPS cell line 21534.101) after cryopreservation and thawing.

DESCRIPTION OF ILLUSTRATIVE EMBODIMENTS

Figure 1:
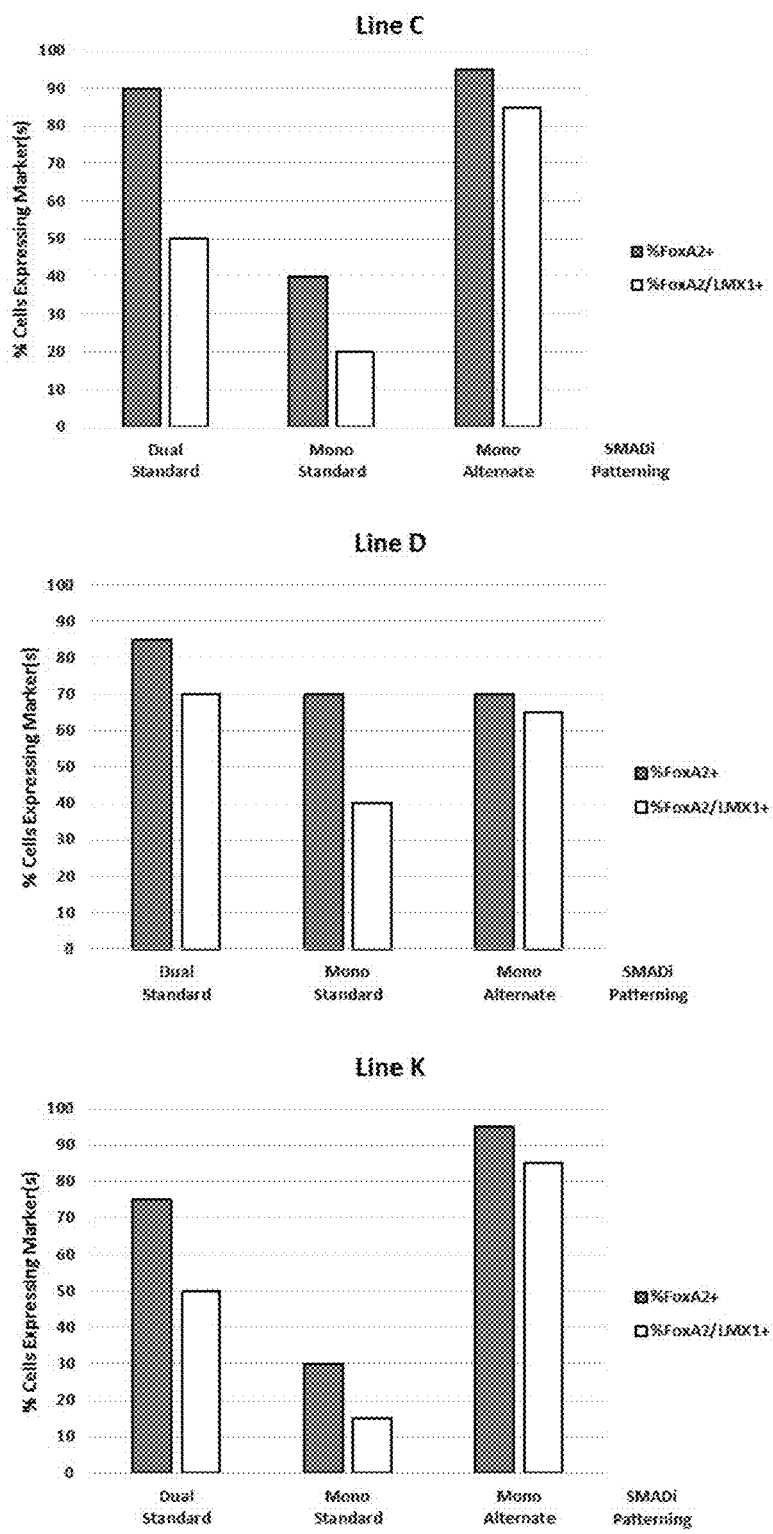
FIG. 1: The patterning of midbrain dopaminergic (mDA) progenitors from three different iPSC lines was evaluated on process day 17 by measuring the proportion of total cells expressing FoxA2 (by flow cytometry) or co-expressing FoxA2 and Lmx1 (by ICC).

In some aspects, the present invention overcomes limitations in the prior art by providing compositions and methods for differentiation of pluripotent cells, such as induced pluripotent stem cells, into neuronal precursor cells or neurons, such as midbrain dopaminergic cells. The methods may involve differentiating the pluripotent cells in the presence of a single SMAD inhibitor ("mono-SMAD inhibition"). Such methods may benefit from advantages of using a single SMAD inhibitor (e.g., reduced cost, a simplified or more minimal methodology, etc.), as compared to previous methods that require the use of two or more SMAD inhibitors.

I. Definitions

"Pluripotency" or "pluripotent" refers to a stem cell or undifferentiated cell that has the potential to differentiate into all cells constituting one or more tissues or organs, for example, any of the three germ layers: endoderm (interior stomach lining, gastrointestinal tract, the lungs), mesoderm (muscle, bone, blood, urogenital), or ectoderm (epidermal tissues and nervous system).

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by introducing or contacting with reprogramming factors.

"Embryonic stem (ES) cells" are pluripotent stem cells derived from early embryos.

"Adherent culture," refers to a culture in which cells, or aggregates of cells, are attached to a surface.

"Suspension culture," refers to a culture in which cells, or aggregates of cells, multiply while suspended in liquid medium.

"Essentially free" of an externally added component refers to a medium that does not have, or that have essentially none of, the specified component from a source other than the cells in the medium. "Essentially free" of externally added growth factors or signaling inhibitors, such as TGFβ, bFGF, TGFβ superfamily signaling inhibitors, etc., may mean a minimal amount or an undetectable amount of the externally added component. For example, a medium or environment essentially free of TGFβ or bFGF can contain less than 5, 4, 3, 2, 1, 0.9, 0.8, 0.7, 0.6, 0.5, 0.4, 0.3, 0.2, 0.1, 0.01, 0.001 ng/mL or any range derivable therein. For example, a medium or environment essentially free of signaling inhibitors can contain less than 0.2, 0.1, 0.09, 0.08, 0.07, 0.06, 0.05, 0.04, 0.03, 0.02, 0.01, 0.005, 0.001 µM, or any range derivable therein.

"Differentiation" is a process by which a less specialized cell forms progeny of at least a new cell type which is more specialized.

The term "aggregate promoting medium" means any medium that enhances the aggregate formation of cells without any restriction as to the mode of action.

The term "aggregates," i.e., embryoid bodies, refers to homogeneous or heterogeneous clusters of cells comprising differentiated cells, partly differentiated cells and/or pluripotent stem cells cultured in suspension.

"Neurons" or "neural cells" or "neural cell types" or "neural lineage" may include any neuron lineage cells, and can be taken to refer to cells at any stage of neuronal ontogeny without any restriction, unless otherwise specified. For example, neurons may include both neuron precursor cells, mature neurons and neural cell types such as astrocytes.

A "gene," "polynucleotide," "coding region," "sequence," "segment," or "fragment," which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "transgene," refers to a gene, nucleic acid, or polynucleotide which has been introduced into the cell or organism by artificial or natural means, such as an exogenous nucleic acid. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

II. SMAD Inhibitors for Mono-SMAD Inhibition

In some aspects, either a single BMP signaling inhibitor or a single TGF-β signaling inhibitor is used to inhibit SMAD signaling in methods to convert pluripotent cells (e.g., iPS cells, ES cells) into neuronal cells such as midbrain dopaminergic cells. For example, in some aspects, pluripotent cells are converted into a population of neuronal cells comprising midbrain DA neurons, wherein the differentiation occurs in a media comprising a single BMP signaling inhibitor. In some embodiments, the BMP inhibitor is LDN-193189, dorsomorphin, or DMH-1. Non-limiting examples of inhibitors of BMP signaling include dorsomorphin, dominant-negative BMP, truncated BMP receptor, soluble BMP receptors, BMP receptor-Fc chimeras, noggin, LDN-193189, follistatin, chordin, gremlin, cerberus/DAN family proteins, ventropin, high dose activin, and amnionless. In some embodiments, a nucleic acid, antisense, RNAi, siRNA, or other genetic method may be used for inhibiting BMP signaling. As used herein, a BMP signaling inhibitor may be referred to simply as a "BMP inhibitor." The BMP inhibitor may be included in the differentiation media on days 1, 2, 3, 4, 5, 6, 7, 8, 9, 10, 11, 12, 13, 14, 15, 16, and/or day 17 of differentiation, or any range derivable therein (e.g., days 1-17, 1-16, 1-15, 2-15, etc.). In some embodiments, the BMP inhibitor is included in the differentiation media on all of days 1-17 of differentiation. Nonetheless, it is anticipated that it may be possible to exclude the BMP inhibitor from the differentiation media at certain times, e.g., on 1, 2, or 3 of the above days. In some embodiments, the BMP inhibitor is optionally not included in the differentiation media on days 11-17, and in some preferred embodiments the BMP inhibitor is included in the differentiation media on days 1-10.

In some embodiments, the BMP inhibitor is LDN-193189, dorsomorphin, DMH-1, or noggin. For example, cells can be cultured in a media comprising about 1-2500, 1-2000, or 1-1,000 nM LDN-193189 (e.g., from about 10 to 500, 50 to 500, 50 to 300, 50, 100, 150, 200, 250, 300, 500, 750, 1000, 1250, 1500, 1750, 2000, 2250, or about 2500 nM LDN-193189, or any range derivable therein). In some embodiments, cells can be cultured in a media comprising about 0.1 to 10 µM dorsomorphin (e.g., from about 0.1 to 10, 0.5 to 7.5, 0.75 to 5, 0.5 to 3, 1 to 3, 0.25, 0.5, 0.75, 1, 1.25, 1.5, 1.55, 1.6, 1.65, 1.7, 1.75, 2, 2.25, 2.5, 2.75, 3, or about 2 µM dorsomorphin, or any range derivable therein). In some embodiments, cells can be cultured in a media comprising about 1 µM DMH-1 (e.g., about 0.2-8, 0.5-2, or about 1 µM DMH-1, or any range derivable therein). As shown in the below examples, LDN-193189, dorsomorphin, and DMH-1 were all successfully used in mono-SMAD inhibition methods to produce midbrain dopaminergic neurons from iPS cells.

In some aspects, a TGFβ inhibitor may be used to inhibit SMAD as a mono-SMAD inhibitor to generate midbrain dopaminergic neurons from pluripotent cells such as iPS cells. For example, in some embodiments, the differentiation media comprises at least a first TGFβ signaling inhibitor. Non-limiting examples of inhibitors of TGFβ signaling include A-83-01, GW6604, IN-1130, Ki26894, LY2157299, LY364947 (HTS-466284), A-83-01, LY550410, LY573636, LY580276, NPC-30345, SB-431542, SB-505124, SD-093, Sml6, SM305, SX-007, Antp-Sm2A, and LY2109761. For instance, the TGFβ inhibitor in a differentiation media may be SB431542. In some aspects, cells are cultured in a media comprising about 0.1 to 100 µM SB431542 (e.g., between about 1 to 100, 10 to 80, 15 to 60, 20-50, or about 40 µM SB431542). As used herein, a TGFβ signaling inhibitor, including a TGFβ receptor inhibitor, may be referred to simply as a "TGFβ inhibitor." In some embodiments, a TGFβ inhibitor is not included in the differentiation media. In some embodiments, a TGFβ inhibitor (e.g., SB431542) be included in a differentiation media on days 1-3, or 1, 2, 3, and/or day 4 as the mono-SMAD inhibitor. As shown in the below examples, in some embodiments, a BMP inhibitor is used as the mono-SMAD inhibitor, since as these compounds were observed to produce superior differentiation of pluripotent cells into midbrain DA neurons, as compared to use of a TGFβ inhibitor.

III. Inclusion of MEK Inhibitor

In some aspects, a MEK inhibitor is included in a differentiation media, e.g., in combination with the BMP inhibitor or mono-SMAD inhibitor to produce midbrain dopaminergic neurons from pluripotent cells such as iPS cells. In some embodiments, the MEK inhibitor is PD0325901. Non-limiting examples of MEK inhibitors that could be used according to the embodiments include PD0325901, trametinib (GSK1120212), selumetinib (AZD6244), pimasertib (AS-703026), MEK162, cobimetinib, PD184352, PD173074, BIX 02189, AZD8330 and PD98059. For example, in some embodiments, the method comprises culturing the cells in the presence of between about 0.1 and 10 µM (e.g., between about 0.1 and 5; 0.5 and 3 or 0.5 and 1.5 µM) of the MEK inhibitor, such as PD0325901. In some embodiments, cells are contacted with the MEK inhibitor (e.g., PD0325901) on day 3, 4, 5, or days 3-5 of the differentiation.

Thus, in certain aspects, differentiating the cells comprises culturing a population of pluripotent cells in a media comprising a BMP inhibitor; an activator of Sonic hedgehog (SHH) signaling; an activator of Wnt signaling, a MEK inhibitor or a combination of the foregoing, wherein the media does not containing exogenously added FGF8b. In some instances, a TGFβ inhibitor may be used instead of a BMP inhibitor. In still further aspects, a method of the embodiments does not comprise purification of cells using a DA-specific marker. In some aspects, the pluripotent cells, comprise resistance gene under the control of a neuronal promoter that may be used to for the purification of neuronal cells (e.g., neuronal cells expressing an antibiotic resistance gene will survive exposure to the antibiotic, whereas non-neuronal cells will die).

In some embodiments, an enriched population of midbrain DA neurons may be produced by a method comprising: obtaining a population of pluripotent cells; differentiating the cells into a neural lineage cell population in a medium comprising a MEK inhibitor (e.g., PD0325901), wherein the medium does not contain exogenously added FGF8b on day 1 of the differentiation; and further differentiating cells of the neural lineage cell population to provide an enriched population of midbrain DA neurons. As described herein, the inventors have observed that, in some instances, inclusion of FGF8 (e.g., FGF8b) in the differentiation media on day 1 can, in some instances, impede or prevent differentiation of the cells into midbrain DA neurons. In some embodiments, FGF8 may optionally be included in a differentiation media on later days of differentiation such as, e.g., days 9, 10, 11, 12, 13, 14, 15, 16, 17, or any range derivable therein, e.g., preferably wherein contact of pluripotent cells is initiated with the single SMAD inhibitor in a differentiation media on day 1.

IV. Inclusion of Wnt Activator or GSK Inhibitor

In some aspects, a Wnt activator (e.g., a GSK3 inhibitor) is included in a differentiation media, e.g., in combination with the BMP inhibitor or mono-SMAD inhibitor to generate midbrain dopaminergic neurons from pluripotent cells such as iPS cells. In some embodiments, pluripotent cells into a population of neuronal cells comprising midbrain DA neurons, wherein the differentiation is in a media comprising at least a first activator of Wnt signaling.

A variety of Wnt activators or GSK3 inhibitors may be used in various aspects of the present invention. For example, the activator of WNT signaling can be a glycogen synthase kinase 3 (GSK3) inhibitor. Non-limiting examples of GSK3 inhibitors include NP031112, TWS119, SB216763, CHIR-98014, AZD2858, AZD1080, SB415286, LY2090314 and CHIR99021. In some embodiments, pluripotent cells are contacted with a single SMAD inhibitor that is not SB415286. In some embodiments, the activator of Wnt signaling is CHIR99021. Thus, in some aspects, a culture media for use according to the embodiments comprises from about 0.1 to about 10 μM CHIR99021 (e.g., between about 0.1 to 5, 0.5 to 5, 0.5 to 3, from greater than about 1.25 to 2.25, about 1.25, 1.5, 1.55, 1.65, 1.7, 1.75, 1.8, 1.9, 2.0, or about 1.75 μM CHIR99021, or any range derivable therein).

In some preferred embodiments, the Wnt activator (e.g., GSK3 inhibitor) is optionally not included in the differentiation media on day 1 of differentiation. In some embodiments, the Wnt activator or GSK inhibitor (e.g., CHR99021) is included in the differentiation media on days 2, 3, 4, 5, 6, 7, 8, 9, 10, 11, 12, 13, 14, 15, 16, and/or day 17, or any combination or all of these days. For example, in some embodiments, the Wnt activator or GSK inhibitor is included in the differentiation media on days 2-17 or days 3-17.

V. Sonic Hedgehog Activator

In some aspects, an activator of Sonic hedgehog (SHH) signaling is included in a differentiation media, e.g., in combination with the BMP inhibitor or mono-SMAD inhibitor to generate midbrain dopaminergic neurons from pluripotent cells such as iPS cells. In some embodiments, the Sonic Hedgehog activator is Sonic Hedgehog (Shh) or a mutant Shh. The Shh may be, e.g., a human or mouse protein or it may be derived from a human or mouse Shh. For example, in some embodiments, the Shh is a mutant mouse Shh protein such as mouse C25II Shh or human C24II Shh. In some embodiments, the differentiation media comprises both Shh (e.g., C25II Shh) and a small molecule activator of SHH such as, e.g., purmorphamine. Without wishing to be bound by any theory, the Shh and/or activator of Sonic Hedgehog may promote neural floor plate differentiation.

In some embodiments, midbrain DA neurons are generated from pluripotent cells by a method comprising culturing the pluripotent cells in a media comprising at least a first activator of SHH signaling. For example, the activator of SHH signaling can be a recombinant SHH polypeptide (or a portion thereof) or a small molecule activator. In certain aspects, the activator of SHH may be Shh C25II, purmorphamine or a purmorphamine analogue (e.g., a Smoothened agonist, such as SAG-1 or 3-chloro-N-[(1r,4r)-4-(methylamino)cyclohexyl]-N-[3-(pyridin-4-yl)benzyl]benzo[b]thiophene-2-carboxamide). Thus, in certain aspects, a culture media for use according to the embodiments comprises about 0.1 to 10 μM purmorphamine (e.g., between about 0.1 to 20, 0.5 to 10, 0.5 to 5 or about 2 μM purmorphamine). In further aspects, a culture media comprises about 1 to 1,000 ng/ml Shh C25II (e.g., about 10 to 1,000, 10 to 500, 50 to 500 or about 100 ng/ml Shh C25II). In some embodiments, the activator of SHH signaling includes both Shh C25II and purmorphamine. For example, cells may be cultured in a media comprising about 0.1 to 10 μM purmorphamine and about 1 to 1,000 ng/ml Shh C25II. The SHH activator(s) (e.g., Shh C25II and purmorphamine) may be included in a differentiation media on days 1, 2, 3, 4, 5, 6, and/or 7. In some embodiments, the SHH activators are excluded from the differentiation media on day 1. For example, in various embodiments, the SHH activator(s) are included in the differentiation media on days 1-6 or 2-7.

Thus, in certain aspects, pluripotent cells may be cultured in a differentiation for 1-6 days in an adherent culture system with a DMEM/F12 media comprising B27 supplement, 1-3000 or 1-1000 nM LDN-193189 (or 0.1 to 100 μM SB431542), 0.1 to 50 μM purmorphamine, 1 to 1,000 ng/ml Shh C25II, and 0.1 to 10 μM CHIR99021. In one aspect, the media may comprise B27 supplement, 200 nM LDN-193189 (or 10 μM SB431542), 2 μM purmorphamine, 100 ng/ml Shh C25II, and 1.25 μM CHIR99021. In some embodiments, the MEK inhibitor is included in the media after 1-2 days (e.g., the MEK inhibitor is included on days 2-4, or days 2, 3, and/or 4 of differentiation).

VI. Sources of Pluripotent Stem Cells

Pluripotent stem cells may be used in present methods for neural induction of pluripotent stem cells. Methods and compositions are disclosed herein that may be used, e.g., to improve the neural differentiation efficiency by optimizing media components and/or selection of the desired midbrain DA neurons produced by the differentiation protocol.

The term "pluripotent stem cell" or "pluripotent cell" refers to a cell capable of giving rise to cells of all three germinal layers, that is, endoderm, mesoderm and ectoderm. Although in theory a pluripotent stem cell can differentiate into any cell of the body, the experimental determination of pluripotency is typically based on differentiation of a pluripotent cell into several cell types of each germinal layer. In some embodiments, the pluripotent stem cell is an embryonic stem (ES) cell derived from the inner cell mass of a blastocyst. In other embodiments, the pluripotent stem cell is an induced pluripotent stem cell derived by reprogramming somatic cells. In some embodiments, the pluripotent stem cell is an embryonic stem cell derived by somatic cell nuclear transfer. The pluripotent stem cell may be obtained or derived from a healthy subject (e.g., a healthy human) or a subject with a disease (e.g., a neurodegenerative disease, Parkinson's disease, etc.).

A. Embryonic Stem Cells

Embryonic stem (ES) cells are pluripotent cells derived from the inner cell mass of a blastocyst. ES cells can be isolated by removing the outer trophectoderm layer of a developing embryo, then culturing the inner mass cells on a feeder layer of non-growing cells. Under appropriate conditions, colonies of proliferating, undifferentiated ES cells are produced. The colonies can be removed, dissociated into individual cells, and then replated on a fresh feeder layer. The replated cells can continue to proliferate, producing new colonies of undifferentiated ES cells. The new colonies can then be removed, dissociated, replated again and allowed to grow. This process of "subculturing" or "passaging" undifferentiated ES cells can be repeated a number of times to produce cell lines containing undifferentiated ES cells (e.g., as described in U.S. Pat. Nos. 5,843,780; 6,200,806; 7,029, 913). A "primary cell culture" is a culture of cells directly obtained from a tissue such as, e.g., the inner cell mass of a blastocyst. A "subculture" is any culture derived from the primary cell culture.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be obtained from blastocysts using previously described methods (Thomson et al., 1995; Thomson et al., 1998; Thomson and Marshall, 1998; Reubinoff et al, 2000.) In one method, day-5 human blastocysts are exposed to rabbit anti-human spleen cell antiserum, and then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as Matrigel™ or laminin in the presence of "conditioned" medium containing basic fibroblast growth factor (Xu et al., 2001). The medium can be previously conditioned by coculturing with fibroblasts.

Methods for the isolation of rhesus monkey and common marmoset ES cells are also known (Thomson, and Marshall, 1998; Thomson et al., 1995; Thomson and Odorico, 2000).

Another source of ES cells are established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13 and H14 were established by Thomson et al. (2000). In addition, subclones H9.1 and H9.2 of the H9 line have been developed. It is anticipated that virtually any ES or stem cell line known in the art may be used with the present invention, such as, e.g., those described in Yu and Thomson, 2008, which is incorporated herein by reference.

The source of ES cells for use in aspects of the present invention include a blastocyst, cells derived from culturing the inner cell mass of a blastocyst, and cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

B. Induced Pluripotent Stem Cells

Induced pluripotent stem (iPS) cells are cells which have the characteristics of ES cells but are obtained by the reprogramming of differentiated somatic cells. Induced pluripotent stem cells have been obtained by various methods. In one method, adult human dermal fibroblasts are transfected with transcription factors Oct4, Sox2, c-Myc and Klf4 using retroviral transduction (Takahashi et al., 2006, 2007). The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF. In some preferred embodiments, the iPS cells are human iPS cells.

Based on cell characteristics, cells of the ES cell-like colonies are induced pluripotent stem cells. The induced pluripotent stem cells are morphologically similar to human ES cells, and express various human ES cell markers. Also, when grown under conditions that are known to result in differentiation of human ES cells, the induced pluripotent stem cells differentiate accordingly. For example, the induced pluripotent stem cells can differentiate into cells having neuronal structures and neuronal markers. It is anticipated that virtually any iPS cell or cell lines may be used with the present invention, including, e.g., those described in Yu and Thomson, 2008.

In another method, human fetal or newborn fibroblasts are transfected with four genes, Oct4, Sox2, Nanog and Lin28 using lentivirus transduction (Yu et al., 2007). At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage and gut epithelium after injection into mice.

Methods of preparing induced pluripotent stem cells from mouse cells are also known (Takahashi and Yamanaka, 2006). Induction of iPS cells typically requires the expression of or exposure to at least one member from the Sox family and at least one member from the Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog and, optionally, Lin-28; or comprising Sox-2, Oct4, Klf and, optionally, c-Myc.

IPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of embryonic stem cells can be confirmed by, e.g., by injecting approximately 0.5-10×10$^6$ cells into the rear leg muscles of 8-12 week old male SCID mice. Teratomas develop that demonstrate at least one cell type of each of the three germ layers.

In certain aspects of the present invention, iPS cells are made from reprogramming somatic cells using reprogramming factors comprising an Oct family member and a Sox family member, such as Oct4 and Sox2 in combination with Klf or Nanog, e.g., as described above. The somatic cell may be any somatic cell that can be induced to pluripotency such as, e.g., a fibroblast, a keratinocyte, a hematopoietic cell, a mesenchymal cell, a liver cell, a stomach cell, or a P cell. In some embodiments, T cells may also be used as source of somatic cells for reprogramming (e.g., see WO 2010/141801, incorporated herein by reference).

Reprogramming factors may be expressed from expression cassettes comprised in one or more vectors, such as an integrating vector, a chromosomally non-integrating RNA viral vector (see U.S. application Ser. No. 13/054,022, incorporated herein by reference) or an episomal vector, such as an EBV element-based system (e.g., see WO 2009/149233, incorporated herein by reference; Yu et al., 2009). In a further aspect, reprogramming proteins or RNA (such as mRNA or miRNA) could be introduced directly into somatic cells by protein or RNA transfection (Yakubov et al., 2010).

C. Embryonic Stem Cells Derived by Somatic Cell Nuclear Transfer

Pluripotent stem cells can be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts are introduced into the cytoplasm of spindle-free, mature metaphase II oocyte by electrofusion (Byrne et al., 2007). The fused oocytes are activated by exposure to ionomycin, and then incubated until the blastocyst stage. The inner cell mass of selected blastocysts are then cultured to produce embryonic stem cell lines. The embryonic stem cell lines can show normal ES cell morphology, express various ES cell markers, and differentiate into multiple cell types both in vitro and in vivo. As used herein, the term "ES cells" refers to embryonic stem cells derived from embryos containing fertilized nuclei. ES cells are distinguished from embryonic stem cells produced by nuclear transfer, which are referred to as "embryonic stem cells derived by somatic cell nuclear transfer."

VII. Medium for Differentiation

A differentiation medium according to certain aspects of the present invention can be prepared using a medium to be used for culturing animal cells as its basal medium. In some embodiments, a differentiation medium is used to differentiate pluripotent cells into midbrain dopaminergic neurons using only a single BMP inhibitor or a single TGF-beta inhibitor. For example, a differentiation medium used to promote differentiation of pluripotent cells (e.g., into midbrain dopaminergic cells) may comprise a single BMP inhibitor (such as LDN-193189 or dorsomorphin; e.g., on days 1-17 of differentiation; an activator of Sonic hedgehog (SHH) signaling (such as purmorphamine, human C25II SHH, or mouse C24II SHH; e.g., on days 1-6, 2-7, or 1-7); an activator of Wnt signaling (such as a GSK inhibitor, e.g., CHIR99021; e.g., on days 2-17 or 3-17) and/or a MEK inhibitor (such as PD0325901; e.g., on days 2-4 or 3-5). In some embodiments, a single TGFβ inhibitor (such as SB-431542; e.g., on days 1-4) may be used instead of the single BMP inhibitor; however, as shown in the below examples, use of a single BMP inhibitor was observed to result in superior differentiation of cells into FOXA2$^+$/LMX1A$^+$, cells as compared to use of a single TGF-β inhibitor. In some embodiments, FGF-8 (e.g., FGF-8b) is not included in differentiation media on the first day or days 1, 2, 3, 4, 5, 6, 7, 8, 9, or 10, or any combination thereof (e.g., days 1-8); for example, in some embodiments, FGF-8 is included in the differentiation media on days 9, 10, 11, 12, 13, 14, 15, 16, and 17, or any combination thereof. In various embodiments, the differentiation media may contain TGFβ and bFGF, or, alternately, the differentiation media may be essentially free of TGFβ and bFGF.

In certain aspects, a method of differentiation according to the embodiments involves passage of cell through a range of media conditions for example cells are cultured in adherent culture in a medium comprising: a single BMP inhibitor (or a TGFβ inhibitor); an activator of Sonic hedgehog (SHH) signaling; and an activator of Wnt signaling;

in suspension in a medium comprising a single BMP inhibitor (or a TGFβ inhibitor); an activator of SHH signaling; and an activator of Wnt signaling, to form cell aggregates;

in adherent culture in a Neurobasal medium comprising B27 supplement, L-glutamine, BDNF, GDNF, TGFβ, ascorbic acid, dibutyryl cAMP, and DAPT, (and, optionally, lacking exogenously added retinol or retinoic acid) for maturation.

As the basal medium, any chemically defined medium, such as Eagle's Basal Medium (BME), BGJb, CMRL 1066, Glasgow MEM, Improved MEM Zinc Option, Iscove's modified Dulbecco's medium (IMDM), Medium 199, Eagle MEM, aMEM, DMEM, Ham, RPMI 1640, and Fischer's media, variations or combinations thereof can be used, wherein TGFβ and bFGF may or may not be included.

In further embodiments, the cell differentiation environment can also contain supplements such as B-27 supplement, an insulin, transferrin, and selenium (ITS) supplement, L-Glutamine, NEAA (non-essential amino acids), P/S (penicillin/streptomycin), N2 supplement (5 μg/mL insulin, 100 μg/mL transferrin, 20 nM progesterone, 30 nM selenium, 100 μM putrescine (Bottenstein, and Sato, 1979 PNAS USA 76, 514-517) and/or β-mercaptoethanol (β-ME). It is contemplated that additional factors may or may not be added, including, but not limited to fibronectin, laminin, heparin, heparin sulfate, retinoic acid.

Growth factors may or may not be added to a differentiation medium. In additional or in place of the factors outlined above, growth factors such as members of the epidermal growth factor family (EGFs), members of the fibroblast growth factor family (FGFs) including FGF2 and/or FGF8, members of the platelet derived growth factor family (PDGFs), transforming growth factor (TGF)/bone morphogenetic protein (BMP)/growth and differentiation factor (GDF) factor family antagonists may be employed at various steps in the process. In some embodiments, FGF-8 is included in a differentiation media as described herein. Other factors that may or may not be added to the differentiation media include molecules that can activate or inactivate signaling through Notch receptor family, including but not limited to proteins of the Delta-like and Jagged families as well as gamma secretase inhibitors and other inhibitors of Notch processing or cleavage such as DAPT. Other growth factors may include members of the insulin like growth factor family (IGF), the wingless related (WNT) factor family, and the hedgehog factor family.

Additional factors may be added in an aggregate formation and/or differentiation medium to promote neural stem/ progenitor proliferation and survival as well as neuron survival and differentiation. These neurotrophic factors include but are not limited to nerve growth factor (NGF), brain derived neurotrophic factor (BDNF), neurotrophin-3 (NT-3), neurotrophin-4/5 (NT-4/5), interleukin-6 (IL-6), ciliary neurotrophic factor (CNTF), leukemia inhibitory factor (LIF), cardiotrophin, members of the transforming growth factor (TGF)/bone morphogenetic protein (BMP)/growth and differentiation factor (GDF) family, the glial derived neurotrophic factor (GDNF) family including but not limited to neurturin, neublastin/artemin, and persephin and factors related to and including hepatocyte growth factor. Neural cultures that are terminally differentiated to form post-mitotic neurons may also contain a mitotic inhibitor or mixture of mitotic inhibitors including but not limited to 5-fluoro 2'-deoxyuridine, Mitomycin C and/or cytosine β-D-arabino-furanoside (Ara-C).

The medium can be a serum-containing or serum-free medium. The serum-free medium may refer to a medium with no unprocessed or unpurified serum and accordingly, can include media with purified blood-derived components or animal tissue-derived components (such as growth factors). From the aspect of preventing contamination with heterogeneous animal-derived components, serum can be derived from the same animal as that of the stem cell(s). In some embodiments, the medium is a defined medium, and the medium does not contain serum or other animal tissue-derived components (such as irradiated mouse fibroblasts or a media has been conditioned with irradiated fibroblast feeder cells).

The medium may contain or may not contain any alternatives to serum. The alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolglycerol, or equivalents thereto. For example, an alternative to serum may be prepared by the method disclosed in International Publication No. 98/30679. Alternatively, commercially available materials can be used for more convenience. The commercially available materials include knockout Serum Replacement (KSR) and Chemically-defined Lipid concentrated (Gibco).

The medium can also contain fatty acids or lipids, amino acids (such as non-essential amino acids), vitamin(s), growth factors, cytokines, antioxidant substances, 2-mercaptoethanol, pyruvic acid, buffering agents, and inorganic salts. The concentration of 2-mercaptoethanol can be, for example, about 0.05 to 1.0 mM, and particularly about 0.1 to 0.5, or 0.01, 0.02, 0.03, 0.04, 0.05, 0.1, 0.2, 0.5, 0.8, 1, 1.5, 2, 2.5, 5, 7.5, 10 mM or any intermediate values, but the concentration is particularly not limited thereto as long as it is appropriate for culturing the stem cell(s).

In certain embodiments, pluripotent stem cells are cultured in a medium prior to aggregate formation to improve neural induction and floor plate patterning (e.g., prior to being dissociated into single cells or small aggregates to induce aggregate formation). In certain embodiments of the invention, the stem cells may be cultured in the absence of feeder cells, feeder cell extracts and/or serum.

B. Culture Conditions

A culture vessel used for culturing the cell(s) can include, but is particularly not limited to: flask, flask for tissue culture, spinner flask, dish, petri dish, dish for tissue culture, multi dish, micro plate, micro-well plate, multi plate, multi-well plate, micro slide, chamber slide, tube, tray, Cell-STACK® Chambers, culture bag, and roller bottle, as long as it is capable of culturing the cells therein. The cells may be cultured in a volume of at least or about 0.2, 0.5, 1, 2, 5, 10, 20, 30, 40, 50, 100, 150, 200, 250, 300, 350, 400, 450, 500, 550, 600, 800, 1000, 1500 mL, or any range derivable therein, depending on the needs of the culture. In a certain embodiment, the culture vessel may be a bioreactor, which may refer to any device or system that supports a biologically active environment. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

The culture vessel surface can be prepared with cellular adhesive or not depending upon the purpose. The cellular adhesive culture vessel can be coated with any substrate for cell adhesion such as extracellular matrix (ECM) to improve the adhesiveness of the vessel surface to the cells. The substrate used for cell adhesion can be any material intended to attach stem cells or feeder cells (if used). Non-limiting substrates for cell adhesion include collagen, gelatin, poly-L-lysine, poly-D-lysine, poly-L-ornithine, laminin, vitronectin, and fibronectin and mixtures thereof, for example, protein mixtures from Engelbreth-Holm-Swarm mouse sarcoma cells (such as Matrigel™ or Geltrex) and lysed cell membrane preparations (Klimanskaya et al., 2005).

Other culturing conditions can be appropriately defined. For example, the culturing temperature can be about 30 to 40° C., for example, at least or about 31, 32, 33, 34, 35, 36, 37, 38, 39° C. but particularly not limited to them. The $CO_2$ concentration can be about 1 to 10%, for example, about 2 to 7%, or any range derivable therein. The oxygen tension can be at least or about 1, 5, 8, 10, 20%, or any range derivable therein.

An adhesion culture may be used in certain aspects. In this case, the cells can be cultured in the presence of feeder cells. In the case where the feeder cells are used in the methods of the present invention, stromal cells such as fetal fibroblasts can be used as feeder cells (for example, refer to; Manipulating the Mouse Embryo A Laboratory Manual (1994); Gene Targeting, A Practical Approach (1993); Martin (1981); Evans et al. (1981); Jainchill et al., (1969); Nakano et al., (1996); Kodama et al. (1982); and International Publication Nos. 01/088100 and 2005/080554).

In other aspects, a suspension culture may be used. A suspension culture may include a suspension culture on carriers (Fernandes et al., 2007) or gel/biopolymer encapsulation (U.S. Patent Publication No. 2007/0116680). The suspension culture of the stem cells means that the stem cells are cultured under non-adherent conditions with respect to the culture vessel or feeder cells (if used) in a medium. The suspension culture of stem cells generally includes a dissociation culture of stem cells and an aggregate suspension culture of stem cells. The dissociation culture of stem cells means that suspended stem cells are cultured, and the dissociation culture of stem cells include those of single stem cells or those of small cell aggregates composed of a plurality of stem cells (for example, about 2 to 400 cells). When the aforementioned dissociation culture is continued, the cultured, dissociated cells form a larger aggregate of stem cells, and thereafter an aggregate suspension culture can be performed. The aggregate suspension culture includes an embryoid culture method (see Keller et al., 1995), and a SFEB (serum-free embryoid body) method (Watanabe et al., 2005); International Publication No. 2005/123902).

C. Culturing of Pluripotent Stem Cells

Methods for preparing and culturing pluripotent stem cells such as ES cells can be found in standard textbooks and reviews in cell biology, tissue culture, and embryology, including teratocarcinomas and embryonic stem cells: Guide to Techniques in Mouse Development (1993); Embryonic Stem Cell Differentiation in vitro (1993); Properties and uses of Embryonic Stem Cells: Prospects for Application to Human Biology and Gene Therapy (1998), all incorporated herein by reference. Standard methods used in tissue culture generally are described in Animal Cell Culture (1987); Gene Transfer Vectors for Mammalian Cells (1987); and Current Protocols in Molecular Biology and Short Protocols in Molecular Biology (1987 & 1995).

After somatic cells are introduced into or contacted with reprogramming factors, these cells may be cultured in a medium sufficient to maintain the pluripotency and the undifferentiated state. Culturing of induced pluripotent stem (iPS) cells can use various medium and techniques developed to culture primate pluripotent stem cells, embryonic stem cells, or iPS cells, for example as described in U.S. Pat. Publication 2007/0238170 and U.S. Pat. Publication 2003/0211603, and U.S. Pat. Publication 2008/0171385, which are hereby incorporated by reference. It is appreciated that additional methods for the culture and maintenance of pluripotent stem cells, as would be known to one of skill, may be used with the present invention.

In certain embodiments, undefined conditions may be used; for example, pluripotent cells may be cultured on fibroblast feeder cells or a medium that has been exposed to fibroblast feeder cells in order to maintain the stem cells in an undifferentiated state. Alternately, pluripotent cells may be cultured and maintained in an essentially undifferentiated state using defined, feeder-independent culture system, such as a TeSR medium (Ludwig et al., 2006a; Ludwig et al., 2006b) or E8 medium (Chen et al., 2011; PCT/US2011/046796). Feeder-independent culture systems and media may be used to culture and maintain pluripotent cells. These approaches allow human pluripotent stem cells to remain in an essentially undifferentiated state without the need for mouse fibroblast "feeder layers." As described herein, various modifications may be made to these methods in order to reduce costs as desired.

Various matrix components may be used in culturing, maintaining, or differentiating human pluripotent stem cells. For example, collagen IV, fibronectin, laminin, and vitronectin in combination may be used to coat a culturing surface as a means of providing a solid support for pluripotent cell growth, as described in Ludwig et al. (2006a; 2006b), which are incorporated by reference in their entirety.

Matrigel™ may also be used to provide a substrate for cell culture and maintenance of human pluripotent stem cells. Matrigel™ is a gelatinous protein mixture secreted by mouse tumor cells and is commercially available from BD Biosciences (New Jersey, USA). This mixture resembles the complex extracellular environment found in many tissues and is used by cell biologists as a substrate for cell culture.

D. Single Cell Passaging

In some embodiments of pluripotent stem cell culturing, once a culture container is full, the colony is split into aggregated cells or even single cells by any method suitable for dissociation, which cells are then placed into new culture containers for passaging. Cell passaging or splitting is a technique that enables cells to survive and grow under cultured conditions for extended periods of time. Cells typically would be passaged when they are about 70%-100% confluent.

Single-cell dissociation of pluripotent stem cells followed by single cell passaging may be used in the present methods with several advantages, like facilitating cell expansion, cell sorting, and defined seeding for differentiation and enabling automatization of culture procedures and clonal expansion. For example, progeny cells clonally derived from a single cell may be homogenous in genetic structure and/or synchronized in cell cycle, which may increase targeted differentiation. Exemplary methods for single cell passaging may be as described in U.S. Pat. Publn. 2008/0171385, which is incorporated herein by reference.

In certain embodiments, pluripotent stem cells may be dissociated into single individual cells, or a combination of single individual cells and small cell clusters comprising 2, 3, 4, 5, 6, 7, 8, 9, 10 cells or more. The dissociation may be achieved by mechanical force, or by a cell dissociation agent, such as a chelating agent, sodium citrate (NaCitrate), or an enzyme, e.g., trypsin, trypsin-EDTA, Accutase, TrypLE Select, or the like. Dissociation of cells may be achieved using chemical separation (e.g., using a chelator or enzyme) and/or mechanical agitation to dissociate cells.

Based on the source of pluripotent stem cells and the need for expansion, the dissociated cells may be transferred individually or in small clusters to new culture containers in a splitting ratio such as at least or about 1:2, 1:4, 1:5, 1:6, 1:8, 1:10, 1:20, 1:40, 1:50, 1:100, 1:150, 1:200, or any range derivable therein. Suspension cell line split ratios may be done on volume of culture cell suspension. The passage interval may be at least or about every 1, 2, 3, 4, 5, 6, 7, 8, 9, 10, 11, 12, 13, 14, 15, 16, 17, 18, 19, 20 days or any range derivable therein. For example, the achievable split ratios for the different enzymatic passaging protocols may be 1:2 every 3-7 days, 1:3 every 4-7 days, and 1:5 to 1:10 approximately every 7 days, 1:50 to 1:100 every 7 days. When high split ratios are used, the passage interval may be extended to at least 12-14 days or any time period without cell loss due to excessive spontaneous differentiation or cell death.

In certain aspects, single cell passaging may be in the presence of a small molecule effective for increasing cloning efficiency and cell survival, such as a ROCK inhibitor or myosin II inhibitor as described above. Such a ROCK inhibitor or myosin II inhibitor, e.g., Y-27632, HA-1077, H-1152, or blebbistatin, may be used at an effective concentration, for example, at least or about 0.02, 0.05, 0.1, 0.2, 0.5, 1, 2, 3, 4, 5, 10, 15, 20, 25, 30, 35, 40, 45, 50 to about 100 µM, or any range derivable therein.

E. Differentiation of Stem Cells

Methods may be provided to improve neural differentiation (in particular midbrain DA differentiation efficiency) efficiency of pluripotent stem cells. Differentiation of pluripotent stem cells can be induced in a variety of manners, such as in attached colonies or by formation of cell aggregates, e.g., in low-attachment environment, wherein those aggregates are referred to as embryoid bodies (EBs). The molecular and cellular morphogenic signals and events within EBs mimic many aspects of the natural ontogeny of such cells in a developing embryo. Methods for directing cells into neuronal differentiation are provided for example in U.S. Publn. No. 2012/0276063, incorporated herein by reference. More detailed and specific protocols for DA neuron differentiation are provided in PCT Publication No. WO2013/067362, incorporated herein by reference.

Embryoid bodies (EBs) are aggregates of cells derived from pluripotent stem cells, such as ES cells or iPS cells, and have been studied for years with mouse embryonic stem cells. In order to recapitulate some of the cues inherent to in vivo differentiation, three-dimensional aggregates (i.e., embryoid bodies) may be generated as an intermediate step. Upon the start of cell aggregation, differentiation may be initiated and the cells may begin to a limited extent to recapitulate embryonic development. Though they cannot form trophectodermal tissue (which includes the placenta), cells of virtually every other type present in the organism can develop. The present invention may further promote neural differentiation following aggregate formation.

Cell aggregation may be imposed by hanging drop, plating upon non-tissue culture treated plates or spinner flasks; either method prevents cells from adhering to a surface to form the typical colony growth. ROCK inhibitors or myosin II inhibitors may be used before, during or after aggregate formation to culture pluripotent stem cells.

Pluripotent stem cells may be seeded into aggregate promotion medium using any method known in the art of cell culture. For example, pluripotent stem cells may be seeded as a single colony or clonal group into aggregate promotion medium, and pluripotent stem cells may also be seeded as essentially individual cells. In some embodiments, pluripotent stem cells are dissociated into essentially individual cells using mechanical or enzymatic methods known in the art. By way of non-limiting example, pluripotent stem cells may be exposed to a proteolytic enzyme which disrupts the connections between cells and the culturing surface and between the cells themselves. Enzymes which may be used to individualize pluripotent stem cells for aggregate formation and differentiation may include, but are not limited to, trypsin, in its various commercial formulations, such as TrypLE, or a mixture of enzymes such as Accutase®. In certain embodiments, pluripotent cells may be added or seeded as essentially individual (or dispersed) cells to a culturing medium for culture formation on a culture surface.

For example, dispersed pluripotent cells may be seeded into a culturing medium. In these embodiments, a culturing surface may be comprised of essentially any material which is compatible with standard aseptic cell culture methods in the art, for example, a non-adherent surface. A culturing surface may additionally comprise a matrix component as described herein. In some embodiments, a matrix component may be applied to a culturing surface before contacting the surface with cells and medium.

Substrates that may be used to induce differentiation such as collagen, fibronectin, vitronectin, laminin, matrigel, and the like. Differentiation can also be induced by leaving the cells in suspension in the presence of a proliferation-inducing growth factor, without reinitiating proliferation (i.e., without dissociating the neurospheres).

In some embodiments, cells are cultured on a fixed substrate in a culture medium. A proliferation-inducing growth factor can then be administered to the cells. The proliferation inducing growth factor can cause the cells to adhere to the substrate (e.g., polyornithine-treated plastic or glass), flatten, and begin to differentiate into different cell types.

V. Non-static Culture

In certain aspects, non-static culture could be used for culturing and differentiation of pluripotent stem cells. The non-static culture can be any culture with cells kept at a controlled moving speed, by using, for example, shaking, rotating, or stirring platforms or culture vessels, particularly large-volume rotating bioreactors. In some embodiments, a rocker table may be used. The agitation may improve circulation of nutrients and cell waste products and also be used to control cell aggregation by providing a more uniform environment. For example, rotary speed may be set to at least or at most about 10, 15, 20, 25, 30, 35, 40, 45, 50, 75, 100 rpm, or any range derivable therein. The incubation period in the non-static culture for pluripotent stem cells, cell aggregates, differentiated stem cells, or progeny cells derived therefrom, may be at least or about 4 hours, 8 hours, 16 hours, or 1, 2, 3, 4, 5, 6 days, or 1, 2, 3, 4, 5, 6, 7 weeks, or any range derivable therein.

VI. Genetic Alteration and Purification of Cells

In some embodiments, pluripotent cells (e.g., pluripotent cells or DA neurons) that have been genetically engineered. A cell is said to be "genetically altered" or "transgenic" when a polynucleotide has been transferred into the cell by any suitable means of artificial manipulation, or where the cell is a progeny of the originally altered cell that has inherited the polynucleotide. In some embodiments, cells may comprise an antibiotic resistance gene, e.g., under the control of a neuronal promoter such as, e.g., the MAP2 promoter. For example, in some embodiments, the marker gene is an antibiotic resistance gene, and neuronal cells may be purified by exposing the cell culture to an antibiotic, thus killing cells that have not differentiated into neuronal cells. For example, cells expressing a neomycin gene under the control of the MAP2 promoter may be exposed to G418 to kill non-neuronal cells. Additional methods that may be used with the present invention are described in U.S. patent application Ser. No. 14/664,245, which is incorporated by reference herein without disclaimer in its entirety.

In some embodiments, a population of cells comprising dopaminergic neurons may be purified by exposing the cells to a mitotic inhibitor or chemotherapeutic to kill dividing cells. For example, in some embodiments, a population of cells comprising midbrain DA cells produced by methods of the present invention may be purified by contacting the cells with Mitomycin C to kill dividing cells.

VII. Use of Dopaminergic Neurons

The DA neurons provided by methods and compositions of certain aspects of the invention can be used in a variety of applications. These include but are not limited to transplantation or implantation of the DA neurons in vivo; screening cytotoxic compounds, carcinogens, mutagens growth/regulatory factors, pharmaceutical compounds, etc., in vitro; elucidating the mechanism of neurodegeneration; studying the mechanism by which drugs and/or growth factors operate; gene therapy; and the production of biologically active products, to name but a few.

A. Test Compound Screening

Midbrain DA neurons of this invention can be used to screen for factors (such as solvents, small molecule drugs, peptides, and polynucleotides) or environmental conditions (such as culture conditions or manipulation) that affect the characteristics of DA neurons provided herein.

In some applications, stem cells (differentiated or undifferentiated) are used to screen factors that promote maturation of cells along the neural lineage, or promote proliferation and maintenance of such cells in long-term culture. For example, candidate neural maturation factors or growth factors are tested by adding them to stem cells in different wells, and then determining any phenotypic change that results, according to desirable criteria for further culture and use of the cells.

Particular screening applications of this invention relate to the testing of pharmaceutical compounds in drug research. Standard methods of testing are provided, e.g., in *In vitro Methods in Pharmaceutical Research*, Academic Press, 1997). In certain aspects of the embodiments, cells produced by methods detailed herein may be used as test cells for standard drug screening and toxicity assays (e.g., to identify, confirm, and test for specification of function or for testing delivery of therapeutic molecules to treat cell lineage specific disease), as have been previously performed on primary neurons in short-term culture. Assessment of the activity of candidate pharmaceutical compounds generally involves combining the neurons provided in certain aspects of this invention with the candidate compound, determining any change in the electrophysiology, morphology, marker phenotype, or metabolic activity of the cells that is attributable to the compound (compared with untreated cells or cells treated with an inert compound), and then correlating the effect of the compound with the observed change. The screening may be done either because the compound is designed to have a pharmacological effect on neurons cells, or because a compound designed to have effects elsewhere may have unintended neural side effects. Two or more drugs can be tested in combination (by combining with the cells either simultaneously or sequentially), to detect possible drug-drug interaction effects.

In some applications, compounds are screened initially for potential neurotoxicity. Cytotoxicity can be determined in the first instance by the effect on cell viability, survival, morphology, or leakage of enzymes into the culture medium. More detailed analysis is conducted to determine whether compounds affect cell function (such as neurotransmission) without causing toxicity.

B. Treatment of Diseases of the Central Nervous System

1. Disease of the Central Nervous System

Dopaminergic neurons, such as post-mitotic midbrain DA neurons, can be transplanted to regenerate neural cells in an individual having a disease of the central nervous system (CNS). In some embodiments, midbrain DA neurons produced according to methods of the present invention may be administered to a subject to treat a CNS disease (e.g., administered to the brain or midbrain, such as the caudate nucleus, putamen, or substantia nigra to treat Parkinson's Disease). Such diseases can include, but are not limited to, neurodegenerative diseases, such as parkinsonism.

As used herein, term "parkinsonism" refers to a group of diseases that are all linked to an insufficiency of dopamine in the basal ganglia which is a part of the brain that controls movement. Symptoms include tremor, bradykinesia (extreme slowness of movement), flexed posture, postural instability, and rigidity. A diagnosis of parkinsonism requires the presence of at least two of these symptoms, one of which must be tremor or bradykinesia. The most common form of parkinsonism is idiopathic, or classic, Parkinson's disease (PD), but for a significant minority of diagnoses, about 15 percent of the total, one of the Parkinson's plus syndromes (PPS) may be present. These syndromes also known as atypical parkinsonism, include corticobasal degeneration, Lewy body dementia, multiple systematrophy, and progressive supranuclear palsy. In general, Parkinson's disease involves the malfunction and death of vital nerve cells in the brain primarily in an area of the brain called the substantia nigra. Many of these vital nerve cells make dopamine. When these neurons die off, the amount of dopamine decreases, leaving a person unable to control movement normally. The intestines also have dopamine cells that degenerate in Parkinson's disease patients, and this may be an important causative factor in the gastrointestinal symptoms that are part of the disease. The particular symptoms that an individual experiences can vary from person to person. Primary motor signs of Parkinson's disease include the following: tremor of the hands, arms, legs, jaw and face, bradykinesia or slowness of movement, rigidity or stiffness of the limbs and trunk and postural instability or impaired balance and coordination.

2. Methods for Administering Cells

Stem cells or differentiated cells can be administered to a subject either locally or systemically. Methods for administering DA neurons to a subject are known in the art. If the patient is receiving cells derived from his or her own cells, this is called an autologous transplant; such a transplant has little likelihood of rejection.

Exemplary methods of administering stem cells or differentiated neuronal cells to a subject, particularly a human subject, include injection or transplantation of the cells into target sites (e.g., striatum and/or substantia nigra) in the subject. The stem cells and/or DA neurons can be inserted into a delivery device which facilitates introduction, by injection or transplantation, of the cells into the subject. Such delivery devices include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The stem cells can be inserted into such a delivery device, e.g., a syringe, in different forms. For example, the cells can be suspended in a solution, be in cell aggregates, or alternatively embedded in a support matrix when contained in such a delivery device.

Support matrices in which the stem cells or neurons can be incorporated or embedded include matrices that are recipient-compatible and that degrade into products that are not harmful to the recipient. The support matrices can be natural (e.g., hyaluronic acid, collagen, etc.) and/or synthetic biodegradable matrices. Synthetic biodegradable matrices that may be used include synthetic polymers such as polyanhydrides, polyorthoesters, and polylactic acid. In some embodiments, dopaminergic neurons (e.g., dopaminergic neurons that are not fully differentiated) are embedded in hyaluronic acid matrix and administered to a subject to treat a neurodegenerative disease (e.g., Parkinson's disease).

As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is known in the art. The solution is preferably sterile and fluid to the extent that easy syringability exists.

Preferably, the solution is stable under the conditions of manufacture and storage and preserved against the contaminating action of microorganisms such as bacteria and fungi. In some embodiments a solution containing DA neurons or midbrain DA neurons is administered to a patient in sterile solution of BSS PLUS (Alcon, Fort Worth, Tex.). If desired a preservative or antibiotic may be included in the pharmaceutical composition for administration. Solutions of the invention can be prepared by incorporating neurons as described herein in a pharmaceutically acceptable carrier or diluent and, other ingredients if desired.

3. Dosage and Administration

In one aspect, the methods described herein provide a method for enhancing engraftment of progenitor cells or DA neurons in a subject. In one embodiment, the subject can be a mammal. In another embodiment, the mammal can be a human, although the invention is effective with respect to all mammals.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of each active ingredient required to be administered depend on the judgment of the practitioner and are particular to each individual. However, suitable dosage ranges depend on the route of administration. Suitable regimes for administration are also variable.

4. Efficacy

The efficacy of a given treatment to enhance DA neuron engraftment can be determined by the skilled artisan. However, a treatment is considered "effective treatment," as the term is used herein, if any one or all of the signs or symptoms of e.g., poor DA neuron engraftment are altered in a beneficial manner, other clinically accepted symptoms are improved, or even ameliorated, e.g., by at least 10% following treatment with a cell population as described herein. Efficacy can also be measured by a failure of an individual to worsen as assessed by hospitalization, need for medical interventions (i.e., progression of the disease is halted), or incidence of engraftment failure. Methods of measuring these indicators are known to those of skill in the art and/or are described herein. Treatment includes any treatment of a disease in an individual or an animal (some non-limiting examples include a human or a mammal) and includes: (1) inhibiting the disease, e.g., preventing engraftment failure; or (2) relieving the disease, e.g., causing regression of symptoms. An effective amount for the treatment of a disease means an amount which, when administered to a mammal in need thereof, is sufficient to result in a treatment or therapeutic benefit for that disease. Efficacy of an agent can be determined by assessing physical indicators of, for example, DA neuron engraftment, such as, e.g., tremor, bradykinesia, flexed posture, balance and coordination, etc. In some embodiments, engraftment or neural function may be measured in vivo (e.g., in humans) using a PET scan to measure metabolism or activity or dopaminergic systems (e.g., using PET tracers for imaging of the dopaminergic system). Efficacy can be assessed in animal models of Parkinson's disease, for example, by performing behavioral tests, such as step tests or cylinder tests.

C. Distribution for Commercial, Therapeutic, and Research Purposes

For purposes of manufacture, distribution, and use, the neural cells such as midbrain DA neurons as described herein may be supplied in the form of a cell culture or suspension in an isotonic excipient or culture medium, optionally frozen to facilitate transportation or storage.

Neural cells described herein may be provided different reagent systems, e.g., comprising a set or combination of cells that exist at any time during manufacture, distribution, or use. The cell sets may comprise any combination of two or more cell populations described in this disclosure, exemplified but not limited to programming-derived cells (neural lineage cells, their precursors and subtypes), in combination with undifferentiated stem cells or other differentiated cell types. The cell populations in the set may share the same genome or a genetically modified form thereof. Each cell type in the set may be packaged together, or in separate containers in the same facility, or at different locations, at the same or different times, under control of the same entity or different entities sharing a business relationship.

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Midbrain neuronal differentiation of human induced pluripotent stem cell (iPS) cell lines expanded on VTN-TN in Essential 8 medium was performed with small molecule and growth factor induction using a variety of differentiation media compositions and schedules as detailed in Tables 1-5. Generally, the iPS cells were cultured in D1 DA Neuron Induction Medium on Day 1, D2 Neuron Induction Medium on Day 2, and D3-D4 DA Induction Medium on Day 3 and 4. On Day 5, the cells were dissociated with TrypLE for 15 minutes and collected in DA Quench Medium before transferring the cells to a spinner flask suspension culture to form aggregates in D5 DA Neuron Aggregate Formation Medium.

On Day 6, the aggregates were settled, about 66% of the medium was removed, and the aggregates were fed DA Neuron Induction Medium. On Days 7-16, the aggregates were fed daily with DA Neuron Aggregate Maintenance Medium, and the medium was changed on Day 11 through 16. On Day 17, aggregates were dissociated to a single-cell suspension with TrypLE and plated onto Matrigel in D17 DA Neuron Aggregate Plating Medium. On Days 18, 20, 22 the medium was replaced with DopaNeuron Maturation Medium. On Day 24, the cells were dissociated using Accutase and plated in DA Neuron Maturation Plating Medium. The next day, the medium was replaced with DopaNeuron Maturation Medium.

On Days 27 and 29, the media was replaced with DA Neuron Maturation Medium plus Mitomycin C. On Day 31, the cells were dissociated with Accutase and re-plated onto poly-L-ornithine (PLO)/Laminin-coated flasks in DA Neuron Maturation Plating Medium. Next, on Days 32, 34, and 36, the cells were fed DopaNeuron Maturation Medium. On Day 37 or 38, the cells were again dissociated with Accutase and subjected to analysis or cryopreserved for later use.

TABLE 1

| Regular timing media conditions (10 µM SB43 + 200 nM LDN). | | | | |
| --- | --- | --- | --- | --- |
| Component | Vendor | Cat# | Stock | Final Conc. |
| E8 Plating Medium (Day −2) | | | | |
| Essential 8 Basal Medium | Life Technologies | A14666SA | 1X | 98% |
| Essential 8 Supplement | Life Technologies | A14666SA | 50X | 2% |
| H1152 | CDI | H024 | 100 µM | 1 µM |

TABLE 1-continued

Regular timing media conditions (10 μM SB43 + 200 nM LDN).

| Component | Vendor | Cat# | Stock | Final Conc. |
|---|---|---|---|---|
| E8 Medium (Days −1 and 0) | | | | |
| Essential 8 Basal Medium | Life Technologies | A14666SA | 1X | 98% |
| Essential 8 Supplement | Life Technologies | A14666SA | 50X | 2% |
| D 1 DA Induction Medium (Day 1) | | | | |
| DMEM/F12 | Life Technologies | 11330-032 | 1X | 98% |
| B-27 Supplement (+VitA) | Life Technologies | 17504-044 | 2X | 2% |
| LDN-193189 | Stemgent | 04-0074 | 10 mM | 200 nM |
| SB431542 | Sigma | S4317 | 40 mM | 10 μM |
| Purmorphamine | Cayman | 10009634 | 10 mM | 2 μM |
| C25II SHH | R&D Systems | 464-SH | 100 μg/mL | 100 ng/mL |
| CHIR99021 | Stemgent | 04-0004 | 20 mM | 1.25 μM |
| D 2 DA Induction Medium (Day 2) | | | | |
| DMEM/F12 | Life Technologies | 11330-032 | 1X | 98% |
| B-27 Supplement (+VitA) | Life Technologies | 17504-044 | 2X | 2% |
| LDN-193189 | Stemgent | 04-0074 | 10 mM | 200 nM |
| SB431542 | Sigma | S4317 | 40 mM | 10 μM |
| Purmorphamine | Cayman | 10009634 | 10 mM | 2 μM |
| C25II SHH | R&D Systems | 464-SH | 100 μg/mL | 100 ng/mL |
| CHIR99021 | Stemgent | 04-0004 | 20 mM | 1.25 μM |
| PD0325901 | Stemgent | 04-0006 | 10 mM | 1.0 μM |
| D 3-4 DA Induction Medium (Days 3 and 4) | | | | |
| DMEM/F12 | Life Technologies | 11330-032 | 1X | 98% |
| B-27 Supplement (−VitA) | Life Technologies | 12587-010 | 2X | 2% |
| LDN-193189 | Stemgent | 04-0074 | 10 mM | 200 nM |
| SB431542 | Sigma | S4317 | 40 mM | 10 μM |
| D 11-16 DA Aggregate Maintenance Medium (Days 11-16) | | | | |
| DMEM/F12 | Life Technologies | 11330-032 | 1X | 98% |
| B-27 Supplement (−VitA) | Life Technologies | 12587-010 | 2X | 2% |
| LDN-193189 | Stemgent | 04-0074 | 10 mM | 200 nM |
| CHIR99021 | Stemgent | 04-0004 | 20 mM | 3.0 μM |
| FGF8 | R&D Systems | 423-F8 | 50 μg/mL | 100 ng/mL |
| D 17 DA Aggregate Plating Medium (Days 17) | | | | |
| DMEM/F12 | Life Technologies | 11330-032 | 1X | 98% |
| B-27 Supplement (−VitA) | Life Technologies | 12587-010 | 2X | 2% |
| LDN-193189 | Stemgent | 04-0074 | 10 mM | 200 nM |
| CHIR99021 | Stemgent | 04-0004 | 20 mM | 3.0 μM |
| FGF8 | R&D Systems | 423-F8 | 50 μg/mL | 100 ng/mL |
| Blebbistatin | Sigma | B0560 | 10,000x | 2.5 μM |
| DA Maturation Medium (Days 18+) | | | | |
| Neurobasal | Life Technologies | 21103-049 | 1X | 98% |
| Glutamax | Life Technologies | 35050-061 | 200 mM | 2 mM |
| B-27 Supplement (−VitA) | Life Technologies | 12587-010 | 2X | 2% |
| Ascorbic Acid | Sigma | A4403 | 200 mM | 200 μM |
| Rec Hu BDNF | R&D Systems | 248-BD | 20 μg/mL | 20 ng/mL |
| Rec Hu GDNF | R&D Systems | 212-GD | 20 μg/mL | 20 ng/mL |
| Rec Hu TGFB3 | R&D Systems | 243-B3 | 10 μg/mL | 1 ng/mL |
| dbcAMP | Sigma | D0627 | 100 mM | 500 μM |
| DAPT | Sigma | D5942 | 20 mM | 5 μM |
| DA Maturation Medium + MMC (Days 27 and 29) | | | | |
| Neurobasal | Life Technologies | 21103-049 | 1X | 98% |
| Glutamax | Life Technologies | 35050-061 | 200 mM | 2 mM |
| B-27 Supplement (−VitA) | Life Technologies | 12587-010 | 2X | 2% |
| Ascorbic Acid | Sigma | A4403 | 200 mM | 200 μM |
| Rec Hu BDNF | R&D Systems | 248-BD | 20 μg/mL | 20 ng/mL |
| Rec Hu GDNF | R&D Systems | 212-GD | 20 μg/mL | 20 ng/mL |
| Rec Hu TGFB3 | R&D Systems | 243-B3 | 10 μg/mL | 1 ng/mL |
| dbcAMP | Sigma | D0627 | 100 mM | 500 μM |
| DAPT | Sigma | D5942 | 20 mM | 5 μM |
| Mitomycin C | Sigma | M4287 | 1 mg/mL | 100 ng/mL |
| DA Quench Medium 2 (Days 18+) | | | | |
| Neurobasal | Life Technologies | 21103-049 | 1X | 98% |
| Glutamax | Life Technologies | 35050-061 | 200 mM | 2 mM |
| B-27 Supplement (−VitA) | Life Technologies | 12587-010 | 2X | 2% |
| Blebbistatin | Sigma | B0560 | 10,000x | 2.5 μM |

TABLE 1-continued

Regular timing media conditions (10 μM SB43 + 200 nM LDN).

| Component | Vendor | Cat# | Stock | Final Conc. |
|---|---|---|---|---|
| DA Maturation Plating Medium (Days 18+) | | | | |
| Neurobasal | Life Technologies | 21103-049 | 1X | 98% |
| Glutamax | Life Technologies | 35050-061 | 200 mM | 2 mM |
| B-27 Supplement (−VitA) | Life Technologies | 12587-010 | 2X | 2% |
| Ascorbic Acid | Sigma | A4403 | 200 mM | 200 μM |
| Rec Hu BDNF | R&D Systems | 248-BD | 20 μg/mL | 20 ng/mL |
| Rec Hu GDNF | R&D Systems | 212-GD | 20 μg/mL | 20 ng/mL |
| Rec Hu TGFB3 | R&D Systems | 243-B3 | 10 μg/mL | 1 ng/mL |
| dbcAMP | Sigma | D0627 | 100 mM | 500 μM |
| DAPT | Sigma | D5942 | 20 mM | 5 μM |
| Blebbistatin | Sigma | B0560 | 10,000x | 2.5 μM |

TABLE 2

Regular timing media conditions (2 μM Dorsomorphin).

| Component | Vendor | Cat# | Stock | Final Conc. |
|---|---|---|---|---|
| E8 Plating Medium (Day −2) | | | | |
| Essential 8 Basal Medium | Life Technologies | A14666SA | 1X | 98% |
| Essential 8 Supplement | Life Technologies | A14666SA | 50X | 2% |
| H1152 | CDI | H024 | 100 μM | 1 μM |
| E8 Medium (Day −1 and 0) | | | | |
| Essential 8 Basal Medium | Life Technologies | A14666SA | 1X | 98% |
| Essential 8 Supplement | Life Technologies | A14666SA | 50X | 2% |
| D 1 DA Induction Medium (Day 1) | | | | |
| DMEM/F12 | Life Technologies | 11330-032 | 1X | 98% |
| B-27 Supplement (+VitA) | Life Technologies | 17504-044 | 2X | 2% |
| Dorsomorphin | Sigma | P5499 | 2.5 mM | 2 μM |
| Purmorphamine | Cayman | 10009634 | 10 mM | 2 μM |
| C25II SHH | R&D Systems | 464-SH | 100 μg/mL | 100 ng/mL |
| CHIR99021 | Stemgent | 04-0004 | 20 mM | 1.25 μM |
| D 2 DA Induction Medium (Day 2) | | | | |
| DMEM/F12 | Life Technologies | 11330-032 | 1X | 98% |
| B-27 Supplement (+VitA) | Life Technologies | 17504-044 | 2X | 2% |
| Dorsomorphin | Sigma | P5499 | 2.5 mM | 2 μM |
| Purmorphamine | Cayman | 10009634 | 10 mM | 2 μM |
| C25II SHH | R&D Systems | 464-SH | 100 μg/mL | 100 ng/mL |
| CHIR99021 | Stemgent | 04-0004 | 20 mM | 1.25 μM |
| PD0325901 | Stemgent | 04-0006 | 10 mM | 1.0 μM |
| D 3-4 DA Induction Medium (Days 3 and 4) | | | | |
| DMEM/F12 | Life Technologies | 11330-032 | 1X | 98% |
| B-27 Supplement (−VitA) | Life Technologies | 12587-010 | 2X | 2% |
| Dorsomorphin | Sigma | P5499 | 2.5 mM | 2 μM |
| Purmorphamine | Cayman | 10009634 | 10 mM | 2 μM |
| C25II SHH | R&D Systems | 464-SH | 100 μg/mL | 100 ng/mL |
| CHIR99021 | Stemgent | 04-0004 | 20 mM | 1.25 μM |
| PD0325901 | Stemgent | 04-0006 | 10 mM | 1.0 μM |
| DA Quench Medium 1 (Days 5 and 17) | | | | |
| DMEM/F12 | Life Technologies | 11330-032 | 1X | 98% |
| B-27 Supplement (−VitA) | Life Technologies | 12587-010 | 2X | 2% |
| Blebbistatin | Sigma | B0560 | 10,000x | 2.5 μM |
| D 5 DA Aggregate Formation Medium (Day 5) | | | | |
| DMEM/F12 | Life Technologies | 11330-032 | 1X | 98% |
| B-27 Supplement (−VitA) | Life Technologies | 12587-010 | 2X | 2% |
| Dorsomorphin | Sigma | P5499 | 2.5 mM | 2 μM |
| Purmorphamine | Cayman | 10009634 | 10 mM | 2 μM |
| C25II SHH | R&D Systems | 464-SH | 100 μg/mL | 100 ng/mL |
| CHIR99021 | Stemgent | 04-0004 | 20 mM | 1.25 μM |
| Blebbistatin | Sigma | B0560 | 2,500x | 10 μM |
| D 6 DA Induction Medium (Day 6) | | | | |
| DMEM/F12 | Life Technologies | 11330-032 | 1X | 98% |
| B-27 Supplement (−VitA) | Life Technologies | 12587-010 | 2X | 2% |
| Dorsomorphin | Sigma | P5499 | 2.5 mM | 2 μM |

TABLE 2-continued

Regular timing media conditions (2 μM Dorsomorphin).

| Component | Vendor | Cat# | Stock | Final Conc. |
|---|---|---|---|---|
| Purmorphamine | Cayman | 10009634 | 10 mM | 2 μM |
| C25II SHH | R&D Systems | 464-SH | 100 μg/mL | 100 ng/mL |
| CHIR99021 | Stemgent | 04-0004 | 20 mM | 1.25 μM |
| D 7-10 DA Aggregate Maintenance Medium (Days 7-10) | | | | |
| DMEM/F12 | Life Technologies | 11330-032 | 1X | 98% |
| B-27 Supplement (−VitA) | Life Technologies | 12587-010 | 2X | 2% |
| Dorsomorphin | Sigma | P5499 | 2.5 mM | 2 μM |
| CHIR99021 | Stemgent | 04-0004 | 20 mM | 1.25 μM |
| D 11-16 DA Aggregate Maintenance Medium (Days 11-16) | | | | |
| DMEM/F12 | Life Technologies | 11330-032 | 1X | 98% |
| B-27 Supplement (−VitA) | Life Technologies | 12587-010 | 2X | 2% |
| Dorsomorphin | Sigma | P5499 | 2.5 mM | 2 μM |
| CHIR99021 | Stemgent | 04-0004 | 20 mM | 3.0 μM |
| FGF8 | R&D Systems | 423-F8 | 50 μg/mL | 100 ng/mL |
| D 17 DA Aggregate Plating Medium (Days 17) | | | | |
| DMEM/F12 | Life Technologies | 11330-032 | 1X | 98% |
| B-27 Supplement (−VitA) | Life Technologies | 12587-010 | 2X | 2% |
| Dorsomorphin | Sigma | P5499 | 2.5 mM | 2 μM |
| CHIR99021 | Stemgent | 04-0004 | 20 mM | 3.0 μM |
| FGF8 | R&D Systems | 423-F8 | 50 μg/mL | 100 ng/mL |
| Blebbistatin | Sigma | B0560 | 10,000x | 2.5 μM |
| DA Maturation Medium (Days 18+) | | | | |
| Neurobasal | Life Technologies | 21103-049 | 1X | 98% |
| Glutamax | Life Technologies | 35050-061 | 200 mM | 2 mM |
| B-27 Supplement (−VitA) | Life Technologies | 12587-010 | 2X | 2% |
| Ascorbic Acid | Sigma | A4403 | 200 mM | 200 μM |
| Rec Hu BDNF | R&D Systems | 248-BD | 20 μg/mL | 20 ng/mL |
| Rec Hu GDNF | R&D Systems | 212-GD | 20 μg/mL | 20 ng/mL |
| Rec Hu TGFB3 | R&D Systems | 243-B3 | 10 μg/mL | 1 ng/mL |
| dbcAMP | Sigma | D0627 | 100 mM | 500 μM |
| DAPT | Sigma | D5942 | 20 mM | 5 μM |
| DA Maturation Medium + MMC (Days 27 and 29) | | | | |
| Neurobasal | Life Technologies | 21103-049 | 1X | 98% |
| Glutamax | Life Technologies | 35050-061 | 200 mM | 2 mM |
| B-27 Supplement (−VitA) | Life Technologies | 12587-010 | 2X | 2% |
| Ascorbic Acid | Sigma | A4403 | 200 mM | 200 μM |
| Rec Hu BDNF | R&D Systems | 248-BD | 20 μg/mL | 20 ng/mL |
| Rec Hu GDNF | R&D Systems | 212-GD | 20 μg/mL | 20 ng/mL |
| Rec Hu TGFB3 | R&D Systems | 243-B3 | 10 μg/mL | 1 ng/mL |
| dbcAMP | Sigma | D0627 | 100 mM | 500 μM |
| DAPT | Sigma | D5942 | 20 mM | 5 μM |
| Mitomycin C | Sigma | M4287 | 1 mg/mL | 100 ng/mL |
| DA Quench Medium 2 (Days 18+) | | | | |
| Neurobasal | Life Technologies | 21103-049 | 1X | 98% |
| Glutamax | Life Technologies | 35050-061 | 200 mM | 2 mM |
| B-27 Supplement (−VitA) | Life Technologies | 12587-010 | 2X | 2% |
| Blebbistatin | Sigma | B0560 | 10,000x | 2.5 μM |
| DA Maturation Plating Medium (Days 18+) | | | | |
| Neurobasal | Life Technologies | 21103-049 | 1X | 98% |
| Glutamax | Life Technologies | 35050-061 | 200 mM | 2 mM |
| B-27 Supplement (−VitA) | Life Technologies | 12587-010 | 2X | 2% |
| Ascorbic Acid | Sigma | A4403 | 200 mM | 200 μM |
| Rec Hu BDNF | R&D Systems | 248-BD | 20 μg/mL | 20 ng/mL |
| Rec Hu GDNF | R&D Systems | 212-GD | 20 μg/mL | 20 ng/mL |
| Rec Hu TGFB3 | R&D Systems | 243-B3 | 10 μg/mL | 1 ng/mL |
| dbcAMP | Sigma | D0627 | 100 mM | 500 μM |
| DAPT | Sigma | D5942 | 20 mM | 5 μM |
| Blebbistatin | Sigma | B0560 | 10,000x | 2.5 μM |

TABLE 3

Regular timing media conditions (200 nM LDN).

| Component | Vendor | Cat# | Stock | Final Conc. |
|---|---|---|---|---|
| E8 Plating Medium (Day −2) | | | | |
| Essential 8 Basal Medium | Life Technologies | A14666SA | 1× | 98% |
| Essential 8 Supplement | Life Technologies | A14666SA | 50× | 2% |
| H1152 | CDI | H024 | 100 μM | 1 μM |
| E8 Medium (Days −1 and 0) | | | | |
| Essential 8 Basal Medium | Life Technologies | A146665A | 1× | 98% |
| Essential 8 Supplement | Life Technologies | A146665A | 50× | 2% |
| D1 DA Induction Medium (Day 1) | | | | |
| DMEM/F12 | Life Technologies | 11330-032 | 1× | 98% |
| B-27 Supplement (+VitA) | Life Technologies | 17504-044 | 2× | 2% |
| LDN-193189 | Stemgent | 04-0074 | 10 mM | 200 nM |
| Purmorphamine | Cayman | 10009634 | 10 mM | 2 μM |
| C25II SHH | R&D Systems | 464-SH | 100 μg/mL | 100 ng/mL |
| CHIR99021 | Stemgent | 04-0004 | 20 mM | 1.25 μM |
| D2 DA Induction Medium (Day 2) | | | | |
| DMEM/F12 | Life Technologies | 11330-032 | 1× | 98% |
| B-27 Supplement (+VitA) | Life Technologies | 17504-044 | 2× | 2% |
| LDN-193189 | Stemgent | 04-0074 | 10 mM | 200 nM |
| Purmorphamine | Cayman | 10009634 | 10 mM | 2 μM |
| C25II SHH | R&D Systems | 464-SH | 100 μg/mL | 100 ng/mL |
| CHIR99021 | Stemgent | 04-0004 | 20 mM | 1.25 μM |
| PD0325901 | Stemgent | 04-0006 | 10 mM | 1.0 μM |
| D3-4 DA Induction Medium (Days 3 and 4) | | | | |
| DMEM/F12 | Life Technologies | 11330-032 | 1× | 98% |
| B-27 Supplement (−VitA) | Life Technologies | 12587-010 | 2× | 2% |
| LDN-193189 | Stemgent | 04-0074 | 10 mM | 200 nM |
| Purmorphamine | Cayman | 10009634 | 10 mM | 2 μM |
| C25II SHH | R&D Systems | 464-SH | 100 μg/mL | 100 ng/mL |
| CHIR99021 | Stemgent | 04-0004 | 20 mM | 1.25 μM |
| PD0325901 | Stemgent | 04-0006 | 10 mM | 1.0 μM |
| DA Quench Medium 1 (Days 5 and 17) | | | | |
| DMEM/F12 | Life Technologies | 11330-032 | 1× | 98% |
| B-27 Supplement (−VitA) | Life Technologies | 12587-010 | 2× | 2% |
| Blebbistatin | Sigma | B0560 | 10,000× | 2.5 μM |
| D5 DA Aggregate Formation Medium (Day 5) | | | | |
| DMEM/F12 | Life Technologies | 11330-032 | 1× | 98% |
| B-27 Supplement (−VitA) | Life Technologies | 12587-010 | 2× | 2% |
| LDN-193189 | Stemgent | 04-0074 | 10 mM | 200 nM |
| Purmorphamine | Cayman | 10009634 | 10 mM | 2 μM |
| C25II SHH | R&D Systems | 464-SH | 100 μg/mL | 100 ng/mL |
| CHIR99021 | Stemgent | 04-0004 | 20 mM | 1.25 μM |
| Blebbistatin | Sigma | B0560 | 2,500× | 10 μM |
| D6 DA Induction Medium (Day 6) | | | | |
| DMEM/F12 | Life Technologies | 11330-032 | 1× | 98% |
| B-27 Supplement (−VitA) | Life Technologies | 12587-010 | 2× | 2% |
| LDN-193189 | Stemgent | 04-0074 | 10 mM | 200 nM |
| Purmorphamine | Cayman | 10009634 | 10 mM | 2 μM |
| C25II SHH | R&D Systems | 464-SH | 100 μg/mL | 100 ng/mL |
| CHIR99021 | Stemgent | 04-0004 | 20 mM | 1.25 μM |
| D7-10 DA Aggregate Maintenance Medium (Days 7-10) | | | | |
| DMEM/F12 | Life Technologies | 11330-032 | 1× | 98% |
| B-27 Supplement (−VitA) | Life Technologies | 12587-010 | 2× | 2% |
| LDN-193189 | Stemgent | 04-0074 | 10 mM | 200 nM |
| CHIR99021 | Stemgent | 04-0004 | 20 mM | 1.25 μM |
| D11-16 DA Aggregate Maintenance Medium (Days 11-16) | | | | |
| DMEM/F12 | Life Technologies | 11330-032 | 1× | 98% |
| B-27 Supplement (−VitA) | Life Technologies | 12587-010 | 2× | 2% |
| LDN-193189 | Stemgent | 04-0074 | 10 mM | 200 nM |
| CHIR99021 | Stemgent | 04-0004 | 20 mM | 3.0 μM |
| FGF8 | R&D Systems | 423-F8 | 50 μg/mL | 100 ng/mL |
| D17 DA Aggregate Plating Medium (Days 17) | | | | |
| DMEM/F12 | Life Technologies | 11330-032 | 1× | 98% |
| B-27 Supplement (−VitA) | Life Technologies | 12587-010 | 2× | 2% |
| LDN-193189 | Stemgent | 04-0074 | 10 mM | 200 nM |
| CHIR99021 | Stemgent | 04-0004 | 20 mM | 3.0 μM |

TABLE 3-continued

Regular timing media conditions (200 nM LDN).

| Component | Vendor | Cat# | Stock | Final Conc. |
|---|---|---|---|---|
| FGF8 | R&D Systems | 423-F8 | 50 μg/mL | 100 ng/mL |
| Blebbistatin | Sigma | B0560 | 10,000× | 2.5 μM |
| DA Maturation Medium (Days 18+) | | | | |
| Neuro basal | Life Technologies | 21103-049 | 1× | 98% |
| Glutamax | Life Technologies | 35050-061 | 200 mM | 2 mM |
| B-27 Supplement (−VitA) | Life Technologies | 12587-010 | 2× | 2% |
| Ascorbic Acid | Sigma | A4403 | 200 mM | 200 μM |
| Rec Hu BDNF | R&D Systems | 248-BD | 20 μg/mL | 20 ng/mL |
| Rec Hu GDNF | R&D Systems | 212-GD | 20 μg/mL | 20 ng/mL |
| Rec Hu TGFB3 | R&D Systems | 243-B3 | 10 μg/mL | 1 ng/mL |
| dbcAMP | Sigma | D0627 | 100 mM | 500 μM |
| DAPT | Sigma | D5942 | 20 mM | 5 μM |
| DA Maturation Medium + MMC (Days 27 and 29) | | | | |
| Neuro basal | Life Technologies | 21103-049 | 1× | 98% |
| Glutamax | Life Technologies | 35050-061 | 200 mM | 2 mM |
| B-27 Supplement (−VitA) | Life Technologies | 12587-010 | 2× | 2% |
| Ascorbic Acid | Sigma | A4403 | 200 mM | 200 μM |
| Rec Hu BDNF | R&D Systems | 248-BD | 20 μg/mL | 20 ng/mL |
| Rec Hu GDNF | R&D Systems | 212-GD | 20 μg/mL | 20 ng/mL |
| Rec Hu TGFB3 | R&D Systems | 243-B3 | 10 μg/mL | 1 ng/mL |
| dbcAMP | Sigma | D0627 | 100 mM | 500 μM |
| DAPT | Sigma | D5942 | 20 mM | 5 μM |
| Mitomycin C | Sigma | M4287 | 1 mg/mL | 100 ng/mL |
| DA Quench Medium 2 (Days 18+) | | | | |
| Neuro basal | Life Technologies | 21103-049 | 1× | 98% |
| Glutamax | Life Technologies | 35050-061 | 200 mM | 2 mM |
| B-27 Supplement (−VitA) | Life Technologies | 12587-010 | 2× | 2% |
| Blebbistatin | Sigma | B0560 | 10,000× | 2.5 μM |
| DA Maturation Plating Medium (Days 18+) | | | | |
| Neuro basal | Life Technologies | 21103-049 | 1× | 98% |
| Glutamax | Life Technologies | 35050-061 | 200 mM | 2 mM |
| B-27 Supplement (−VitA) | Life Technologies | 12587-010 | 2× | 2% |
| Ascorbic Acid | Sigma | A4403 | 200 mM | 200 μM |
| Rec Hu BDNF | R&D Systems | 248-BD | 20 μg/mL | 20 ng/mL |
| Rec Hu GDNF | R&D Systems | 212-GD | 20 μg/mL | 20 ng/mL |
| Rec Hu TGFB3 | R&D Systems | 243-B3 | 10 μg/mL | 1 ng/mL |
| dbcAMP | Sigma | D0627 | 100 mM | 500 μM |
| DAPT | Sigma | D5942 | 20 mM | 5 μM |
| Blebbistatin | Sigma | B0560 | 10,000× | 2.5 μM |

TABLE 4

Alternate timing media conditions (200 nM LDN)

| Component | Vendor | Cat# | Stock | Final Conc. |
|---|---|---|---|---|
| E8 Plating Medium (Day −2) | | | | |
| Essential 8 Basal Medium | Life Technologies | A14666SA | 1× | 98% |
| Essential 8 Supplement | Life Technologies | A14666SA | 50× | 2% |
| H1152 | CDI | H024 | 100 μM | 1 μM |
| E8 Medium (Days −1 and 0) | | | | |
| Essential 8 Basal Medium | Life Technologies | A14666SA | 1× | 98% |
| Essential 8 Supplement | Life Technologies | A146665A | 50× | 2% |
| D1 DA Induction Medium (Day 1) | | | | |
| DMEM/F12 | Life Technologies | 11330-032 | 1× | 98% |
| B-27 Supplement (+VitA) | Life Technologies | 17504-044 | 2× | 2% |
| LDN-193189 | Stemgent | 04-0074 | 10 mM | 200 nM |
| D2 DA Induction Medium (Day 2) | | | | |
| DMEM/F12 | Life Technologies | 11330-032 | 1× | 98% |
| B-27 Supplement (+VitA) | Life Technologies | 17504-044 | 2× | 2% |
| LDN-193189 | Stemgent | 04-0074 | 10 mM | 200 nM |
| Purmorphamine | Cayman | 10009634 | 10 mM | 2 μM |
| C25II SHH | R&D Systems | 464-SH | 100 μg/mL | 100 ng/mL |

TABLE 4-continued

| Alternate timing media conditions (200 nM LDN) | | | | |
|---|---|---|---|---|
| Component | Vendor | Cat# | Stock | Final Conc. |
| D3-4 DA Induction Medium (Days 3 and 4) | | | | |
| DMEM/F12 | Life Technologies | 11330-032 | 1× | 98% |
| B-27 Supplement (−VitA) | Life Technologies | 12587-010 | 2× | 2% |
| LDN-193189 | Stemgent | 04-0074 | 10 mM | 200 nM |
| Purmorphamine | Cayman | 10009634 | 10 mM | 2 µM |
| C25II SHH | R&D Systems | 464-SH | 100 µg/mL | 100 ng/mL |
| CHIR99021 | Stemgent | 04-0004 | 20 mM | 2.00 µM |
| PD0325901 | Stemgent | 04-0006 | 10 mM | 1.0 µM |
| DA Quench Medium 1 (Days 5 and 17) | | | | |
| DMEM/F12 | Life Technologies | 11330-032 | 1× | 98% |
| B-27 Supplement (−VitA) | Life Technologies | 12587-010 | 2× | 2% |
| Blebbistatin | Sigma | B0560 | 10,000× | 2.5 µM |
| D5 DA Aggregate Formation Medium (Day 5) | | | | |
| DMEM/F12 | Life Technologies | 11330-032 | 1× | 98% |
| B-27 Supplement (−VitA) | Life Technologies | 12587-010 | 2× | 2% |
| LDN-193189 | Stemgent | 04-0074 | 10 mM | 200 nM |
| Purmorphamine | Cayman | 10009634 | 10 mM | 2 µM |
| C25II SHH | R&D Systems | 464-SH | 100 µg/mL | 100 ng/mL |
| CHIR99021 | Stemgent | 04-0004 | 20 mM | 2.00 µM |
| PD0325901 | Stemgent | 04-0006 | 10 mM | 1.0 µM |
| Blebbistatin | Sigma | B0560 | 2,500× | 10 µM |
| D6-7 DA Induction Medium (Day 6-7) | | | | |
| DMEM/F12 | Life Technologies | 11330-032 | 1× | 98% |
| B-27 Supplement (−VitA) | Life Technologies | 12587-010 | 2× | 2% |
| LDN-193189 | Stemgent | 04-0074 | 10 mM | 200 nM |
| Purmorphamine | Cayman | 10009634 | 10 mM | 2 µM |
| C25II SHH | R&D Systems | 464-SH | 100 µg/mL | 100 ng/mL |
| CHIR99021 | Stemgent | 04-0004 | 20 mM | 2.00 µM |
| D8-10 DA Aggregate Maintenance Medium (Days 8-10) | | | | |
| DMEM/F12 | Life Technologies | 11330-032 | 1× | 98% |
| B-27 Supplement (−VitA) | Life Technologies | 12587-010 | 2× | 2% |
| LDN-193189 | Stemgent | 04-0074 | 10 mM | 200 nM |
| CHIR99021 | Stemgent | 04-0004 | 20 mM | 2.00 µM |
| D11-16 DA Aggregate Maintenance Medium (Days 11-16) | | | | |
| DMEM/F12 | Life Technologies | 11330-032 | 1× | 98% |
| B-27 Supplement (−VitA) | Life Technologies | 12587-010 | 2× | 2% |
| LDN-193189 | Stemgent | 04-0074 | 10 mM | 200 nM |
| CHIR99021 | Stemgent | 04-0004 | 20 mM | 3.0 µM |
| FGF8 | R&D Systems | 423-F8 | 50 µg/mL | 100 ng/mL |
| D17 DA Aggregate Plating Medium (Days 17) | | | | |
| DMEM/F12 | Life Technologies | 11330-032 | 1× | 98% |
| B-27 Supplement (−VitA) | Life Technologies | 12587-010 | 2× | 2% |
| LDN-193189 | Stemgent | 04-0074 | 10 mM | 200 nM |
| CHIR99021 | Stemgent | 04-0004 | 20 mM | 3.0 µM |
| FGF8 | R&D Systems | 423-F8 | 50 µg/mL | 100 ng/mL |
| Blebbistatin | Sigma | B0560 | 10,000× | 2.5 µM |
| DA Maturation Medium (Days 18+) | | | | |
| Neurobasal | Life Technologies | 21103-049 | 1× | 98% |
| Glutamax | Life Technologies | 35050-061 | 200 mM | 2 mM |
| B-27 Supplement (−VitA) | Life Technologies | 12587-010 | 2× | 2% |
| Ascorbic Acid | Sigma | A4403 | 200 mM | 200 µM |
| Rec Hu BDNF | R&D Systems | 248-BD | 20 µg/mL | 20 ng/mL |
| Rec Hu GDNF | R&D Systems | 212-GD | 20 µg/mL | 20 ng/mL |
| Rec Hu TGFB3 | R&D Systems | 243-B3 | 10 µg/mL | 1 ng/mL |
| dbcAMP | Sigma | D0627 | 100 mM | 500 µM |
| DAPT | Sigma | D5942 | 20 mM | 5 µM |
| DA Maturation Medium + MMC (Days 27 and 29) | | | | |
| Neurobasal | Life Technologies | 21103-049 | 1× | 98% |
| Glutamax | Life Technologies | 35050-061 | 200 mM | 2 mM |
| B-27 Supplement (−VitA) | Life Technologies | 12587-010 | 2× | 2% |
| Ascorbic Acid | Sigma | A4403 | 200 mM | 200 µM |
| Rec Hu BDNF | R&D Systems | 248-BD | 20 µg/mL | 20 ng/mL |
| Rec Hu GDNF | R&D Systems | 212-GD | 20 µg/mL | 20 ng/mL |
| Rec Hu TGFB3 | R&D Systems | 243-B3 | 10 µg/mL | 1 ng/mL |
| dbcAMP | Sigma | D0627 | 100 mM | 500 µM |
| DAPT | Sigma | D5942 | 20 mM | 5 µM |
| Mitomycin C | Sigma | M4287 | 1 mg/mL | 100 ng/mL |

TABLE 4-continued

Alternate timing media conditions (200 nM LDN)

| Component | Vendor | Cat# | Stock | Final Conc. |
|---|---|---|---|---|
| DA Quench Medium 2 (Days 18+) | | | | |
| Neurobasal | Life Technologies | 21103-049 | 1× | 98% |
| Glutamax | Life Technologies | 35050-061 | 200 mM | 2 mM |
| B-27 Supplement (−VitA) | Life Technologies | 12587-010 | 2× | 2% |
| Blebbistatin | Sigma | B0560 | 10,000× | 2.5 µM |
| DA Maturation Plating Medium (Days 18+) | | | | |
| Neurobasal | Life Technologies | 21103-049 | 1× | 98% |
| Glutamax | Life Technologies | 35050-061 | 200 mM | 2 mM |
| B-27 Supplement (−VitA) | Life Technologies | 12587-010 | 2× | 2% |
| Ascorbic Acid | Sigma | A4403 | 200 mM | 200 µM |
| Rec Hu BDNF | R&D Systems | 248-BD | 20 µg/mL | 20 ng/mL |
| Rec Hu GDNF | R&D Systems | 212-GD | 20 µg/mL | 20 ng/mL |
| Rec Hu TGFB3 | R&D Systems | 243-B3 | 10 µg/mL | 1 ng/mL |
| dbcAMP | Sigma | D0627 | 100 mM | 500 µM |
| DAPT | Sigma | D5942 | 20 mM | 5 µM |
| Blebbistatin | Sigma | B0560 | 10,000× | 2.5 µM |

TABLE 5

Alternate timing media conditions (2 µM Dorsomorphin).

| Component | Vendor | Cat# | Stock | Final Conc. |
|---|---|---|---|---|
| E8 Plating Medium (Day −2) | | | | |
| Essential 8 Basal Medium | Life Technologies | A14666SA | 1× | 98% |
| Essential 8 Supplement | Life Technologies | A146665A | 50× | 2% |
| H1152 | CDI | H024 | 100 µM | 1 µM |
| E8 Medium (Days −1 and 0) | | | | |
| Essential 8 Basal Medium | Life Technologies | A146665A | 1× | 98% |
| Essential 8 Supplement | Life Technologies | A146665A | 50× | 2% |
| D1 DA Induction Medium (Day 1) | | | | |
| DMEM/F12 | Life Technologies | 11330-032 | 1× | 98% |
| B-27 Supplement (+VitA) | Life Technologies | 17504-044 | 2× | 2% |
| Dorsomorphin | Sigma | P5499 | 2.5 mM | 2 mM |
| D2 DA Induction Medium (Day 2) | | | | |
| DMEM/F12 | Life Technologies | 11330-032 | 1× | 98% |
| B-27 Supplement (+VitA) | Life Technologies | 17504-044 | 2× | 2% |
| Dorsomorphin | Sigma | P5499 | 2.5 mM | 2 mM |
| Purmorphamine | Cayman | 10009634 | 10 mM | 2 mM |
| C25II SHH | R&D Systems | 464-SH | 100 mg/mL | 100 ng/mL |
| D3-4 DA Induction Medium (Days 3 and 4) | | | | |
| DMEM/F12 | Life Technologies | 11330-032 | 1× | 98% |
| B-27 Supplement (−VitA) | Life Technologies | 12587-010 | 2× | 2% |
| Dorsomorphin | Sigma | P5499 | 2.5 mM | 2 mM |
| Purmorphamine | Cayman | 10009634 | 10 mM | 2 mM |
| C25II SHH | R&D Systems | 464-SH | 100 mg/mL | 100 ng/mL |
| CHIR99021 | Stemgent | 04-0004 | 20 mM | 2.00 µM |
| PD0325901 | Stemgent | 04-0006 | 10 mM | 1.0 µM |
| DA Quench Medium 1 (Days 5 and 17) | | | | |
| DMEM/F12 | Life Technologies | 11330-032 | 1× | 98% |
| B-27 Supplement (−VitA) | Life Technologies | 12587-010 | 2× | 2% |
| Blebbistatin | Sigma | B0560 | 10,000× | 2.5 µM |
| DS DA Aggregate Formation Medium (Day 5) | | | | |
| DMEM/F12 | Life Technologies | 11330-032 | 1× | 98% |
| B-27 Supplement (−VitA) | Life Technologies | 12587-010 | 2× | 2% |
| Dorsomorphin | Sigma | P5499 | 2.5 mM | 2 mM |
| Purmorphamine | Cayman | 10009634 | 10 mM | 2 mM |
| C2II SHH | R&D Systems | 464-SH | 100 mg/mL | 100 ng/mL |
| CHIR99021 | Stemgent | 04-0004 | 20 mM | 2.00 µM |
| PD0325901 | Stemgent | 04-0006 | 10 mM | 1.0 µM |
| Blebbistatin | Sigma | B0560 | 2,500× | 10 µM |

TABLE 5-continued

Alternate timing media conditions (2 μM Dorsomorphin).

| Component | Vendor | Cat# | Stock | Final Conc. |
|---|---|---|---|---|
| D6-7 DA Induction Medium (Days 6-7) | | | | |
| DMEM/F12 | Life Technologies | 11330-032 | 1× | 98% |
| B-27 Supplement (−VitA) | Life Technologies | 12587-010 | 2× | 2% |
| Dorsomorphin | Sigma | P5499 | 2.5 mM | 2 mM |
| Purmorphamine | Cayman | 10009634 | 10 mM | 2 mM |
| C25II SHH | R&D Systems | 464-SH | 100 mg/mL | 100 ng/mL |
| CHIR99021 | Stemgent | 04-0004 | 20 mM | 2.00 μM |
| D8-10 DA Aggregate Maintenance Medium (Days 8-10) | | | | |
| DMEM/F12 | Life Technologies | 11330-032 | 1× | 98% |
| B-27 Supplement (−VitA) | Life Technologies | 12587-010 | 2× | 2% |
| Dorsomorphin | Sigma | P5499 | 2.5 mM | 2 mM |
| CHIR99021 | Stemgent | 04-0004 | 20 mM | 2.00 μM |
| D11-16 DA Aggregate Maintenance Medium (Days 11-16) | | | | |
| DMEM/F12 | Life Technologies | 11330-032 | 1× | 98% |
| B-27 Supplement (−VitA) | Life Technologies | 12587-010 | 2× | 2% |
| Dorsomorphin | Sigma | P5499 | 2.5 mM | 2 mM |
| CHIR99021 | Stemgent | 04-0004 | 20 mM | 3.0 μM |
| FGF8 | R&D Systems | 423-F8 | 50 μg/mL | 100 ng/mL |
| D17 DA Aggregate Plating Medium (Days 17) | | | | |
| DMEM/F12 | Life Technologies | 11330-032 | 1× | 98% |
| B-27 Supplement (−VitA) | Life Technologies | 12587-010 | 2× | 2% |
| Dorsomorphin | Sigma | P5499 | 2.5 mM | 2 mM |
| CHIR99021 | Stemgent | 04-0004 | 20 mM | 3.0 μM |
| FGF8 | R&D Systems | 423-F8 | 50 μg/mL | 100 ng/mL |
| Blebbistatin | Sigma | B0560 | 10,000× | 2.5 μM |
| DA Maturation Medium (Days 18+) | | | | |
| Neurobasal | Life Technologies | 21103-049 | 1× | 98% |
| Glutamax | Life Technologies | 35050-061 | 200 mM | 2 mM |
| B-27 Supplement (−VitA) | Life Technologies | 12587-010 | 2× | 2% |
| Ascorbic Acid | Sigma | A4403 | 200 mM | 200 mM |
| Rec Hu BDNF | R&D Systems | 248-BD | 20 mg/mL | 20 ng/mL |
| Rec Hu GDNF | R&D Systems | 212-GD | 20 mg/mL | 20 ng/mL |
| Rec Hu TGFB3 | R&D Systems | 243-B3 | 10 mg/mL | 1 ng/mL |
| dbcAMP | Sigma | D0627 | 100 mM | 500 mM |
| DAPT | Sigma | D5942 | 20 mM | 5 mM |
| DA Maturation Medium + MMC (Days 27 and 29) | | | | |
| Neurobasal | Life Technologies | 21103-049 | 1× | 98% |
| Glutamax | Life Technologies | 35050-061 | 200 mM | 2 mM |
| B-27 Supplement (−VitA) | Life Technologies | 12587-010 | 2× | 2% |
| Ascorbic Acid | Sigma | A4403 | 200 mM | 200 mM |
| Rec Hu BDNF | R&D Systems | 248-BD | 20 mg/mL | 20 ng/mL |
| Rec Hu GDNF | R&D Systems | 212-GD | 20 mg/mL | 20 ng/mL |
| Rec Hu TGFB3 | R&D Systems | 243-B3 | 10 mg/mL | 1 ng/mL |
| dbcAMP | Sigma | D0627 | 100 mM | 500 mM |
| DAPT | Sigma | D5942 | 20 mM | 5 mM |
| Mitomycin C | Sigma | M4287 | 1 mg/mL | 100 ng/mL |
| DA Quench Medium 2 (Days 18+) | | | | |
| Neurobasal | Life Technologies | 21103-049 | 1× | 98% |
| Glutamax | Life Technologies | 35050-061 | 200 mM | 2 mM |
| B-27 Supplement (−VitA) | Life Technologies | 12587-010 | 2× | 2% |
| Blebbistatin | Sigma | B0560 | 10,000× | 2.5 μM |
| DA Maturation Plating Medium (Days 18+) | | | | |
| Neurobasal | Life Technologies | 21103-049 | 1× | 98% |
| Glutamax | Life Technologies | 35050-061 | 200 mM | 2 mM |
| B-27 Supplement (−VitA) | Life Technologies | 12587-010 | 2× | 2% |
| Ascorbic Acid | Sigma | A4403 | 200 mM | 200 mM |
| Rec Hu BDNF | R&D Systems | 248-BD | 20 mg/mL | 20 ng/mL |
| Rec Hu GDNF | R&D Systems | 212-GD | 20 mg/mL | 20 ng/mL |
| Rec Hu TGFB3 | R&D Systems | 243-B3 | 10 mg/mL | 1 ng/mL |
| dbcAMP | Sigma | D0627 | 100 mM | 500 mM |
| DAPT | Sigma | D5942 | 20 mM | 5 mM |
| Blebbistatin | Sigma | B0560 | 10,000× | 2.5 μM |

TABLE 6

| Component | Vendor | Cat# | Stock | Final Conc. |
|---|---|---|---|---|
| \multicolumn{5}{c}{Condition 9 (200 nM LDN)} | | | | |

Condition 9 (200 nM LDN)

E8 Plating Medium (Day −2)

| Component | Vendor | Cat# | Stock | Final Conc. |
|---|---|---|---|---|
| Essential 8 Basal Medium | Life Technologies | A14666SA | 1× | 98% |
| Essential 8 Supplement | Life Technologies | A146665A | 50× | 2% |
| H1152 | CDI | H024 | 100 µM | 1 µM |

E8 Medium (Days −1 and 0)

| Essential 8 Basal Medium | Life Technologies | A146665A | 1× | 98% |
|---|---|---|---|---|
| Essential 8 Supplement | Life Technologies | A146665A | 50× | 2% |

D1 DA Induction Medium (Day 1)

| DMEM/F12 | Life Technologies | 11330-032 | 1× | 98% |
|---|---|---|---|---|
| B-27 Supplement (+VitA) | Life Technologies | 17504-044 | 2× | 2% |
| LDN-193189 | Stemgent | 04-0074 | 10 mM | 200 nM |
| Purmorphamine | Cayman | 10009634 | 10 mM | 2 µM |
| C25II SHH | R&D Systems | 464-SH | 100 µg/mL | 100 ng/mL |

D2 DA Induction Medium (Day 2)

| DMEM/F12 | Life Technologies | 11330-032 | 1× | 98% |
|---|---|---|---|---|
| B-27 Supplement (+VitA) | Life Technologies | 17504-044 | 2× | 2% |
| LDN-193189 | Stemgent | 04-0074 | 10 mM | 200 nM |
| Purmorphamine | Cayman | 10009634 | 10 mM | 2 µM |
| C25II SHH | R&D Systems | 464-SH | 100 µg/mL | 100 ng/mL |
| CHIR99021 | Stemgent | 04-0004 | 20 mM | 1.75 µM |

D3-4 DA Induction Medium (Days 3 and 4)

| DMEM/F12 | Life Technologies | 11330-032 | 1× | 98% |
|---|---|---|---|---|
| B-27 Supplement (−VitA) | Life Technologies | 12587-010 | 2× | 2% |
| LDN-193189 | Stemgent | 04-0074 | 10 mM | 200 nM |
| Purmorphamine | Cayman | 10009634 | 10 mM | 2 µM |
| C25II SHH | R&D Systems | 464-SH | 100 µg/mL | 100 ng/mL |
| CHIR99021 | Stemgent | 04-0004 | 20 mM | 1.75 µM |
| PD0325901 | Stemgent | 04-0006 | 10 mM | 1.0 µM |

DA Quench Medium 1 (Days 5 and 17)

| DMEM/F12 | Life Technologies | 11330-032 | 1× | 98% |
|---|---|---|---|---|
| B-27 Supplement (−VitA) | Life Technologies | 12587-010 | 2× | 2% |
| Blebbistatin | Sigma | B0560 | 10,000× | 2.5 µM |

D5 DA Aggregate Formation Medium (Day 5)

| DMEM/F12 | Life Technologies | 11330-032 | 1× | 98% |
|---|---|---|---|---|
| B-27 Supplement (−VitA) | Life Technologies | 12587-010 | 2× | 2% |
| LDN-193189 | Stemgent | 04-0074 | 10 mM | 200 nM |
| Purmorphamine | Cayman | 10009634 | 10 mM | 2 µM |
| C25II SHH | R&D Systems | 464-SH | 100 µg/mL | 100 ng/mL |
| CHIR99021 | Stemgent | 04-0004 | 20 mM | 1.75 µM |
| PD0325901 | Stemgent | 04-0006 | 10 mM | 1.0 µM |
| Blebbistatin | Sigma | B0560 | 2,500× | 10 µM |

D6-7 DA Induction Medium (Day 6-7)

| DMEM/F12 | Life Technologies | 11330-032 | 1× | 98% |
|---|---|---|---|---|
| B-27 Supplement (−VitA) | Life Technologies | 12587-010 | 2× | 2% |
| LDN-193189 | Stemgent | 04-0074 | 10 mM | 200 nM |
| Purmorphamine | Cayman | 10009634 | 10 mM | 2 µM |
| C25II SHH | R&D Systems | 464-SH | 100 µg/mL | 100 ng/mL |
| CHIR99021 | Stemgent | 04-0004 | 20 mM | 1.75 µM |

D8-10 DA Aggregate Maintenance Medium (Days 8-10)

| DMEM/F12 | Life Technologies | 11330-032 | 1× | 98% |
|---|---|---|---|---|
| B-27 Supplement (−VitA) | Life Technologies | 12587-010 | 2× | 2% |
| LDN-193189 | Stemgent | 04-0074 | 10 mM | 200 nM |
| CHIR99021 | Stemgent | 04-0004 | 20 mM | 1.75 µM |

D11-16 DA Aggregate Maintenance Medium (Days 11-16)

| DMEM/F12 | Life Technologies | 11330-032 | 1× | 98% |
|---|---|---|---|---|
| B-27 Supplement (−VitA) | Life Technologies | 12587-010 | 2× | 2% |
| LDN-193189 | Stemgent | 04-0074 | 10 mM | 200 nM |
| CHIR99021 | Stemgent | 04-0004 | 20 mM | 3.0 µM |
| FGF8 | R&D Systems | 423-F8 | 50 µg/mL | 100 ng/mL |

D17 DA Aggregate Plating Medium (Days 17)

| DMEM/F12 | Life Technologies | 11330-032 | 1× | 98% |
|---|---|---|---|---|
| B-27 Supplement (−VitA) | Life Technologies | 12587-010 | 2× | 2% |
| LDN-193189 | Stemgent | 04-0074 | 10 mM | 200 nM |
| CHIR99021 | Stemgent | 04-0004 | 20 mM | 3.0 µM |
| FGF8 | R&D Systems | 423-F8 | 50 µg/mL | 100 ng/mL |

TABLE 6-continued

Condition 9 (200 nM LDN)

| Component | Vendor | Cat# | Stock | Final Conc. |
|---|---|---|---|---|
| Blebbistatin | Sigma | B0560 | 10,000× | 2.5 µM |
| DA Maturation Medium (Days 18+) | | | | |
| Neurobasal | Life Technologies | 21103-049 | 1× | 98% |
| Glutamax | Life Technologies | 35050-061 | 200 mM | 2 mM |
| B-27 Supplement (−VitA) | Life Technologies | 12587-010 | 2× | 2% |
| Ascorbic Acid | Sigma | A4403 | 200 mM | 200 µM |
| Rec Hu BDNF | R&D Systems | 248-BD | 20 µg/mL | 20 ng/mL |
| Rec Hu GDNF | R&D Systems | 212-GD | 20 µg/mL | 20 ng/mL |
| Rec Hu TGFB3 | R&D Systems | 243-B3 | 10 µg/mL | 1 ng/mL |
| dbcAMP | Sigma | D0627 | 100 mM | 500 µM |
| DAPT | Sigma | D5942 | 20 mM | 5 µM |
| DA Maturation Medium + MMC (Days 27 and 29) | | | | |
| Neurobasal | Life Technologies | 21103-049 | 1× | 98% |
| Glutamax | Life Technologies | 35050-061 | 200 mM | 2 mM |
| B-27 Supplement (−VitA) | Life Technologies | 12587-010 | 2× | 2% |
| Ascorbic Acid | Sigma | A4403 | 200 mM | 200 µM |
| Rec Hu BDNF | R&D Systems | 248-BD | 20 µg/mL | 20 ng/mL |
| Rec Hu GDNF | R&D Systems | 212-GD | 20 µg/mL | 20 ng/mL |
| Rec Hu TGFB3 | R&D Systems | 243-B3 | 10 µg/mL | 1 ng/mL |
| dbcAMP | Sigma | D0627 | 100 mM | 500 µM |
| DAPT | Sigma | D5942 | 20 mM | 5 µM |
| Mitomycin C | Sigma | M4287 | 1 mg/mL | 100 ng/mL |
| DA Quench Medium 2 (Days 18+) | | | | |
| Neurobasal | Life Technologies | 21103-049 | 1× | 98% |
| Glutamax | Life Technologies | 35050-061 | 200 mM | 2 mM |
| B-27 Supplement (−VitA) | Life Technologies | 12587-010 | 2× | 2% |
| Blebbistatin | Sigma | B0560 | 10,000× | 2.5 µM |
| DA Maturation Plating Medium (Days 18+) | | | | |
| Neurobasal | Life Technologies | 21103-049 | 1× | 98% |
| Glutamax | Life Technologies | 35050-061 | 200 mM | 2 mM |
| B-27 Supplement (−VitA) | Life Technologies | 12587-010 | 2× | 2% |
| Ascorbic Acid | Sigma | A4403 | 200 mM | 200 µM |
| Rec Hu BDNF | R&D Systems | 248-BD | 20 µg/mL | 20 ng/mL |
| Rec Hu GDNF | R&D Systems | 212-GD | 20 µg/mL | 20 ng/mL |
| Rec Hu TGFB3 | R&D Systems | 243-B3 | 10 µg/mL | 1 ng/mL |
| dbcAMP | Sigma | D0627 | 100 mM | 500 µM |
| DAPT | Sigma | D5942 | 20 mM | 5 µM |
| Blebbistatin | Sigma | B0560 | 10,000× | 2.5 µM |

Example 2

Efficient mDA Progenitor Patterning Using Mono-SMADi

Efficient patterning of mDA progenitors, as measured by the percentage of cells co-expressing FoxA2 and Lmx1 on process day 17, is generally required for obtaining a highly enriched population of mDA neurons at the end of the manufacturing process. If the majority of the cells on day 17 are not mDA progenitors, the neurons obtained will have a large population of non-midbrain phenotype neurons, or will have an outgrowth of proliferative cells that typically leads to neuron detachment or difficulties or an inability to purify the post-mitotic neurons.

Figure 2:
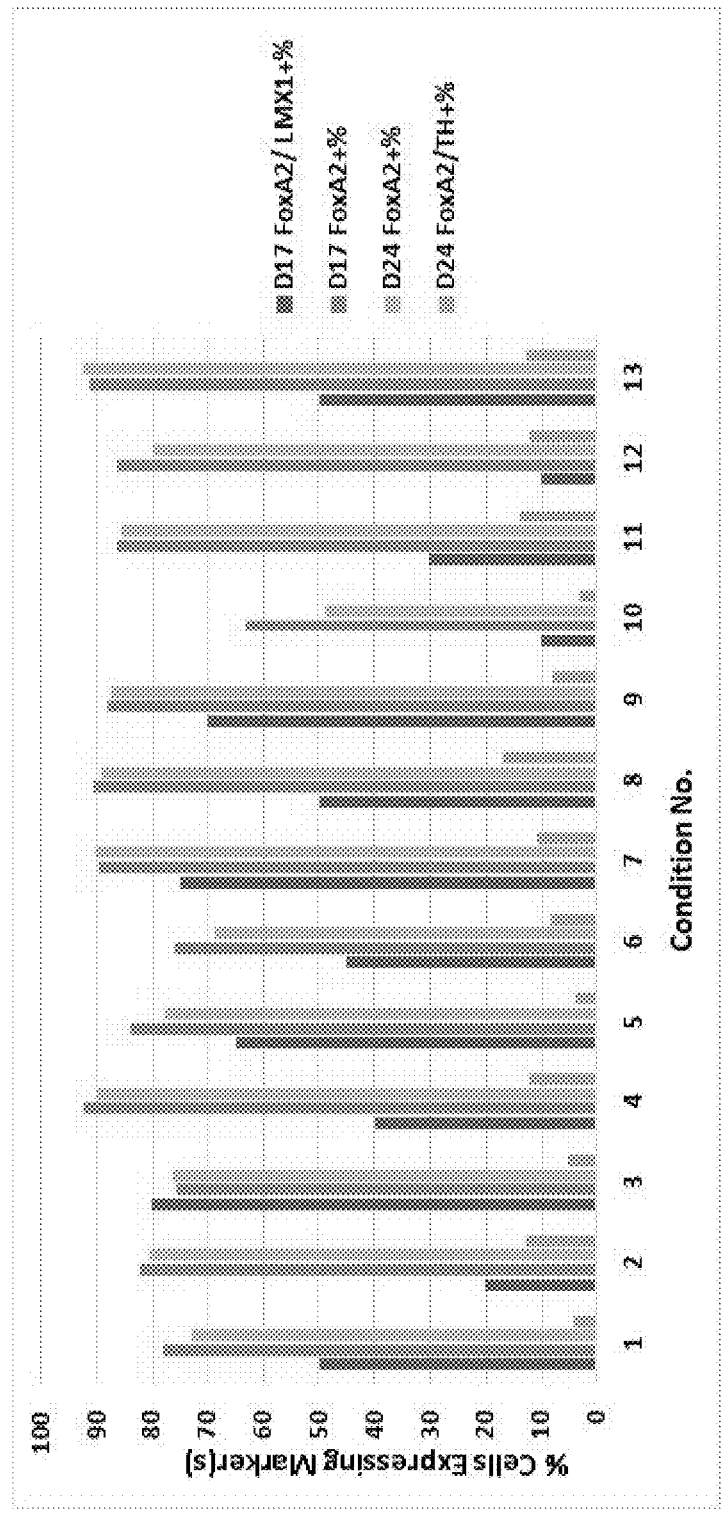
FIG. 2: Marker expression by dopaminergic progenitor cells (immature mDA neurons) on Day 17 (D17) and Day 24 (D24).

The iCell DopaNeurons process was optimized with most progenitor patterning factors added starting on day 1. This includes factors for neuralization (dual-SMADi), sonic hedgehog signaling (Shh, PMN), and Wnt signaling (CHIR). However, the inventors found that this approach did not work well for almost all iPSC lines tested in the context of neuralization using mono-SMAD inhibition. A large number of optimization experiments were carried out across several iPSC lines to define conditions for efficient mono-SMADi mDA progenitor patterning, varying the timing and dose of all patterning factors. As shown in FIG. 1, conditions were found ("MONO/ALT") where mono-SMADi mDA progenitor patterning was as good as dual-SMADi patterning using previously-optimized standard conditions ("DUAL/STD"), and the patterning was markedly more efficient than mono-SMADi mDA progenitor patterning using the standard conditions ("MONO/STD"). In the alternate (ALT) method, the SHH/Purmophamine addition was moved from Day 1 to Day 2. The changes utilized in this improvement included: (i) staggering the addition of the Wnt agonist (CHIR) to day 2 or day 3, (ii) re-optimizing the CHIR concentration, as this is dependent on the time it is first added, and (iii) moving the window where PD03 is added, as the optimal window depends on when CHIR is added. The end result was a narrow set of conditions that led to highly-efficient mDA progenitor formation in multiple iPS cell lines. Approximately half of the iPSC lines tested were able to generate mDA progenitors using mono-SMADi conditions. FIG. 2 shows an example of a matrix optimization experiment used to define optimized patterning conditions.

As shown in FIG. 1, the patterning of mDA progenitors from three different iPSC lines was evaluated on process day 17 by measuring the proportion of total cells expressing FoxA2 (by flow cytometry) or co-expressing FoxA2 and Lmx1 (by ICC). FoxA2/Lmx1 coexpression is the most accurate marker for mDA progenitor cells. The use of alternate patterning conditions allows for efficient mDA progenitor patterning in the context of mono-SMAD inhibition ("Mono/Alternate"), whereas the standard patterning conditions have poor mDA progenitor patterning in the context of mono-SMAD inhibition ("Mono/Standard"). Control differentiations using dual-SMADi and standard patterning conditions ("Dual/Standard") are shown for comparison.

FIG. 1 data represents data obtained from using the conditions described in Table 1 for all Dual Standard conditions. Cell line C data was obtained using conditions described in Table 4 for Mono Alternate and Table 3 for Mono Standard conditions. Cell lines D and K followed Table 2 and Table 5 for Mono Standard and Mono Alternate, meaning that data from cell line C was obtained from testing LDN while the other lines were tested with Dorsomorphin.

Once an alternate patterning condition was identified that allowed for successful differentiation using mono-SMAD inhibition (Condition 1, i.e., Table 4: Alternate, LDN at 200 nM), the method was refined using a matrix of conditions, including the concentration of CHIR, and the treatment windows for Shh signaling, Wnt signaling, and MEK inhibition. As shown in FIG. 2, the following conditions were tested for mono-SMAD inhibition, as shown in Table 6 below. Table 6 shows the start day for incubation with a particular compound (e.g., "D2" indicates incubation start on day 2) and the concentration of CHIR99021 used. Shown in FIG. 2 is an example of one matrix experiment for iPSC line K. Conditions 3, 5, 7 and 9 resulted in the highest percentage of FoxA2+/Lmx1+ mDA progenitor cells by day 17, with the FoxA2+ population being maintained to day 24. Tyrosine hydroxylase (TH) expression is low in immature mDA neurons. These experiments were repeated using a concentration of CHIR99021 of 1.65 µM instead of 1.75 µM, and it was observed that similar results for the generation of mDA progenitor cells could be obtained using the lower 1.65 µM concentration of CHIR99021.

These mono-SMAD experiments were repeated, with the modification that Benzonase® (endonuclease, EMD Millipore) was included in the incubation on Day 5 at a concentration of 100 U/mL. Inclusion of the Benzonase® in the incubation on Day 5 was observed to reduce or prevent excessive clumping in the aggregate formation.

TABLE 6

Conditions for mono-SMAD inhibition

| Condition | Shh/PMN Start | PD03 Start | CHIR Start | CHIR Conc. |
|---|---|---|---|---|
| 1 | D2 | D3 | D3 | 1.75 uM |
| 2 | D2 | D2 | D2 | 1.25 uM |
| 3 | D2 | D2 | D2 | 1.75 uM |
| 4 | D2 | D3 | D2 | 1.25 uM |
| 5 | D2 | D3 | D2 | 1.75 uM |
| 6 | D1 | D2 | D2 | 1.25 uM |
| 7 | D1 | D2 | D2 | 1.75 uM |
| 8 | D1 | D3 | D2 | 1.25 uM |
| 9 | D1 | D3 | D2 | 1.75 uM |
| 10 | D1 | D2 | D3 | 1.25 uM |
| 11 | D1 | D2 | D3 | 1.75 uM |
| 12 | D1 | D3 | D3 | 1.25 uM |
| 13 | D1 | D3 | D3 | 1.75 uM |

"Shh" refers to C25II Shh;
"PMN" refers to purmorphamine;
"PD03" refers to PD0325901;
"CHIR" refers to CHIR99021;
"Conc." is concentration;
"D1", "D2", and D3 refer to days 1, 2, and 3, respectively.

Example 3

Determination of Inhibitors for Mono-SMAD Inhibition

Figure 3:
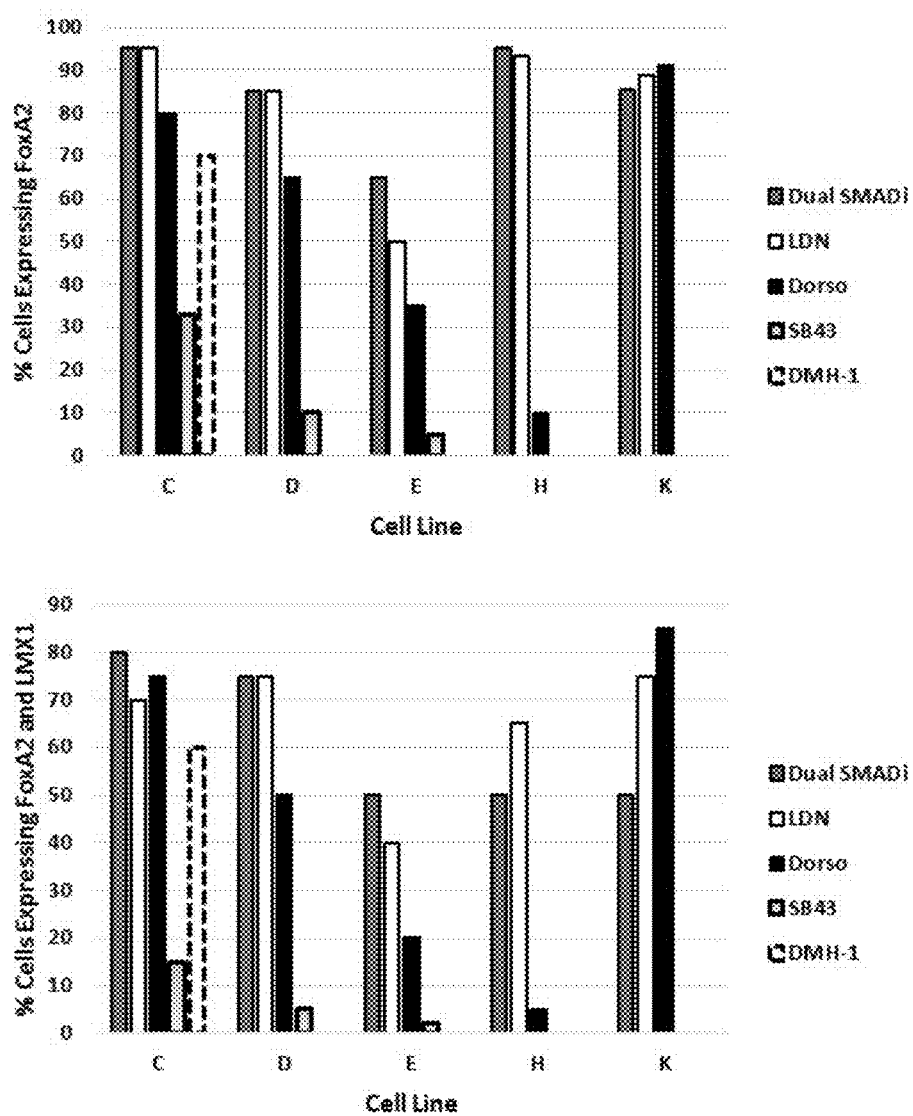
FIG. 3: Patterning of mDA progenitors generated from different human iPS cell lines on process day 17. The proportion of total cells expressing FoxA2, or co-expressing FoxA2 and Lmx1, are shown.

Different inhibitors were tested for function in mono-SMADi methods, as follows. The iCell DopaNeurons process induces neuralization using LDN-193189, an inhibitor of BMP signaling (inhibits ALK 1/2/3/6, blocks SMAD 1/5/8), and SB-431542, an inhibitor of TGF-b signaling (inhibits ALK 4/5/7, blocks SMAD 2/3). Together, this is referred to as "dual SMAD inhibition", or "dual SMADi." To define optimal conditions for neuralization using only a single SMAD inhibitor in the mDA process, various analogs of LDN-193189 and SB-431542 were screened across multiple iPS cell lines using the alternate patterning conditions described above. As shown in FIG. 3, LDN-193189 was observed to be the inhibitor that was best overall at inducing the highest percentage of mDA progenitors when tested across different iPSC lines. For the data shown with one SMAD inhibitor, LDN-193189, Dorsomorphin, and DMH-1 were added to the media for Days 1 through 17, while SB431542 was added at 20 µM to the media on Days 1 through 4.

The patterning of mDA progenitors was evaluated on process day 17 by measuring the proportion of total cells expressing FoxA2 (by flow cytometry) or co-expressing FoxA2 and Lmx1 (by ICC), and results are shown in FIG. 3. FoxA2/Lmx1 coexpression was observed to be the most accurate marker for mDA progenitor cells. LDN-193189 was observed to be the most efficient at neutralizing mDA progenitors across multiple iPSC lines. All mono-SMADi testing shown used alternate patterning conditions; dual-SMADi conditions using standard patterning are shown as controls. Also tested were the SB-431542 analogs LY364947 and A-83-01, which did not outperform LDN.

Example 4

Purification and Characterization of Dopaminergic Neurons Generated by Mono-SMADi In-Process Purification of mDA Neurons: Even with efficient mDA progenitor patterning, there is a population of cells that continues to proliferate even after the maturing mDA neurons leave the cell cycle (approximately day 25). To remove these unwanted cells, the DNA cross-linker mitomycin C (MMC) was added at low dose (50 to 500 ng/mL) for four days (days 27-31) immediately after the mDA neurons have left the cell cycle. MMC obtained from Sigma or Tocris was used in experiments. The dose and duration used has little or no adverse effects on the post-mitotic mDA neurons, but kills dividing cells. This approach was optimized by testing various compounds toxic to dividing cells, and varying the dose, duration, and start date of MMC treatment. It should also be noted that much higher MMC doses given for much shorter times can achieve the same effect (killing dividing cells), for instance 5 ug/mL for 1 h. Intermediate doses given for intermediate times could also be used to achieve a similar effect. However, use of a lower concentration of about 100 ng/mL was used over four days and was observed to result in removal of dividing cells with no observed toxicity to post-mitotic neurons.

As shown in FIG. 4A, without purification, a significant population of proliferating cells (nestin+) has grown out by day 37, resulting in a post-mitotic neuron purity (MAP2+/nestin−) of 44% ("No selection"). The iCell DopaNeurons product utilizes a genetic construct with the neoR gene driven by the MAP2 promoter to permit efficient selection of post-mitotic neurons ("G418 drug selection"), but this approach typically may not be appropriate for clinical use. However, use of the chemotherapeutic drug MMC was used to purify post-mitotic neurons, consistently resulting in a final neuron purity of >90% ("Chemo drug selection"). As shown in FIG. 4B, the functionality of mDA neurons was retained after MMC selection, as illustrated by the ability to secrete dopamine, and other testing did not reveal any differences from genetically selected cells, the extensively characterized iCell DopaNeurons. Importantly, there is no outgrowth of proliferating cells after MMC selection, even after extended post-thaw culturing (FIG. 4C).

Figure 5:
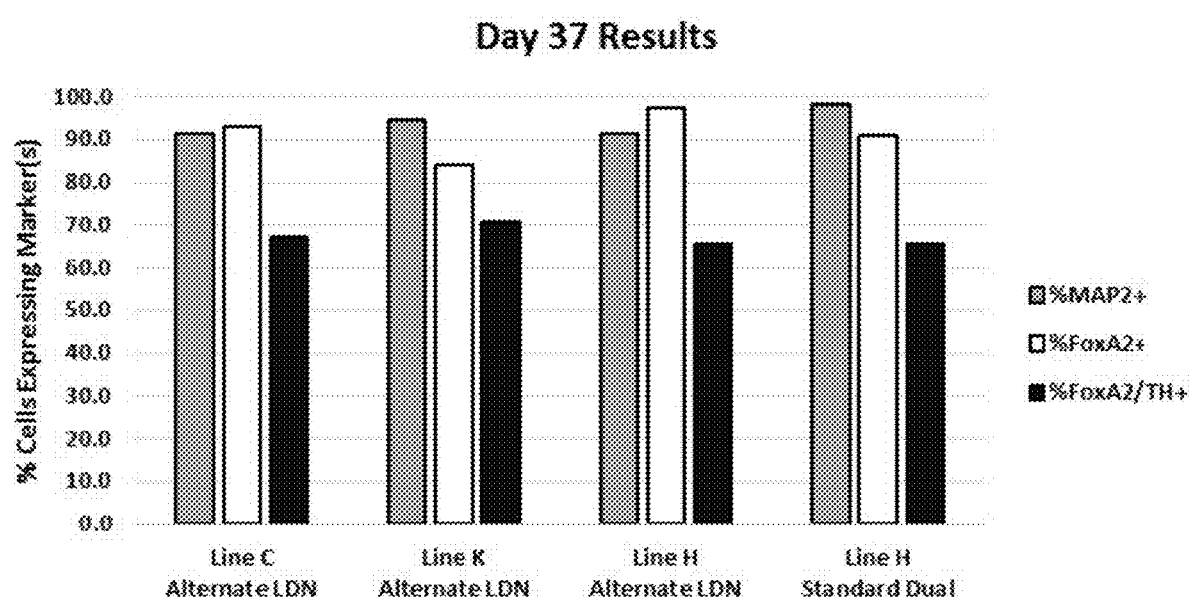
FIG. 5: Expression of markers in cells produced from lines of human iPS cells.

Final purity and cryopreservation of midbrain dopaminergic (mDA) neurons: Multiple iPSC lines were differentiated to reach process completion, using the methods described: mono-SMAD inhibition, alternate mDA progenitor patterning, and MMC purification. Results are shown in FIG. 5. Three iPSC lines (C, K, and H) are shown as examples of successful differentiations taken to process completion (day 37) (FIG. 5). The iPSC lines C, K, and H are iPSC lines (21526.101, 21534.101, and 21531.101, respectively). Data was obtained using the approach in Table 4 for Alternate LDN and Table 1 for Standard Dual control. These experiments utilized LDN-193189 for mono-SMADi and one of the alternate patterning variations shown in FIG. 2. Differentiation of the H line using dual-SMADi and the optimized standard patterning is shown for comparison. In each case, a high level of neuron purity was observed (>90% MAP2+/nestin−), and essentially all neurons co-express FoxA2. The inventors have observed that the vast majority of MAP2+/FoxA2+ cells at this stage also express Lmx1, and are therefore mDA neurons. The DA neuron phenotype was confirmed by the expression of tyrosine hydroxylase (TH) in the majority of neurons, a marker of more mature DA neurons.

As shown in FIG. 6, mDA neurons made from Line K were cryopreserved and thawed for post-thaw characterization. Data shown in FIG. 6 was obtained using the approach as shown in Table 6. Cell viability was observed to be high at thaw, and the majority of viable cells were able to plate down onto a PLO-laminin surface (plating efficiency, FIG. 6). In addition, the post-thaw cells retain the mDA neuron phenotype of MAP2+/FoxA2+/TH+, as measured at 3 days post-thaw. The cells exhibited healthy neurite outgrowth, and proliferating cells were observed to be absent. These phenotypic characteristics closely match what was seen with post-thaw iCell DopaNeurons.

Example 5

Cross-iPSC Line Testing of Mono-SMADi Differentiation Process

Figure 7A:
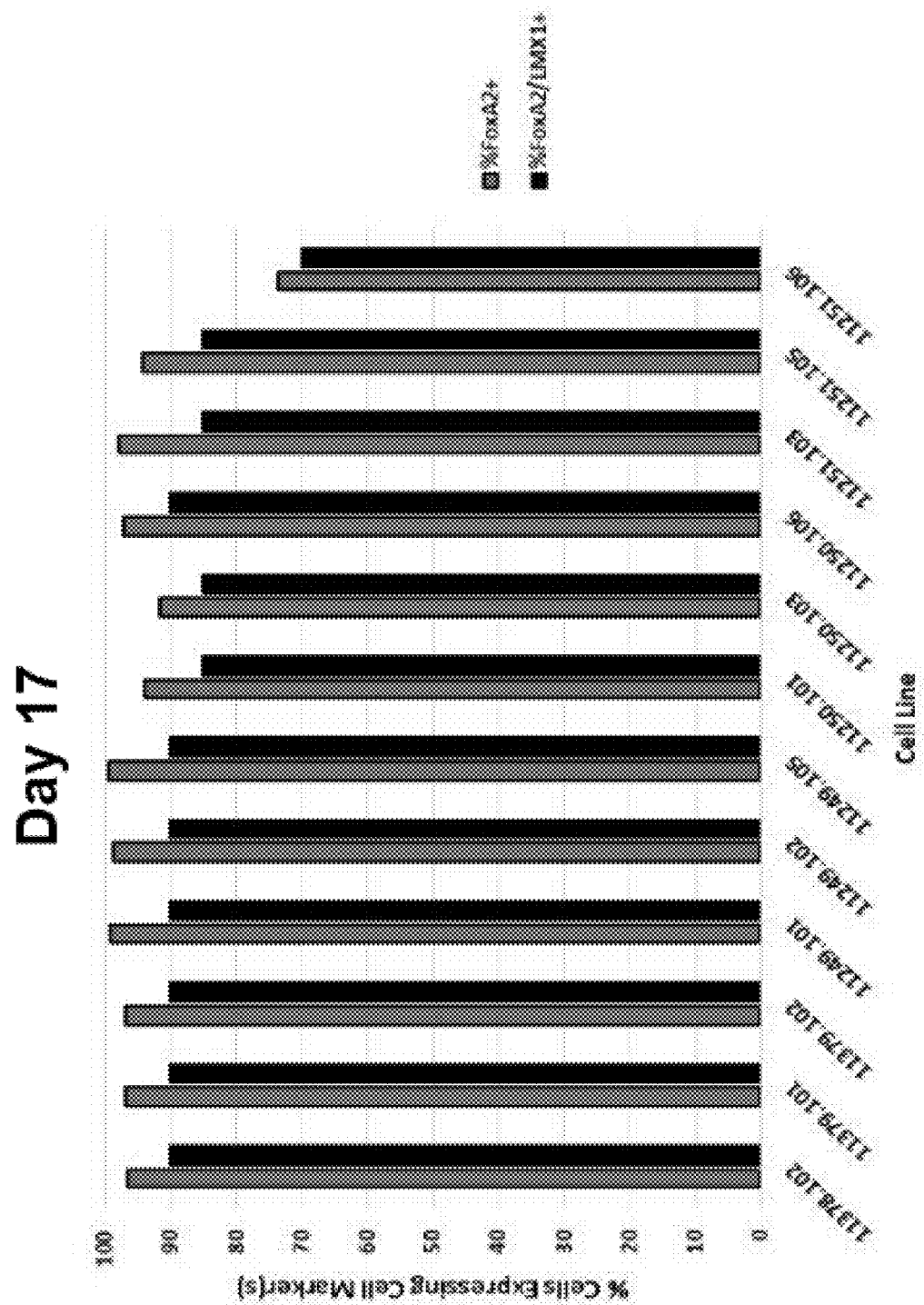
FIGS. 7A-B: Cross-iPSC line testing of mono-SMADi differentiation process. Three iPSC lines derived from healthy donors and nine iPSC lines derived from Parkinson's disease patients were differentiated using the optimized mono-SMADi process. All iPSC lines were efficiently converted to DA progenitor cells by process day 17, with >80% FoxA2/Lmx1 co-expression in 11 of 12 lines (FIG. 7A). By process completion (day 37), the cells from all iPSC lines had achieved a high level of neuron purity (>90% MAP2+/nestin−), midbrain specification (>80% FoxA2+), and midbrain dopamine neuron maturation (>40% TH+) (FIG. 7B).
Figure 7B:
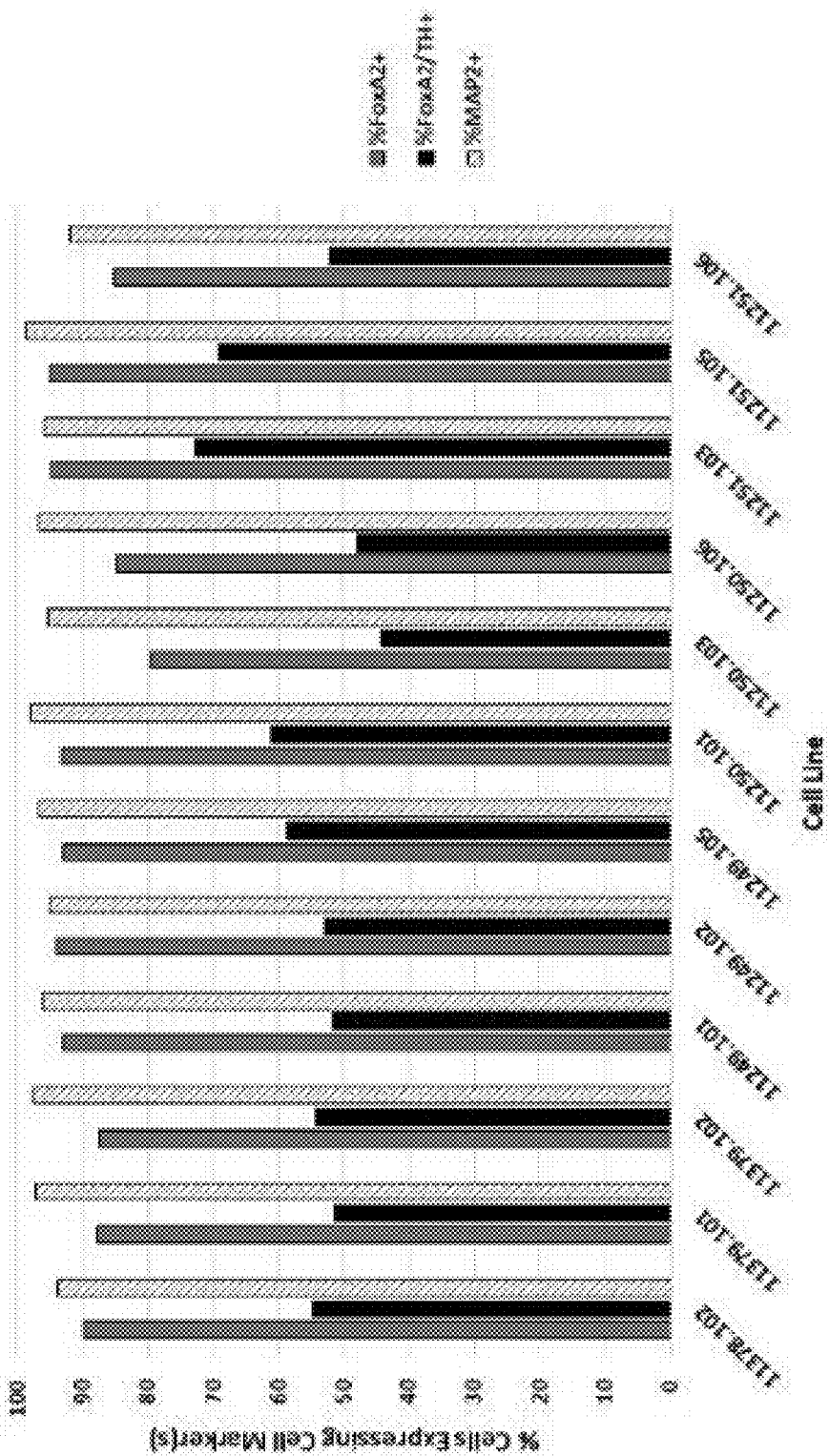

Three iPSC lines derived from healthy donors (donor IDs 11378 and 11379) and nine iPSC lines derived from Parkinson's disease patients (donor IDs 11249, 11250 and 11251) were differentiated using the optimized mono-SMADi process ("Condition 9" from FIG. 2). All iPSC lines were efficiently converted to DA progenitor cells by process day 17, with >80% FoxA2/Lmx1 co-expression in 11 of 12 lines (FIG. 7A). By process completion (day 37), the cells from all iPSC lines had achieved a high level of neuron purity (>90% MAP2+/nestin−), midbrain specification (>80% FoxA2+), and midbrain dopamine neuron maturation (>40% TH+) (FIG. 7B). These results demonstrate the robustness of the optimized single-SMADi differentiation protocol across iPSC lines, including those derived from Parkinson's disease patients.

Example 6

Flow Cytometry Assay for FoxA2 Lmx1 Co-Expression

Figure 8:
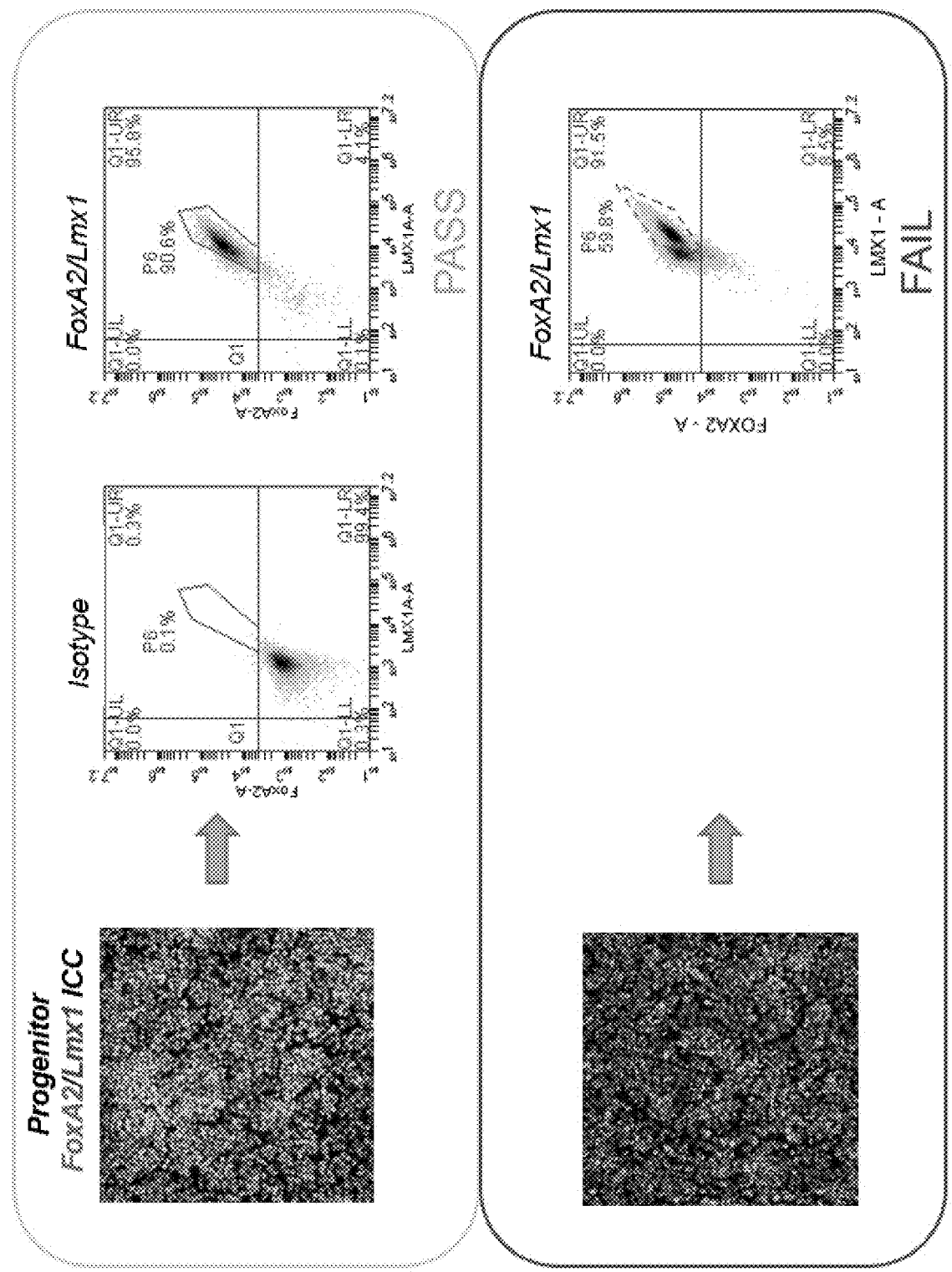
FIG. 8: Flow Cytometry assay for FoxA2/Lmx1 co-expression. Progenitor patterning is considered successful when the cells are >80% FoxA2+/Lmx1+ on day 17 (FIG. 8, top). An example of a sub-standard progenitor patterning is shown (FIG. 8, bottom), with 60% FoxA2+/Lmx1+ cells and a significant population of FoxA2+/Lmx1-negative cells.

FoxA2/Lmx1 co-expression is a critical readout for successful dopamine neuron progenitor patterning, and therefore an intracellular flow cytometry assay was developed that is less subjective and variable than results derived using cell counting software run on immunocytochemistry images. The assay can accurately quantify the percentage of cells co-expressing FoxA2 and Lmx1 on process day 17 to day 24, with results that correlate to counts from analyzed ICC images. Progenitor patterning is considered successful when the cells are >80% FoxA2+/Lmx1+ on day 17 (FIG. 8, top). An example of a sub-standard progenitor patterning is shown (FIG. 8, bottom), with 60% FoxA2+/Lmx1+ cells and a significant population of FoxA2+/Lmx1-negative cells.

Example 7

Figure 9:
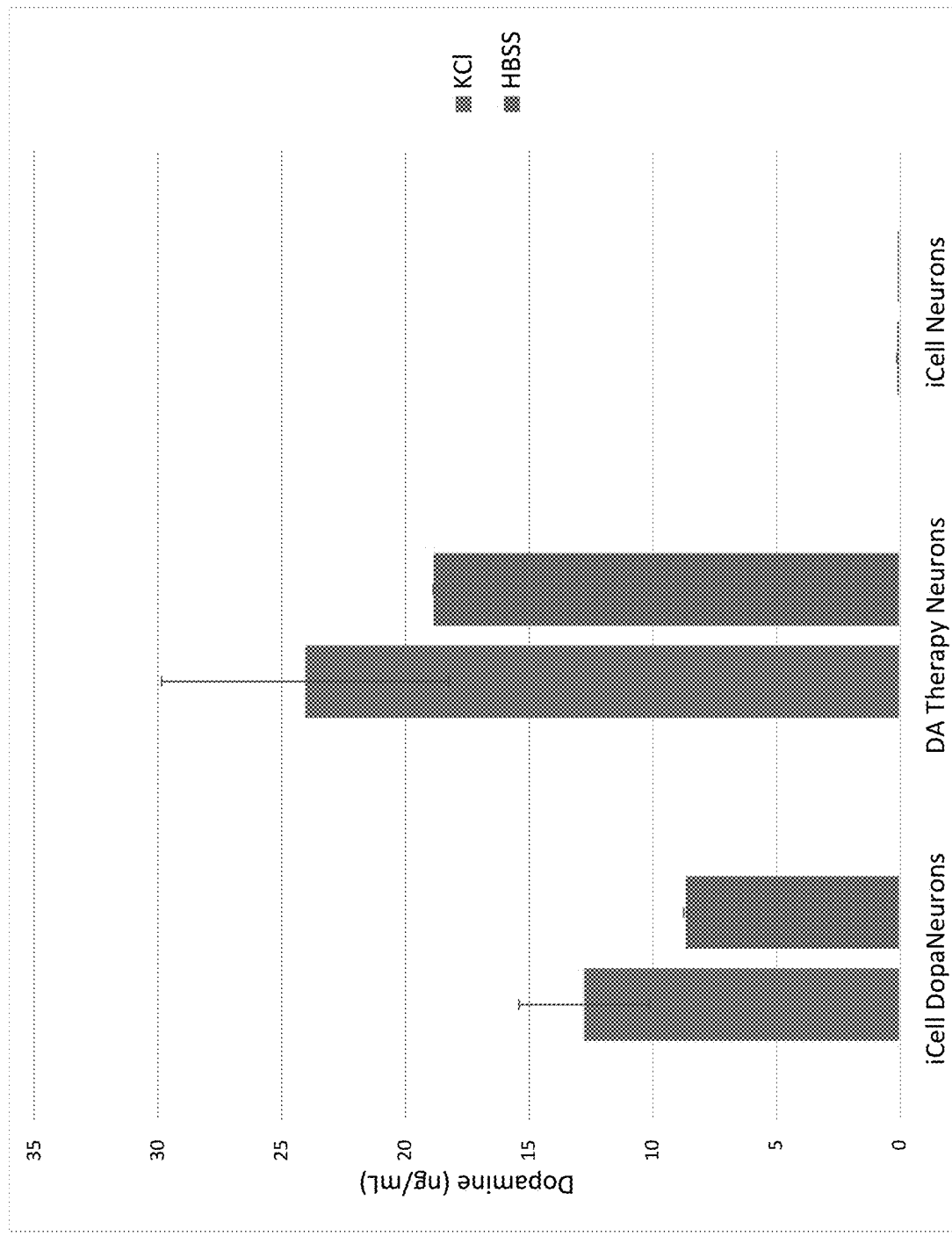
FIG. 9: Dopamine release from iPSC-mDA neurons. iPSC line "K" was differentiated to process completion (day 37) using the optimized mono-SMADi protocol ("Condition 9") and cryopreserved. No dopamine release was detected from iPSC-derived forebrain neurons (iCell Neurons). Conversely, iPSC-mDA cells derived using the optimized mono-SMADi process (DA Therapy Neurons) secreted as least as much dopamine as cells derived using the optimized dual-SMAD process (iCell DopaNeurons).

Dopamine Release from iPSC-mDA Neurons iPSC line "K" was differentiated to process completion (day 37) using the optimized mono-SMADi protocol ("Condition 9") and cryopreserved. Cells were thawed and plated at high density ($8.8 \times 10^5$/cm$^2$). The cells were fed with Maturation Medium without DAPT every third day for a total of 14 days. On the assay day, cells were washed and incubated 30 min with HBSS (with or without 56 mM KCl). The dopamine concentration in the release solution was determined using a competitive dopamine ELISA kit (Eagle Biosciences). No dopamine release was detected from iPSC-derived forebrain neurons (iCell Neurons). Conversely, iPSC-mDA cells derived using the optimized mono-SMADi process (DA Therapy Neurons) secreted as least as much dopamine as cells derived using the optimized dual-SMAD process (iCell DopaNeurons). Thus, the cells are able to perform a key functional attribute of mature dopamine neurons. Results are shown in FIG. 9.

Example 8

Electrical Activity of iPSC-mDA Neurons

Figure 10:
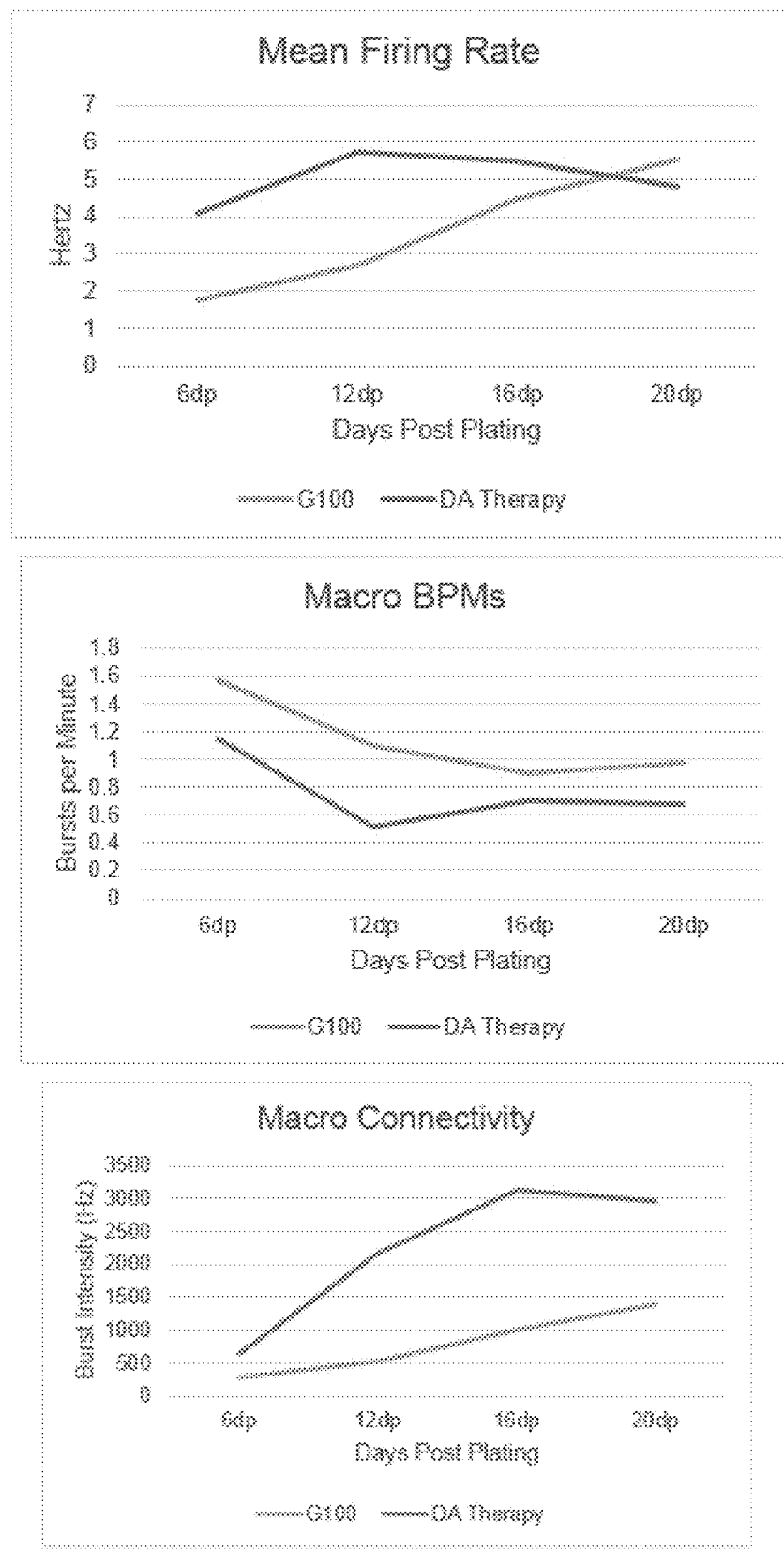
FIG. 10: Electrical activity of iPSC-mDA neurons. Cryopreserved iPSC-mDA neurons were thawed and plated onto PEI-coated 48-well multielectrode array (MEA) plates. Neurons made with the optimized mono-SMADi protocol (DA Therapy) demonstrated similar electrical activity compared to cells made with the optimized dual-SMADi protocol (iCell Dopa G100), including mean firing rate (mFR), bursting (macro BPMs) and connectivity (Top graphs). mFR frequency and connectivity burst intensity increased with time, plateauing by approximately day 16 post-thaw. Temporal Raster plots show clean inter-spike intervals, high burst intensities, and bursting across all electrodes in a well, demonstrating a high degree of electrical activity.
Figure 10:
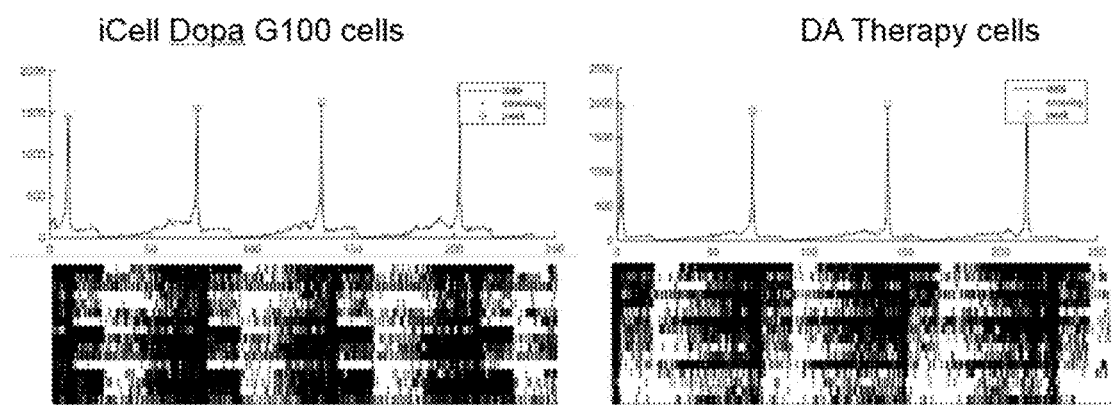

Cryopreserved iPSC-mDA neurons were thawed and plated onto PEI-coated 48-well multielectrode array (MEA) plates. Cells were cultured according to the Cellular Dynamics Intl application protocol "Measuring synchronous neuronal activity on the Maestro multielectrode array" in U.S. application Ser. No. 14/830,162. Neurons made with the optimized mono-SMADi protocol "Condition 9" (DA Therapy) demonstrated similar electrical activity compared to cells made with the optimized dual-SMADi protocol (iCell Dopa G100), including mean firing rate (mFR), bursting (macro BPMs) and connectivity (FIG. 10, top graphs). Mean firing rate (mFR), frequency, and connectivity burst intensity increased with time, plateauing by approximately day 16 post-thaw. Temporal Raster plots showed clean inter-spike intervals, high burst intensities, and bursting across all electrodes in a well, demonstrating a high degree of electrical activity. Results are shown in FIG. 10.

Example 9

Quantitative Gene Expression Profile of iPSC-mDA Neurons

Figure 11:
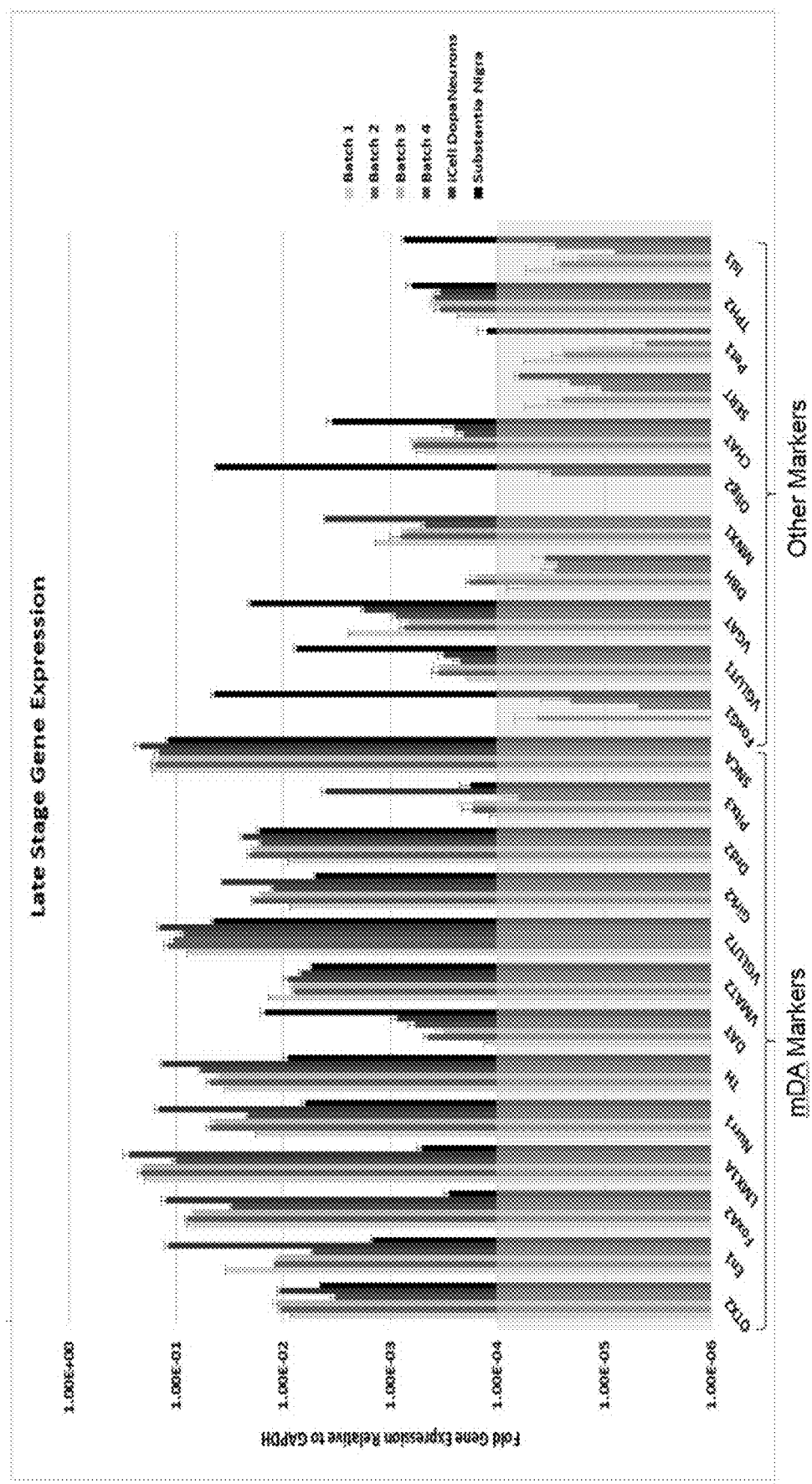
FIG. 11: Quantitative gene expression profile of iPSC-mDA neurons. RNA was extracted from four batches of iPSC-mDA cells derived using the optimized mono-SMADi process (Batch 1-4) and one batch of iPSC-mDA cells derived using the optimized dual-SMADi protocol (iCell DopaNeurons) on process day 37. After RNA isolation, real-time quantitative polymerase chain reaction (PCR) was performed, with results expressed as relative expression to GAPDH control. Values<$10^{-4}$ are considered background (shaded box). Expression of midbrain and mDA neuron markers were similar between batches and between cells made using the different protocols. Markers for non-midbrain regions or non-mDA cell types were low, and also similar between mono-SMADi and dual-SMADi-derived cells.

RNA was extracted from four batches of iPSC-mDA cells derived using the optimized mono-SMADi process (Batch 1-4) and one batch of iPSC-mDA cells derived using the optimized dual-SMADi protocol (iCell DopaNeurons) on process day 37. After RNA isolation, real-time quantitative polymerase chain reaction (PCR) was performed using TaqMan Gene Expression Assays (Applied Biosystems), with results expressed as relative expression to GAPDH control. Values<$10^{-4}$ are considered background (shaded box). Expression of midbrain and mDA neuron markers were similar between batches and between cells made using the different protocols. Markers for non-midbrain regions or non-mDA cell types were low, and also similar between mono-SMADi and dual-SMADi-derived cells. Results are shown in FIG. 11.

Example 10

Conversion to cGMP-Compatible Reagents

Figure 12:
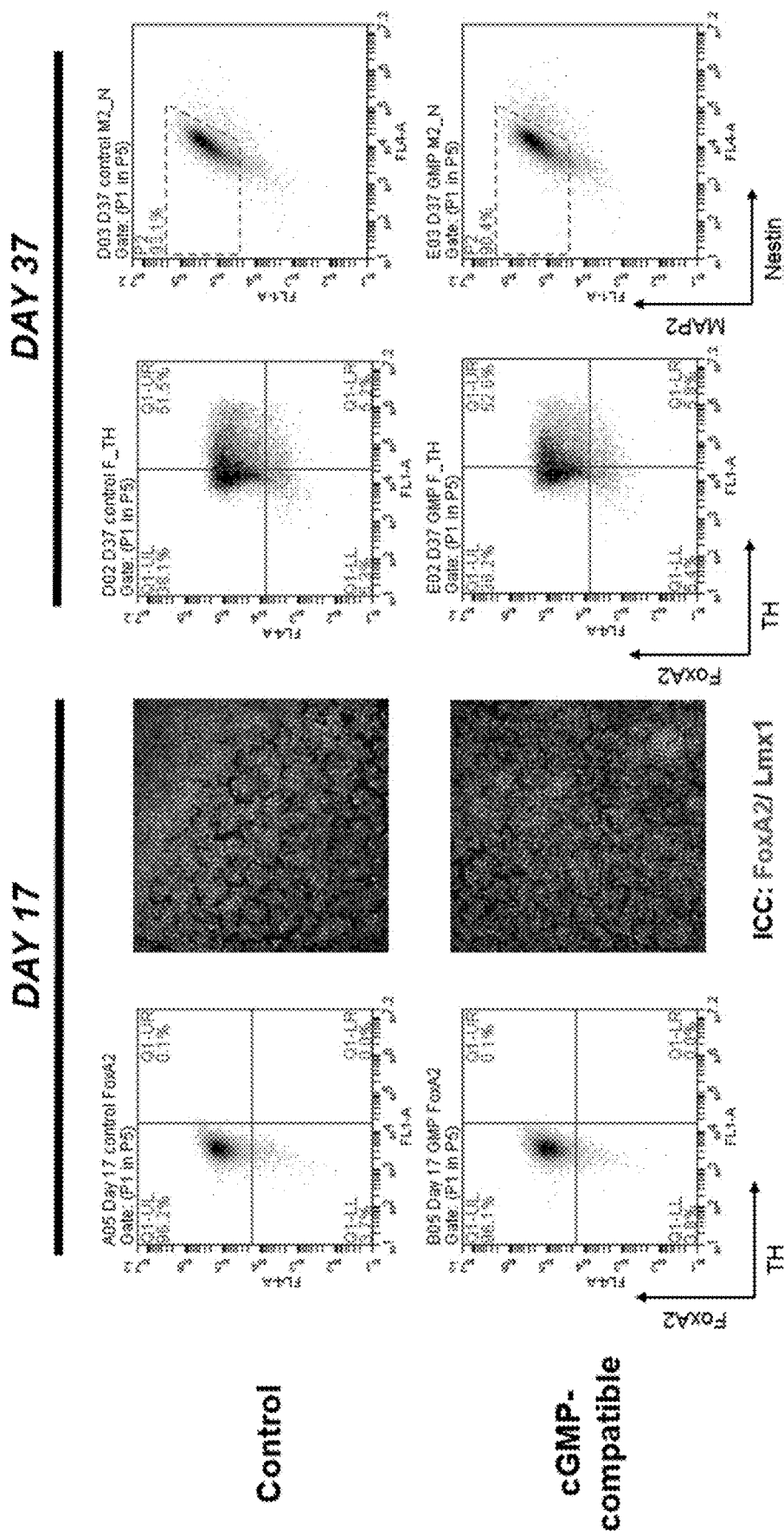
FIG. 12: Conversion to cGMP-compatible reagents. iPSC-mDA cells were differentiated using the mono-SMADi process using standard reagents or cGMP-compatible reagents, resulted in equivalent progenitor patterning (day 17) and day 37 mDA neuron purity.

To convert the mono-SMADi iPSC-mDA differentiation protocol to a cGMP-compatible process for cell therapy, it was preferred or necessary to replace multiple reagents that contained animal-derived components, contained unacceptable levels or endotoxin, or were otherwise incompatible with cGMP cell manufacturing for therapeutics. iPSC-mDA cells were differentiated using the optimized mono-SMADi process ("Condition 9"), and in addition the following xeno-free, cGMP compatible reagents were used: recombinant human vitronectin, laminin, sonic hedgehog, FGF-8, GDNF, BDNF, and TGF-b3; endotoxin-free dbcAMP. B27 and B27 (-Vit. A) are the only reagents used in the process containing animal components. K line iPSC cells differentiated using the "Condition 9" process, with standard reagents or cGMP-compatible reagents, had equivalent progenitor patterning (day 17) and day 37 mDA neuron purity. Results are shown in FIG. 12.

Example 11

Figure 13:
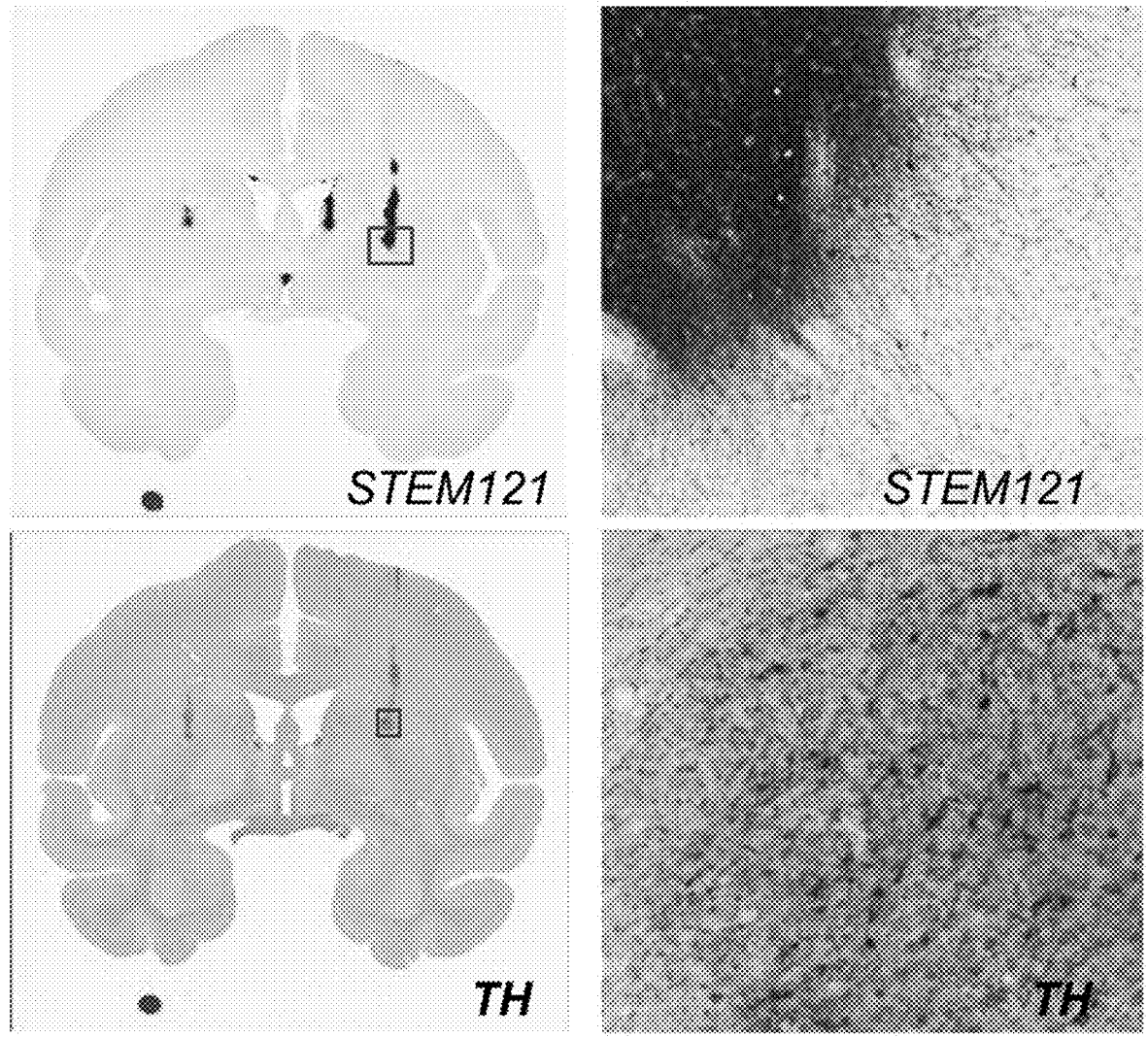
FIG. 13: Engraftment of iPSC-DA neurons in non-human primates. Staining of human cytoplasm (STEM121) reveals good human cell engraftment and innervation in all animals. Dopamine neurons (TH+) were observed in the grafts, demonstrating the ability of these cells to survive long-term and innervate the mDA neuron target structure in the brain. No tumors, neural outgrowth, or other adverse effects were observed in these animals.

Engraftment of iPSC-DA Neurons in Non-Human Primates iPSC line "K" was differentiated to process completion (day 37) using the optimized protocol ("Condition 9") and cryopreserved. Cells were thawed and transplanted bilaterally to the caudate and putamen ($1.5 \times 10^6$ cells/injection) of MPTP-treated and immunosuppressed African Green Monkeys (n=3). After 3 months, engraftment and innervation of the neurons was assessed by histology of coronal sections. Staining of human cytoplasm (STEM121) reveals good human cell engraftment and innervation in all animals. Dopamine neurons (TH+) were observed in the grafts, demonstrating the ability of these cells to survive long-term and innervate the mDA neuron target structure in the brain. No tumors, neural outgrowth, or other adverse effects were observed in these animals. Results are shown in FIG. 13.

Example 12

Figure 14:
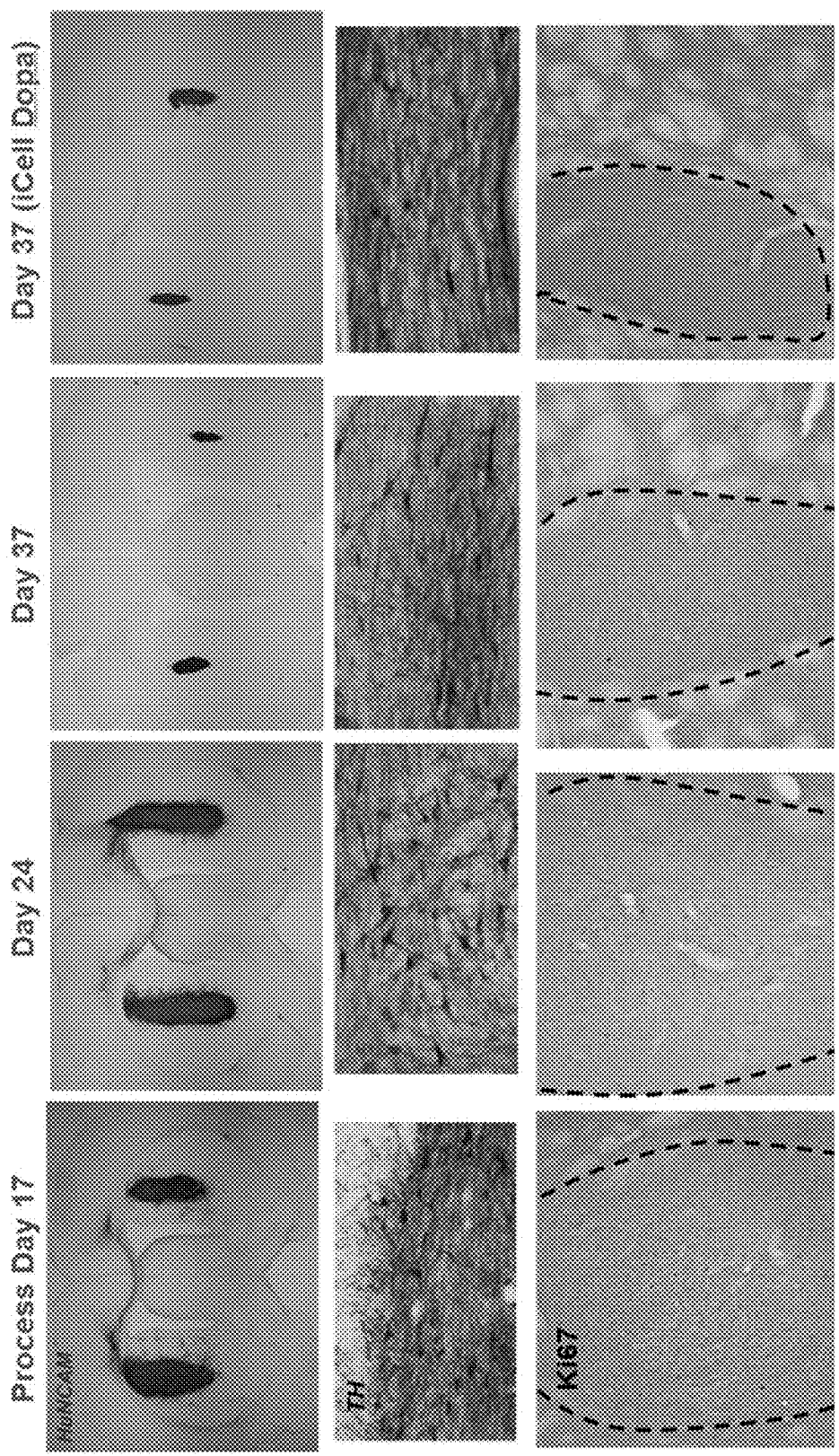
FIG. 14: Engraftment of iPSC-DA progenitors and neurons in rat PD model system. No tumors, neural outgrowth, or other adverse effects were observed in any of these animals. The results support the idea that cells drawn from earlier in the optimized mono-SMADi differentiation process (day 17-24) are better able to engraft and innervate, as compared to more mature cells.

Engraftment of iPSC-DA Progenitors and Neurons in Rat Parkinson's Disease Model System iPSC line "K" was differentiated using the optimized mono-SMADi protocol ("Condition 9") and cryopreserved at different stages of the differentiation process (Day 17, day 24, and Day 37). In addition, iPSC-mDA cells derived using the optimized dual-SMADi protocol (iCell Dopa) were cryopreserved on process day 37. Cells were thawed and transplanted bilaterally to the striatum ($4.5 \times 10^5$ cells/injection) of 6-OHDA-treated but asymptomatic nude (RNU) rats (n=3 per group). After 3 months, engraftment and innervation of the cells was assessed by histology of coronal sections. Although neuron engraftment and innervation was observed in all four groups (Human NCAM stain), the iPSC-DA progenitor cells (day 17) and immature mDA neurons (day 24) had much larger grafts and greater innervation compared to the more mature mono-SMADi and dual-SMADi-derived mDA neurons (day 37 and day 37 iCell Dopa, respectively). In addition, larger numbers of DA neurons (TH+) were observed in the progenitor and immature DA neuron grafts. Ki67 staining revealed almost no proliferative cells in the grafts from day 37 cells, and few Ki67+ cells in the grafts from day 17 and day 24 cells. No tumors, neural outgrowth, or other adverse effects were observed in any of these animals. These results suggest that cells drawn from earlier in the optimized mono-SMADi differentiation process (day 17-24) are better able to engraft and innervate compared to more mature cells. Results are shown in FIG. 14.

Example 13

Figure 15:
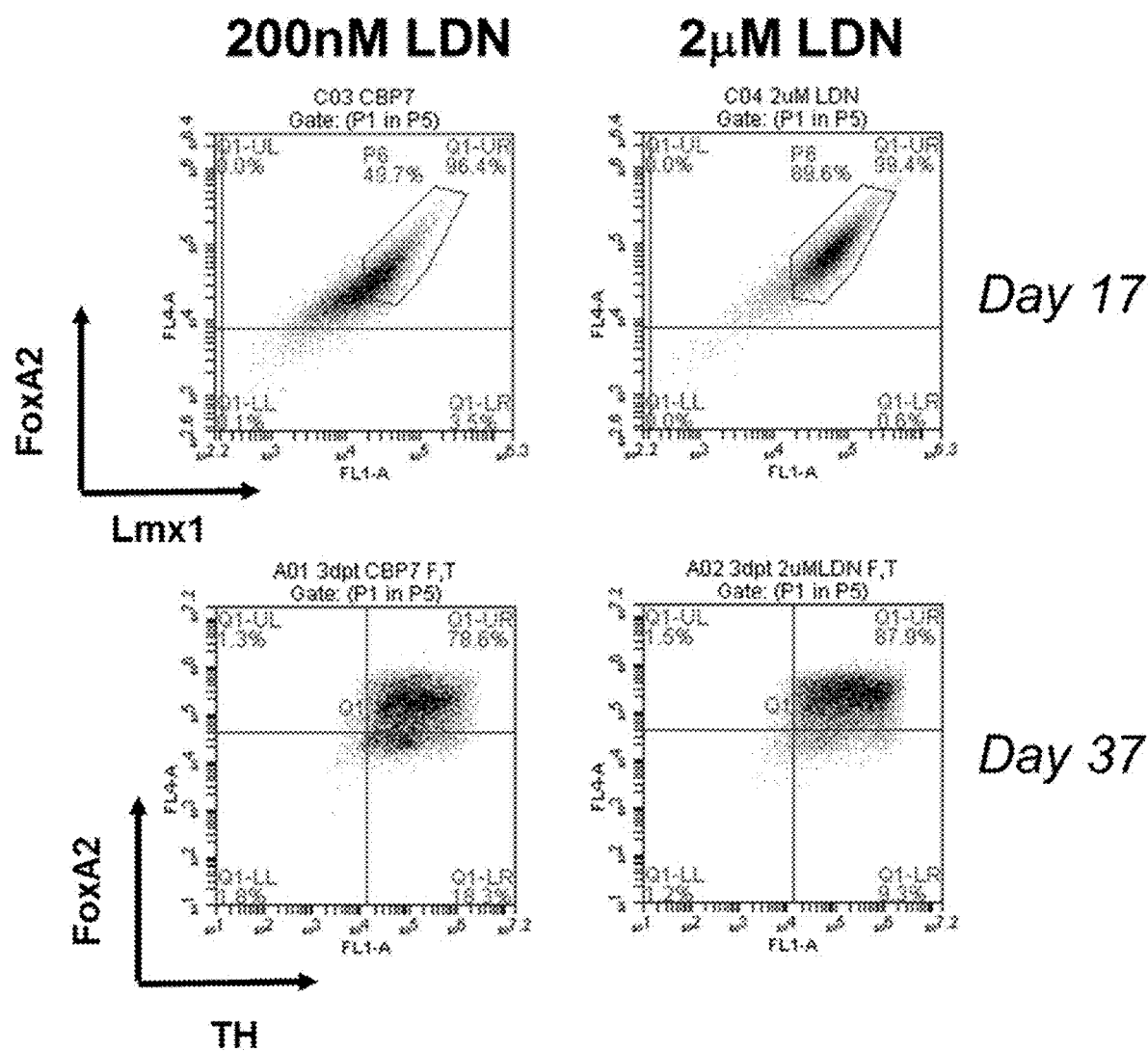
FIG. 15: Improved differentiation using 2 µM LDN-193189. In multiple experiments (n=5), improvements were seen in the quality of the differentiations when using 2 µM LDN. Higher FoxA2 and Lmx1 expression levels in day 17 progenitors (FIG. 15, top), and a higher percentage of floor plate-derived neurons (FoxA2+) on process day 37 (FIG. 15, bottom) were observed as a result of using 2 µM LDN in the protocol.

Improved Differentiation Using 2 μM LDN-193189 iPSC line "K" was differentiated using the mono-SMADi protocols "Condition 7" or "Condition 9" (as described above), using either the standard concentration of LDN-193189 (200 nM), or a ten-fold higher concentration (2 μM LDN). In multiple experiments (n=5), improvements were seen in the quality of the differentiations when using 2 μM LDN. For example, 2 μM LDN improvements to the "Condition 7" protocol include higher FoxA2 and Lmx1 expression levels in day 17 progenitors (Top), and a higher percentage of floor plate-derived neurons (FoxA2+) on process day 37 (Bottom). This suggests that 2 μM LDN improves the robustness of the differentiation process, perhaps due to the ability of LDN to inhibit TGF-β type 1 (ALK4/5/7) receptor signaling at high concentrations ($IC_{50}$>500 nM, Yu et al. 2008). Results are shown in FIG. 15.

\* \* \*

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,843,780
U.S. Pat. No. 6,200,806
U.S. Pat. No. 6,833,269
U.S. Pat. No. 7,029,913
U.S. Patent Publn. 2002/0168766
U.S. Patent Publn. 2003/0022367
U.S. Patent Publn. 2003/0211603
U.S. Patent Publn. 20030087919
U.S. Patent Publn. 20030125344
U.S. Patent Publn. 20040002507
U.S. Patent Publn. 20040002508
U.S. Patent Publn. 20040014755
U.S. Patent Publn. 20050192304
U.S. Patent Publn. 20050209261
U.S. Patent Publn. 2007/0116680
U.S. Patent Publn. 2007/0238170
U.S. Patent Publn. 2008/0171385
U.S. Patent Publn. 2011/0229441
U.S. Patent Publn. 2012/0276063
U.S. Patent Publn. 2015/0010514
U.S. Patent Publn. 2015/0265652
U.S. Patent Publn. 2016/0177260
U.S. patent application Ser. No. 13/054,022
U.S. patent application Ser. No. 14/664,245
U.S. patent application Ser. No. 14/830,162
PCT/US2010/024487
PCT/US2011/046796
WO 2009/149233
WO 2010/141801
WO2013/067362
International Patent Publication No. 1998/30679
International Patent Publication No. 2001/088100
International Patent Publication No. 2002/076976
International Patent Publication No. 2003/059913
International Patent Publication No. 2003/062225
International Patent Publication No. 2003/062227
International Patent Publication No. 2004/039796
International Patent Publication No. 2005/080554
International Patent Publication No. 2005/123902
International Patent Publication No. 2013/067362
Amit et al., 2000.
Andrews et al., In: *Teratocarcinomas and Embryonic Stem Cells*, Robertson (Ed.), IRL Press, 207-246, 1987.
Animal Cell Culture, 1987.
Bottenstein and Sato, *Proc. Natl. Acad. Sci. USA*, 76:514-517, 1979.
Byrne et al., *Nature*, 450(7169):497-502, 2007.
Chen et al., *Cell*, 133:1106-1117, 2008.
Chen et al., *Nature Methods* 8:424-429, 2011.
Chung, et al., ES cell-derived renewable and functional midbrain dopaminergic progenitors, *Proc Natl Acad Sci USA*. 108(23):9703-8, 2011.
Current Protocols in Molecular Biology and Short Protocols in Molecular Biology, 1987 and 1995.
Doe et al., *J. Pharmacol. Exp. Ther.*, 32:89-98, 2007.
Embryonic Stem Cell Differentiation in vitro, 1993.
Evans et. al., *Nature*, 292:154, 1981.
Fernandes, et al., *J. Biotechnology*, 132(2):227-236, 2007.
Gene Targeting, A Practical Approach, IRL Press at Oxford University Press, 1993.
Gene Transfer Vectors for Mammalian Cells, 1987.
Greber et al., *Stem Cells*, 25:455-464, 2007.
Guide to Techniques in Mouse Development, 1993.
Harb et al., *PLoS One*, 20; 3(8):e3001, 2008.
*In vitro Methods in Pharmaceutical Research*, Academic Press, 1997.
Ishizaki, et al., *Mol. Pharmacol.*, 57:976-983, 2000.
Jaeger et al., *Development*, 138(20):4363-74, October 2011
Jiang et al., 2012.
Jainchill et al., *J. Virol.*, 4:549, 1969.
Keller et al., *Curr. Opin. Cell Biol.*, 7:862-869, 1995.
Kim et al, *Nature*, 418:50-56, 2002.
Kirkeby et al., Generation of Regionally Specified Neural Progenitors and Functional Neurons from Human Embryonic Stem Cells under Defined Conditions, *Cell Rep.* 1(6):703-14, 2012.
Klimanskaya et al., *Lancet.*, 365:P1636-1641, 2005.
Kodama et al., *J. Cell. Physiol.*, 112:89, 1982.
Krencik and Zhang, *Nature Protocols* 6(11):1710-1717, 2011.
Krencik et al., *Nature Biotechnology* 29:528-534, 2011.
Kriks, et al., Dopamine Neurons derived from human ES cells efficiently engraft in animal models of Parkinson's disease, *Nature*. 480(7378):547-51, 2011.
Ludwig et al., *Nat. Biotechnol.*, 24(2):185-187, 2006b.
Ludwig et al., *Nat. Methods*, 3(8):637-46, 2006a.
Manipulating the Mouse Embryo A Laboratory Manual, Second Edition, Cold Spring Harbor Laboratory Press, 1994.
Martin, *Proc. Natl. Acad. Sci. USA*, 78:7634, 1981.
Mouse Development, 1993.
Nakajima et al., *Cancer Chemother. Pharmacol.*, 52:319-324, 2003.
Nakano et al., *Science*, 272, 722, 1996.
Ogawa et al., *J. Cell Sci.*, 120:55-65, 2007.
Parkin controls dopamine utilization in human midbrain dopaminergic derived from induced pluripotent stem cells" *Nat Commun.*, 3:668, 2012.
Perrier et al., *Proc. Natl. Acad. Sci. USA*, 101(34):12543-8, 2004.
Properties and uses of Embryonic Stem Cells: Prospects for Application to Human Biology and Gene Therapy, 1998.
Reubinoff et al., *Nat. Biotechnol.*, 18:399-404, 2000.
Sasaki et al., *Pharmacol. Ther.*, 93:225-232, 2002.
Schwartz et al., *Methods* 45(2): 142-158, 2008.
Smith, In: *Origins and Properties of Mouse Embryonic Stem Cells*, Annu. Rev. Cell. Dev. Biol., 2000.
Sterneckert et al., *Stem Cells*, 28:1772-1781, 2010.
Suzuki et al., *Proc. Natl. Acad. Sci. USA*, 103:10294-10299., 2006.
Takahashi and Yamanaka, *Cell*, 126:663-676, 2006.
Takahashi et al., *Cell*, 126(4):663-76, 2006.
Takahashi et al., *Cell*, 131:861-872, 2007.
Thomson and Marshall, *Curr. Top. Dev. Biol.*, 38:133-165, 1998.
Thomson and Odorico, *J. Trends. Biotechnol.*, 18:53B57, 2000.
Thomson et al. *Proc. Natl. Acad. Scie. USA*, 92:7844-7848, 1995.
Thomson et al., *Science*, 282:1145, 1998.
Watabe and Miyazono, *Cell Res.*, 19:103-115, 2009.
Watanabe et al., *Nature Neurosci.*, 8:288-296, 2005.
Xi et al., *Stem Cells*. 30(8):1655-63., 2012.
Xu et al., *Cell Stem Cell*, 3:196-206., 2008.
Xu et al., *Nat. Biotechnol.*, 19:971-974, 2001.
Yakubov et al., *Biochemical and Biophysical Research Communications* 394: 189-193, 2010.
Ying et al., *Cell*, 115:281-292, 2003.

Young et al., *Mol Ther.* 22(8):1530-43, 2014.
Yu and Thomson, *Genes Dev.* 22(15):1987-97, 2008.
Yu et al., *Science,* 318:1917-1920, 2007.
Yu et al., *Nature Medicine,* 14: 1363, 2008.
Yu et al., *Science,* 324(5928):797-801, 2009.

What is claimed is:

1. An in vitro method for preparing a cell composition comprising human cells that express both forkhead box protein A2 (FOXA2) and LIM homeobox transcription factor 1 (LMX1) (FOXA2$^+$/LMX1$^+$ cells) comprising culturing human pluripotent cells in the presence of the following signaling modulators:
   (a) a single inhibitor of Small Mothers Against Decapentaplegic (SMAD) signaling,
   (b) at least one activator of Sonic hedgehog (SHH) signaling, and
   (c) at least one activator of wingless (Wnt) signaling;
   and culturing said cells in the presence of said modulators for a period of time sufficient to provide a cell composition comprising said FOXA2$^+$/LMX1$^+$ cells;
   wherein the culturing does not comprise culturing the human pluripotent cells in the presence of a second inhibitor of Small Mothers Against Decapentaplegic (SMAD) signaling.

2. The method of claim 1, wherein the single inhibitor of SMAD signaling is a BMP inhibitor.

3. The method of claim 2, wherein the BMP inhibitor is LDN-193189, dorsomorphin, DMH-1, or noggin.

4. The method of claim 3, wherein the BMP inhibitor is LDN-193189.

5. The method of claim 4, wherein the LDN-193189 is present at a concentration of from about 0.2 µM to about 4 µM.

6. The method of claim 5, wherein the LDN-193189 is present at a concentration of from about 1 µM to about 3 µM.

7. The method of claim 1, wherein the single inhibitor of SMAD signaling is a TGFβ inhibitor.

8. The method of claim 7, wherein the TGFβ inhibitor is SB431542.

9. The method of claim 1, wherein the pluripotent cells are cultured with the single inhibitor of SMAD on culture days 1-15, 1-16, or 1-17.

10. The method of claim 9, wherein the pluripotent cells are cultured with the single inhibitor of SMAD on culture days 1-17.

11. The method of claim 1, wherein the pluripotent cells are cultured with the single inhibitor of SMAD substantially continuously or on a daily basis for 15, 16, or 17 days.

12. The method of claim 11, wherein the pluripotent cells are cultured with the single inhibitor of SMAD substantially continuously or on a daily basis for 17 days.

13. The method of claim 1, wherein the single inhibitor of SMAD is present at a concentration of about 50-2000 or 50-500 nM.

14. The method of claim 13, wherein the single inhibitor of SMAD is present at a concentration of about 180-240 nM.

15. The method of claim 1, wherein the method further comprises contacting the pluripotent cells with a MEK inhibitor.

16. The method of claim 15, wherein the MEK inhibitor is PD0325901.

17. The method of claim 16, where the PD0325901 is present at a concentration of about 0.25-2.5 µM.

18. The method of claim 15, wherein the MEK inhibitor is contacted to the pluripotent cell for about 1-3 days, on days 1-3, 2-4, 3-5, or on days 1, 2, 3, 4, or 5, after initiation of contact with the single inhibitor of SMAD signaling.

19. The method of claim 15, wherein the MEK inhibitor is contacted to the pluripotent cells from about 24 to about 48 hours after initiation of contact with the single inhibitor of SMAD signaling.

20. The method of claim 15, wherein the MEK inhibitor is contacted to the pluripotent cells on a daily or substantially continual basis for about 3-4 days beginning about 1-2 days after initiation of contact with the single inhibitor of SMAD signaling.

21. The method of claim 20, wherein the MEK inhibitor is contacted to the pluripotent cells on days 2-5 or days 3-6 after initiation of contact with the single inhibitor of SMAD signaling on day 1.

22. The method of claim 1, wherein the activator of Wnt signaling is a GSK3 inhibitor.

23. The method of claim 22, wherein the GSK3 inhibitor is CHIR99021.

24. The method of claim 23, wherein the CHIR99021 is present at a concentration of about 0.5-3 µM.

25. The method of claim 24, wherein the CHIR99021 is present at a concentration of from greater than about 1.25 µM to about 2 µM.

26. The method of claim 23, wherein the CHIR99021 is present at a concentration of about 4-7 µM on days 9-17 after initiation of contact with the single inhibitor of SMAD signaling.

27. The method of claim 1, wherein the activator of Wnt signaling is contacted to the pluripotent cells 1-3 days after initiation of contact with the single inhibitor of SMAD signaling.

28. The method of claim 1, wherein the activator of Wnt signaling is contacted to the pluripotent cells within 24-48 hours after initiation of contact with the single inhibitor of SMAD signaling.

29. The method of claim 1, wherein the pluripotent cells are cultured with the activator of Wnt signaling substantially continuously or on a daily basis for 14, 15, or about 16 days.

30. The method of claim 1, wherein the activator of Wnt signaling is contacted to the pluripotent cells on days 2-17 after initiation of contact with the single inhibitor of SMAD signaling.

31. The method of claim 1, wherein the activator of SHH signaling is purmorphamine or C25II Shh.

32. The method of claim 31, wherein the method further comprises contacting the pluripotent cells with two activators of SHH signaling.

33. The method of claim 32, wherein the two activators of SHH signaling are purmorphamine and C25II Shh.

34. The method of claim 1, wherein the at least one activator of SHH signaling is contacted to the pluripotent cells on the same day as initiation of contact with the single inhibitor of SMAD signaling or within 24-48 hours after initiation of contact with the single inhibitor of SMAD signaling.

35. The method of claim 1, wherein the at least one activator of SHH signaling is contacted to the pluripotent cells on days 1-7 with or after initiation of contact with the single inhibitor of SMAD signaling.

36. The method of claim 1, wherein the method further comprises contacting the pluripotent cells with FGF-8.

37. The method of claim 36, wherein the FGF-8 is not contacted to the pluripotent cells on the same day as the initiation of contact with the single inhibitor of SMAD signaling.

38. The method of claim 36, wherein the FGF-8 is contacted with the pluripotent cells on days 9-17 or 11-17 after initiation of contact with the single inhibitor of SMAD signaling.

39. The method of claim 36, wherein the FGF-8 is present at a concentration of about 50-200 ng/mL.

40. The method of claim 1, wherein the pluripotent cells comprise an antibiotic resistance transgene under the control of a neuronal promoter.

41. The method of claim 1, wherein the method further comprises selecting for neural cells or midbrain DA neurons derived from the pluripotent cells by contacting cells with an antibiotic, a chemotherapeutic, a DNA crosslinker, a DNA synthesis inhibitors, or a mitotic inhibitor.

42. The method of claim 1, wherein the method further comprises contacting the pluripotent cells with an antibiotic or a chemotherapeutic.

43. The method of claim 41, wherein the chemotherapeutic is mitomycin C.

44. The method of claim 43, wherein the mitomycin C is contacted with the pluripotent cells on days 27, 28, and/or 29 after initiation of contact with the single inhibitor of SMAD signaling.

45. The method of claim 41, wherein the antibiotic is G418(geneticin).

46. The method of claim 1, wherein the method further comprises culturing or incubating the pluripotent cells in a media comprising a ROCK inhibitor prior to initiation of contact with the single inhibitor of SMAD signaling.

47. The method of claim 1, wherein the method further comprises contacting the pluripotent cells with blebbistatin.

48. The method of claim 1, wherein the blebbistatin is contacted with the cells on day 5 and day 17 of differentiation.

49. The method of claim 1, wherein at least 40% of cells differentiate and express both FOXA2 and LMX1.

50. The method of claim 49, wherein at least 60% of cells differentiate and express both FOXA2 and LMX1.

51. The method of claim 50, wherein at least 80% of cells differentiate and express both FOXA2 and LMX1.

52. The method of claim 50, wherein at least 85% of cells differentiate and express both FOXA2 and LMX1.

53. The method of claim 1, wherein at least 50% of cells differentiate and express both FOXA2 and tyrosine hydroxylase (TH).

54. The method of any one of claims 53, wherein at least 70% of cells differentiate and express both FOXA2 and tyrosine hydroxylase (TH).

55. The method of claim 1, wherein the pluripotent cells are human induced pluripotent stem (iPS) cells.

56. The method of claim 1, wherein the LMX1 is LIM homeobox transcription factor 1 alpha (LMX1A).

57. The method of claim 49, wherein the differentiated cells expressing FOXA2 and LMX1 further express at least one marker selected from the group consisting of orthodenticle homeobox 2 (OTX2), nuclear receptor related 1 protein (NURR1), Neuron-specific class III beta-tubulin (Tujl), TTF3, paired-like homeodomain 3 (PITX3), achaete-scute complex (ASCL), early B-cell factor 1 (EBF-1), early B-cell factor 3 (EBF-3), transthyretin (TTR), synapsin, dopamine transporter (DAT), G-protein coupled, inwardly rectifying potassium channel (Kir3.2/GIRK2), CD 142, DCSM1, CD63, and CD99.

58. The method of claim 1, wherein the method further comprises incubating human pluripotent cells in the presence of a DNase or an endonuclease.

59. The method of claim 58, wherein the endonuclease is DNase I or Benzonase®.

60. The method of claim 59, wherein the DNase I or Benzonase® is present at a concentration of about 100 U/mL.

61. The method of claim 58, wherein the human pluripotent cells are cultured in the presence of an endonuclease on at least one of days 4-6 after initiation of contact with the single inhibitor of SMAD signaling.

62. The method of claim 58, wherein the human pluripotent cells are cultured in the presence of an endonuclease on day 5 after initiation of contact with the single inhibitor of SMAD signaling.

* * * * *

UNITED STATES PATENT AND TRADEMARK OFFICE
CERTIFICATE OF CORRECTION

PATENT NO. : 10,590,383 B2
APPLICATION NO. : 15/678432
DATED : March 17, 2020
INVENTOR(S) : McMahon et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 68 days.

Signed and Sealed this
Twenty-fourth Day of November, 2020

Andrei Iancu
*Director of the United States Patent and Trademark Office*